(12) United States Patent
Justin et al.

(10) Patent No.: US 8,128,627 B2
(45) Date of Patent: Mar. 6, 2012

(54) SEGMENTED INTRAMEDULLARY SYSTEM AND APPARATUS

(75) Inventors: Daniel F. Justin, Logan, UT (US); Karen E. Mohr, Salt Lake City, UT (US); Carlyle J. Creger, River Heights, UT (US); Jeremy D. Borchert, Logan, UT (US); James D. Stoneburner, Santa Clara, CA (US); Mojan Goshayesh, Atherton, CA (US); Matthew T. Harmon, Santa Cruz, CA (US); Roelof Trip, Suwanee, GA (US); Charles E. Larsen, Tampa, FL (US)

(73) Assignee: Sonoma Orthopedic Products, Inc., Santa Rosa, CA (US)

( * ) Notice: Subject to any disclaimer, the term of this patent is extended or adjusted under 35 U.S.C. 154(b) by 290 days.

(21) Appl. No.: 12/345,451

(22) Filed: Dec. 29, 2008

(65) Prior Publication Data

US 2009/0228008 A1   Sep. 10, 2009

Related U.S. Application Data

(63) Continuation-in-part of application No. 12/052,919, filed on Mar. 21, 2008.

(60) Provisional application No. 60/896,342, filed on Mar. 22, 2007, provisional application No. 61/055,747, filed on May 23, 2008.

(51) Int. Cl.
*A61B 17/56* (2006.01)
*A61B 17/58* (2006.01)
*A61F 2/30* (2006.01)

(52) U.S. Cl. .................. 606/62; 606/60; 606/95

(58) Field of Classification Search .............. 606/62–64, 606/95, 96, 80; 623/20.32–20.36, 21.11, 623/21.12, 21.15
See application file for complete search history.

(56) References Cited

U.S. PATENT DOCUMENTS 2,998,007 A   8/1961   Herzog
(Continued)

FOREIGN PATENT DOCUMENTS

DE   2657303   6/1977
(Continued)

OTHER PUBLICATIONS

PCT Notification of Transmittal of the International Search Report and the Written Opinion of the Searching Authority in PCT/US2008/057868 dated Sep. 22, 2008 in 16 pages.
(Continued)

*Primary Examiner* — Eduardo C Robert
*Assistant Examiner* — Christina Negrelli
(74) *Attorney, Agent, or Firm* — Knobbe Martens Olson & Bear LLP

(57) ABSTRACT

An implantable segmented intramedullary structure adapted to be received in the intramedullary canal of a bone configurable between a relatively flexible, bent configuration for implantation or extraction and a relatively rigid, straightened configuration for bone treatment. The segmented intramedullary structure comprises a plurality of interconnected segments with a first interface and a complementarily-shaped second interface such that the first interface of a segment cooperatively engages the second interface of an adjacent segment. The segments define a channel for a tensioning member to lock the structure in a compressed configuration.

20 Claims, 41 Drawing Sheets

U.S. PATENT DOCUMENTS

| | | |
|---|---|---|
| 3,759,257 A | 9/1973 | Fischer et al. |
| 3,760,802 A | 9/1973 | Fischer et al. |
| 3,846,846 A | 11/1974 | Fischer |
| 4,091,806 A | 5/1978 | Aginsky |
| 4,204,531 A | 5/1980 | Aginsky |
| 4,227,518 A | 10/1980 | Aginsky |
| 4,262,665 A | 4/1981 | Roalstad et al. |
| 4,457,301 A | 7/1984 | Walker |
| 4,522,200 A | 6/1985 | Stednitz |
| 4,653,487 A | 3/1987 | Maale |
| 4,706,659 A | 11/1987 | Matthews et al. |
| 4,721,103 A | 1/1988 | Freedland |
| 4,756,307 A | 7/1988 | Crowninshield |
| 4,776,330 A | 10/1988 | Chapman et al. |
| 4,805,607 A | 2/1989 | Engelhardt et al. |
| 4,846,162 A | 7/1989 | Moehring |
| 4,854,312 A | 8/1989 | Raftopoulos et al. |
| 4,858,602 A | 8/1989 | Seidel et al. |
| 4,875,475 A | 10/1989 | Comte et al. |
| 4,895,572 A | 1/1990 | Chernoff |
| 4,938,769 A | 7/1990 | Shaw |
| 5,002,543 A | 3/1991 | Bradshaw et al. |
| 5,008,398 A | 4/1991 | Koehler et al. |
| 5,019,108 A | 5/1991 | Bertin et al. |
| 5,035,697 A | 7/1991 | Frigg |
| 5,041,114 A | 8/1991 | Chapman et al. |
| 5,041,115 A | 8/1991 | Frigg et al. |
| 5,053,035 A | 10/1991 | Mclaren |
| 5,057,103 A | 10/1991 | Davis |
| 5,074,882 A | 12/1991 | Grammont et al. |
| 5,108,437 A | 4/1992 | Kenna |
| 5,112,333 A | 5/1992 | Fixel |
| 5,122,141 A | 6/1992 | Simpson et al. |
| 5,135,527 A | 8/1992 | Ender |
| 5,281,225 A | 1/1994 | Vicenzi |
| 5,364,398 A | 11/1994 | Chapman et al. |
| 5,415,660 A | 5/1995 | Campbell et al. |
| 5,423,850 A | 6/1995 | Berger |
| 5,429,640 A | 7/1995 | Shuler et al. |
| 5,472,444 A | 12/1995 | Huebner et al. |
| 5,480,400 A | 1/1996 | Berger |
| 5,484,439 A | 1/1996 | Olson et al. |
| 5,489,284 A | 2/1996 | James et al. |
| 5,501,695 A | 3/1996 | Anspach, Jr. et al. |
| 5,507,817 A | 4/1996 | Craig et al. |
| 5,516,335 A | 5/1996 | Kummer et al. |
| 5,549,610 A | 8/1996 | Russell et al. |
| 5,562,667 A | 10/1996 | Shuler et al. |
| 5,569,249 A | 10/1996 | James et al. |
| 5,618,286 A | 4/1997 | Brinker |
| 5,620,445 A | 4/1997 | Brosnahan et al. |
| 5,626,580 A | 5/1997 | Brosnahan |
| 5,649,925 A | 7/1997 | Barbera Alacreu |
| 5,653,709 A | 8/1997 | Frigg |
| 5,658,287 A | 8/1997 | Hofmann et al. |
| 5,658,349 A | 8/1997 | Brooks et al. |
| 5,702,389 A | 12/1997 | Taylor et al. |
| 5,702,486 A | 12/1997 | Craig et al. |
| 5,720,753 A | 2/1998 | Sander et al. |
| 5,725,541 A | 3/1998 | Anspach, III et al. |
| 5,772,662 A | 6/1998 | Chapman et al. |
| 5,776,194 A | 7/1998 | Mikol et al. |
| 5,782,865 A | 7/1998 | Grotz |
| 5,849,004 A | 12/1998 | Bramlet |
| 5,855,579 A | 1/1999 | James et al. |
| 5,879,352 A * | 3/1999 | Filoso et al. .................. 606/62 |
| 5,888,208 A | 3/1999 | Ro |
| 5,899,425 A | 5/1999 | Corey Jr. et al. |
| 5,944,719 A | 8/1999 | Leban |
| 6,010,506 A | 1/2000 | Gosney et al. |
| 6,019,761 A | 2/2000 | Gustilo |
| 6,053,922 A | 4/2000 | Krause et al. |
| 6,068,648 A | 5/2000 | Cole et al. |
| 6,083,244 A | 7/2000 | Lubbers et al. |
| 6,106,528 A | 8/2000 | Durham et al. |
| 6,123,708 A | 9/2000 | Kilpela et al. |
| 6,126,663 A | 10/2000 | Hair |
| 6,126,691 A | 10/2000 | Kasra et al. |
| 6,127,597 A | 10/2000 | Beyar et al. |
| 6,129,729 A | 10/2000 | Snyder |
| 6,168,595 B1 | 1/2001 | Durham et al. |
| 6,171,342 B1 | 1/2001 | O'Neill et al. |
| 6,183,474 B1 | 2/2001 | Bramlet et al. |
| 6,221,074 B1 | 4/2001 | Cole et al. |
| 6,224,600 B1 | 5/2001 | Protogirou |
| 6,228,086 B1 | 5/2001 | Wahl et al. |
| 6,241,734 B1 | 6/2001 | Scribner et al. |
| 6,248,110 B1 | 6/2001 | Reiley et al. |
| 6,261,289 B1 | 7/2001 | Levy |
| 6,264,699 B1 | 7/2001 | Noiles et al. |
| 6,294,187 B1 | 9/2001 | Boyce et al. |
| 6,296,644 B1 | 10/2001 | Saurat et al. |
| 6,319,286 B1 | 11/2001 | Fernandez et al. |
| 6,322,591 B1 | 11/2001 | Ahrens |
| 6,355,044 B1 | 3/2002 | Hair |
| 6,371,989 B1 | 4/2002 | Chauvin et al. |
| 6,402,753 B1 | 6/2002 | Cole et al. |
| 6,423,067 B1 | 7/2002 | Eisermann |
| 6,440,444 B2 | 8/2002 | Boyce et al. |
| 6,447,518 B1 | 9/2002 | Krause et al. |
| 6,517,541 B1 | 2/2003 | Sesic |
| 6,524,313 B1 | 2/2003 | Fassier et al. |
| 6,527,775 B1 | 3/2003 | Warburton |
| 6,547,791 B1 | 4/2003 | Buhren et al. |
| 6,551,321 B1 | 4/2003 | Burkinshaw et al. |
| 6,554,833 B2 | 4/2003 | Levy et al. |
| 6,569,165 B2 | 5/2003 | Wahl et al. |
| 6,575,973 B1 | 6/2003 | Shekalim |
| 6,582,453 B1 | 6/2003 | Tran et al. |
| 6,607,531 B2 | 8/2003 | Frigg |
| 6,629,999 B1 | 10/2003 | Serafin, Jr. |
| 6,635,061 B1 | 10/2003 | Snyder |
| 6,660,039 B1 | 12/2003 | Evans et al. |
| 6,663,670 B2 | 12/2003 | Rogers et al. |
| 6,669,701 B2 | 12/2003 | Steiner et al. |
| 6,692,530 B2 | 2/2004 | Doubler et al. |
| 6,696,073 B2 | 2/2004 | Boyce et al. |
| 6,712,855 B2 | 3/2004 | Martin et al. |
| 6,719,759 B2 | 4/2004 | Wagner et al. |
| 6,730,090 B2 | 5/2004 | Orbay et al. |
| 6,736,818 B2 | 5/2004 | Perren et al. |
| 6,740,120 B1 | 5/2004 | Grimes |
| 6,746,407 B2 | 6/2004 | Steuer et al. |
| 6,746,487 B2 | 6/2004 | Scifert et al. |
| 6,755,780 B2 | 6/2004 | Borst et al. |
| 6,755,862 B2 | 6/2004 | Keynan |
| 6,761,722 B2 | 7/2004 | Cole et al. |
| 6,783,530 B1 | 8/2004 | Levy |
| 6,783,551 B1 | 8/2004 | Metzger et al. |
| 6,793,659 B2 | 9/2004 | Putnam |
| 6,887,278 B2 | 5/2005 | Lewallen |
| 6,902,583 B2 | 6/2005 | Gerbec et al. |
| 6,908,465 B2 | 6/2005 | von Hoffmann et al. |
| 6,911,048 B2 | 6/2005 | Fernandez et al. |
| 6,921,400 B2 | 7/2005 | Sohngen |
| 6,926,719 B2 | 8/2005 | Sohngen et al. |
| 6,932,819 B2 | 8/2005 | Wahl et al. |
| 6,953,479 B2 | 10/2005 | Carson et al. |
| 6,960,163 B2 | 11/2005 | Ewers et al. |
| 6,994,725 B1 | 2/2006 | Goble |
| 7,001,386 B2 | 2/2006 | Sohngen et al. |
| 7,008,425 B2 | 3/2006 | Phillips |
| 7,052,498 B2 | 5/2006 | Levy et al. |
| 7,101,376 B2 | 9/2006 | Semet |
| 7,125,423 B2 | 10/2006 | Hazebrouck |
| 7,135,022 B2 | 11/2006 | Kosashvili et al. |
| 7,172,595 B1 | 2/2007 | Goble |
| 7,186,264 B2 | 3/2007 | Liddicoat et al. |
| 7,189,201 B2 | 3/2007 | Borst et al. |
| 7,237,556 B2 | 7/2007 | Smothers et al. |
| 7,250,028 B2 | 7/2007 | Julian et al. |
| 7,258,692 B2 | 8/2007 | Thelen et al. |
| 7,261,713 B2 | 8/2007 | Langmaid et al. |
| 7,267,678 B2 | 9/2007 | Medoff |
| 7,410,483 B2 | 8/2008 | Danitz et al. |
| 2001/0012939 A1 | 8/2001 | Wahl et al. |
| 2001/0018616 A1 | 8/2001 | Schwab |

| | | |
|---|---|---|
| 2002/0032444 A1 | 3/2002 | Mische |
| 2002/0068939 A1 | 6/2002 | Levy et al. |
| 2002/0099385 A1 | 7/2002 | Ralph et al. |
| 2002/0111629 A1 | 8/2002 | Phillips |
| 2002/0133156 A1 | 9/2002 | Cole |
| 2002/0143337 A1 | 10/2002 | Orbay et al. |
| 2002/0151898 A1 | 10/2002 | Sohngen et al. |
| 2003/0014120 A1 | 1/2003 | Carson et al. |
| 2003/0018336 A1 | 1/2003 | Vandewalle |
| 2003/0050704 A1 | 3/2003 | Keynan |
| 2003/0069580 A1 | 4/2003 | Langmaid et al. |
| 2003/0069581 A1 | 4/2003 | Stinson et al. |
| 2003/0100906 A1 | 5/2003 | Rosa et al. |
| 2003/0100907 A1 | 5/2003 | Rosa et al. |
| 2003/0109932 A1 | 6/2003 | Keynan |
| 2003/0114855 A1 | 6/2003 | Wahl et al. |
| 2003/0139818 A1 | 7/2003 | Rogers et al. |
| 2003/0181918 A1 | 9/2003 | Smothers et al. |
| 2003/0187449 A1 | 10/2003 | McCleary et al. |
| 2003/0195515 A1 | 10/2003 | Sohngen |
| 2003/0204269 A1 | 10/2003 | Gerbec et al. |
| 2004/0087955 A1 | 5/2004 | Bordi |
| 2004/0133204 A1 | 7/2004 | Davies |
| 2004/0153082 A1 | 8/2004 | Howie et al. |
| 2004/0193267 A1 | 9/2004 | Jones et al. |
| 2004/0193268 A1 | 9/2004 | Hazebrouck |
| 2004/0230193 A1 | 11/2004 | Cheung et al. |
| 2005/0010223 A1 | 1/2005 | Gotfried |
| 2005/0033366 A1 | 2/2005 | Cole et al. |
| 2005/0055023 A1 | 3/2005 | Sohngen et al. |
| 2005/0071014 A1 | 3/2005 | Barnett et al. |
| 2005/0075637 A1 | 4/2005 | Semet |
| 2005/0107793 A1 | 5/2005 | Manderson |
| 2005/0125067 A1 | 6/2005 | Sweeney |
| 2005/0187550 A1 | 8/2005 | Grusin |
| 2005/0216007 A1 | 9/2005 | Woll et al. |
| 2005/0271694 A1 | 12/2005 | Mansouri et al. |
| 2005/0273103 A1 | 12/2005 | Wahl et al. |
| 2005/0277936 A1 | 12/2005 | Siravo et al. |
| 2006/0004459 A1 | 1/2006 | Hazebrouck et al. |
| 2006/0004465 A1 | 1/2006 | Bergin et al. |
| 2006/0009774 A1 | 1/2006 | Goble et al. |
| 2006/0009853 A1 | 1/2006 | Justin et al. |
| 2006/0009854 A1 | 1/2006 | Justin et al. |
| 2006/0009855 A1 | 1/2006 | Goble et al. |
| 2006/0030945 A1 | 2/2006 | Wright |
| 2006/0041317 A1 | 2/2006 | Hazebrouck et al. |
| 2006/0167464 A1 | 7/2006 | Allen et al. |
| 2006/0264950 A1 | 11/2006 | Nelson et al. |
| 2006/0264951 A1 | 11/2006 | Nelson et al. |
| 2006/0264952 A1 | 11/2006 | Nelson et al. |
| 2007/0016194 A1 | 1/2007 | Shaolian et al. |
| 2007/0123877 A1 | 5/2007 | Goldin et al. |
| 2007/0169782 A1 | 7/2007 | Smothers et al. |
| 2007/0173834 A1 | 7/2007 | Thakkar |
| 2007/0208223 A1 | 9/2007 | Julian et al. |
| 2007/0250113 A1 | 10/2007 | Hegeman et al. |
| 2008/0065116 A1 | 3/2008 | Lee et al. |
| 2008/0161805 A1 | 7/2008 | Saravia et al. |
| 2008/0287951 A1 | 11/2008 | Stoneburner et al. |
| 2009/0216232 A1 | 8/2009 | Buford et al. |
| 2009/0228007 A1 | 9/2009 | Justin et al. |

FOREIGN PATENT DOCUMENTS

| | | |
|---|---|---|
| DE | 10003331 A1 | 8/2001 |
| EP | 295041 | 9/1993 |
| EP | 726735 | 4/1997 |
| EP | 1153147 | 11/2001 |
| EP | 0882431 | 10/2002 |
| EP | 1278485 | 1/2003 |
| EP | 1148850 | 4/2005 |
| EP | 1522268 | 4/2005 |
| EP | 1582159 | 10/2005 |
| EP | 1582160 | 10/2005 |
| EP | 1582161 | 10/2005 |
| EP | 1582162 | 10/2005 |
| EP | 1582163 | 10/2005 |
| EP | 1582164 | 10/2005 |
| EP | 1148851 | 5/2006 |
| EP | 1740113 | 1/2007 |
| EP | 1815813 | 8/2007 |
| EP | 1820462 | 8/2007 |
| FR | 2 801 189 A1 | 11/1999 |
| WO | WO9222268 | 12/1992 |
| WO | WO9313713 | 7/1993 |
| WO | WO9718769 | 5/1997 |
| WO | WO97/39693 | 10/1997 |
| WO | WO9818397 | 5/1998 |
| WO | WO9836699 | 8/1998 |
| WO | WO98/38918 | 9/1998 |
| WO | WO00/19924 | 4/2000 |
| WO | WO0149193 | 7/2001 |
| WO | WO02071961 | 9/2002 |
| WO | WO03068090 | 8/2003 |
| WO | WO2005094705 | 10/2005 |
| WO | WO2005102196 | 11/2005 |
| WO | WO2005/112804 | 12/2005 |
| WO | WO2005096976 | 1/2006 |
| WO | WO2006041460 | 4/2006 |
| WO | WO2007008177 | 1/2007 |
| WO | WO2007009123 | 1/2007 |
| WO | WO2007053960 | 5/2007 |
| WO | WO2008116170 | 9/2008 |
| WO | WO2008116175 | 9/2008 |

OTHER PUBLICATIONS

PCT Invitation to Pay Additional Fees with Search Results in PCT/US2009/044898 dated Aug. 27, 2009 in 6 pages.

PCT Notification of Transmittal of the International Search Report and the Written Opinion of the Searching Authority in PCT/US2009/044898 dated Dec. 7, 2010 in 16 pages.

Darron M. Jones et al., "Focal Osteolysis at the Junctions of a Modular Stainless-Steel Femoral Intramedullary Nail", The Journal of Bone & Joint Surgery • JBJS.Org vol. 83-A • No. 4 • Apr. 2001, pp. 537-548.

U.S. Appl. No. 12/345,225, filed Dec. 29, 2008.

U.S. Appl. No. 12/345,340, filed Dec. 29, 2008.

U.S. Appl. No. 12/345,451, filed Dec. 29, 2008.

PCT International Search Report and Written Opinion in PCT/US2008/057868 mailed Sep. 22, 2008.

PCT International Search Report in PCT/US2008/057868 dated Jul. 8, 2008.

"The Titanium Flexible Humeral Nail System: Quick Reference for Surgical Technique" Synthes publication from Jul. 1999.

European Communication pursuant to Article 94(3) EPC in European App. No. 09751602.5, dated Jul. 1, 2011 in 4 pages.

* cited by examiner

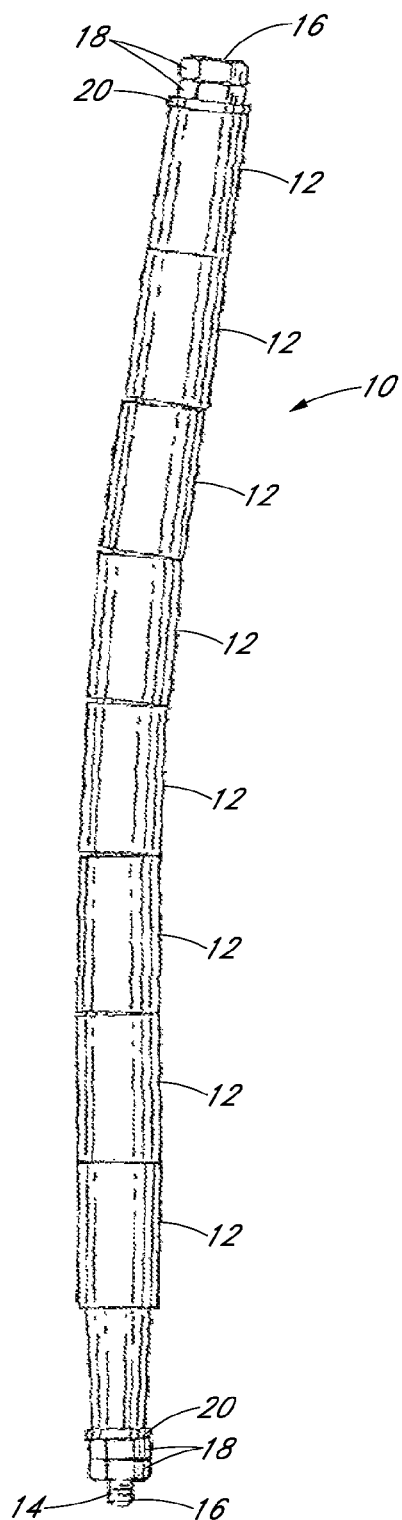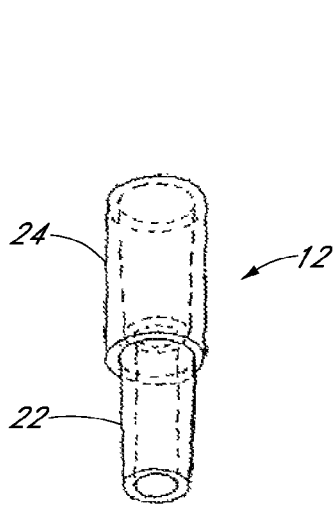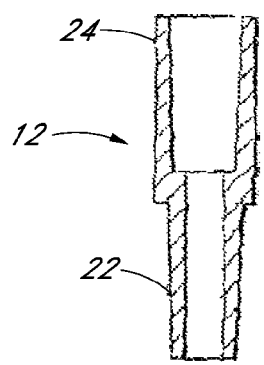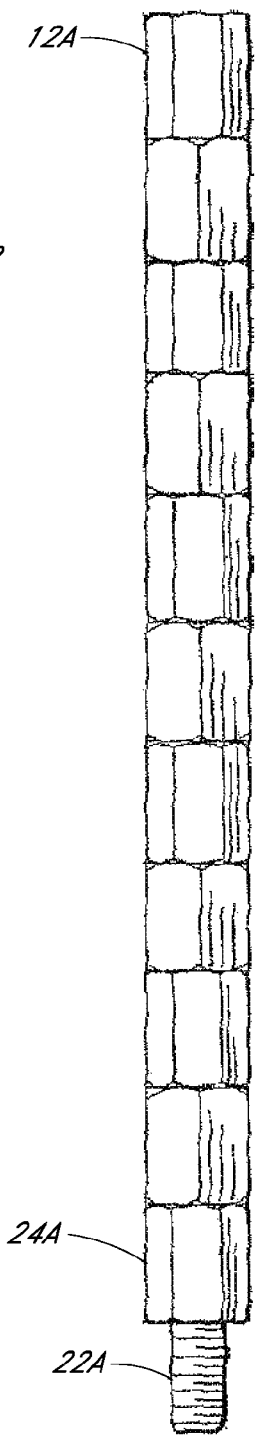
FIG. 1
FIG. 2
FIG. 3
FIG. 4

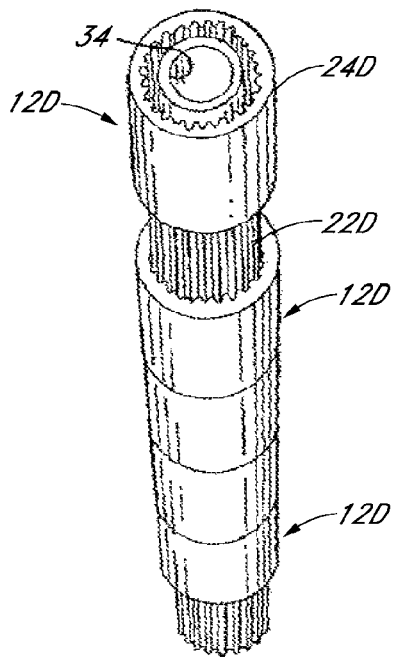
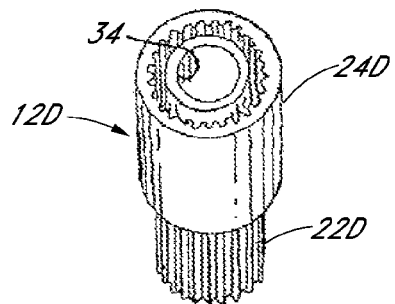
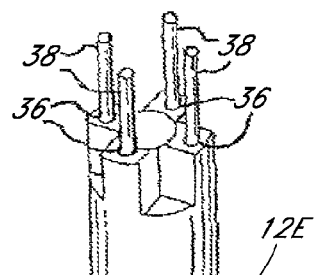
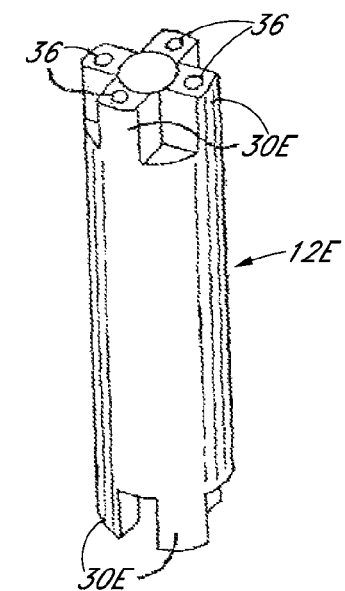
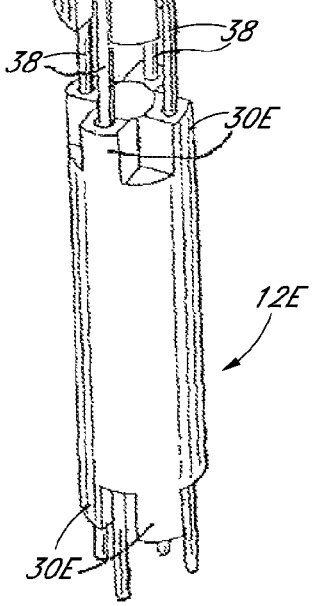
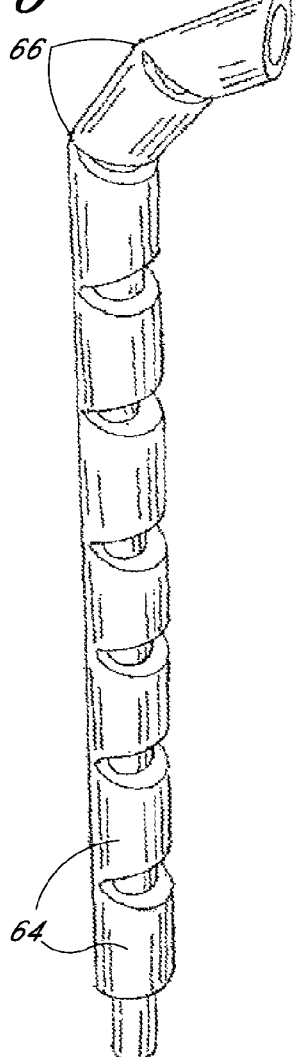
FIG. 9
FIG. 10
FIG. 12
FIG. 11
FIG. 13

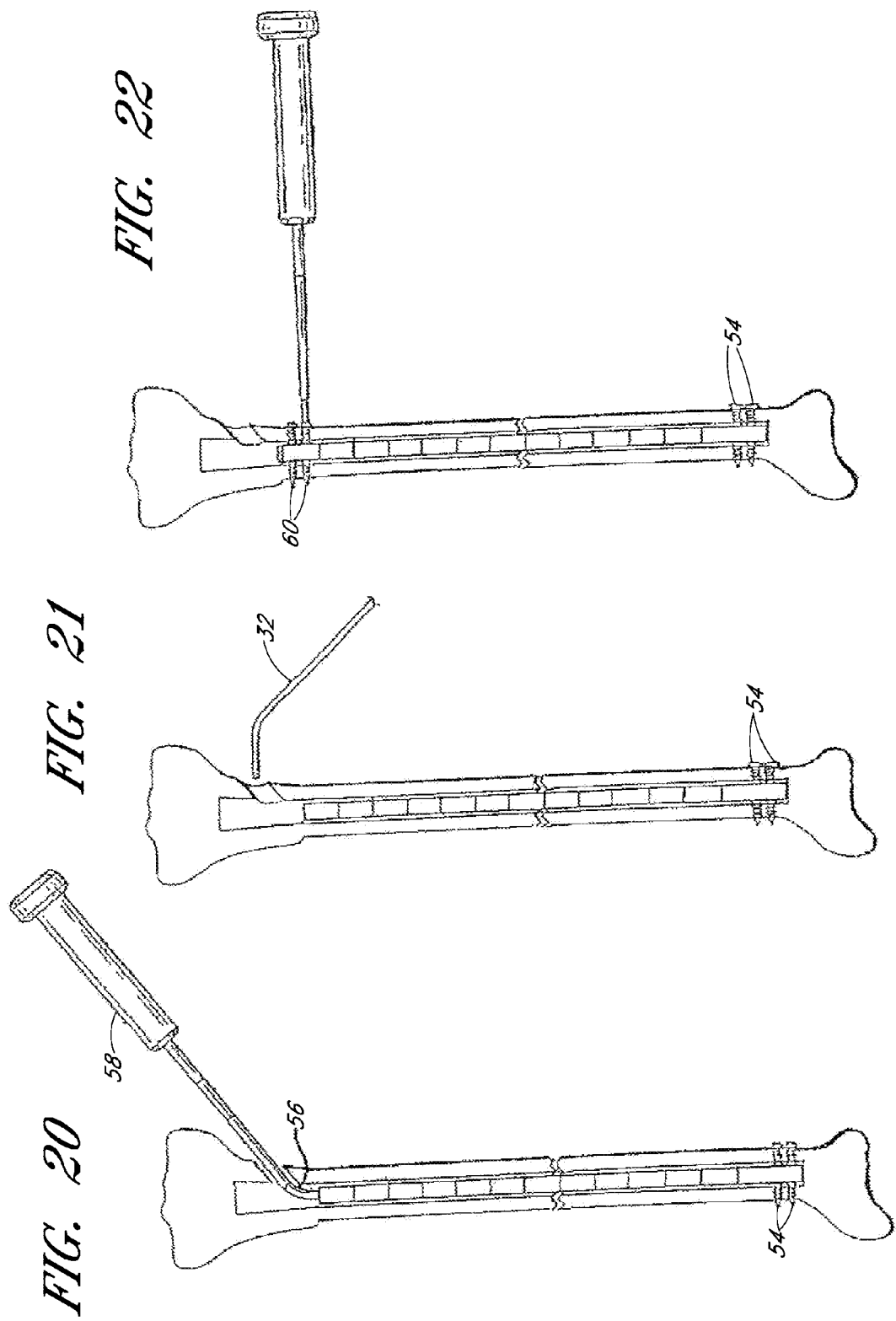

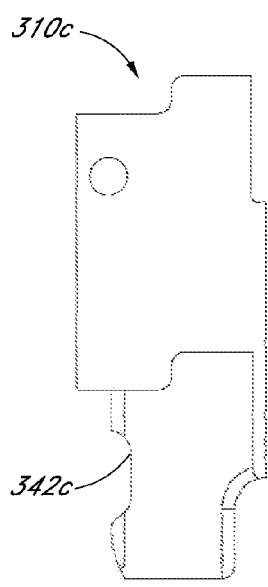 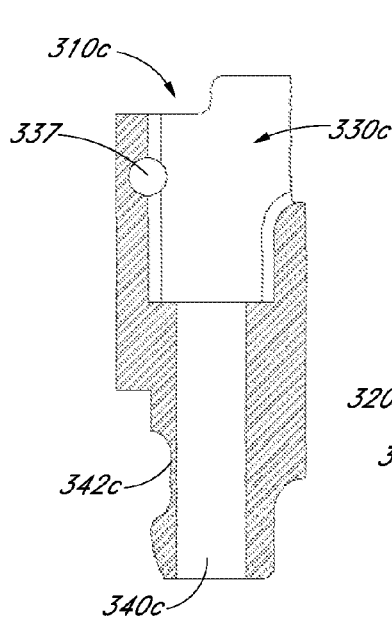 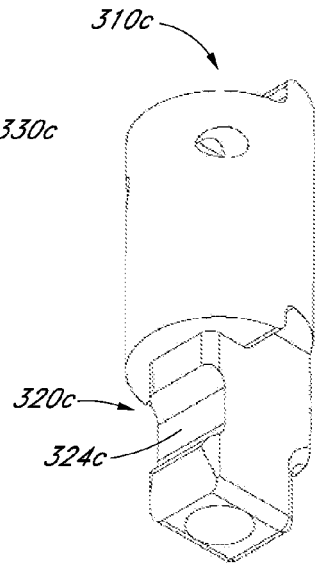
FIG. 47A  FIG. 47B  FIG. 47C
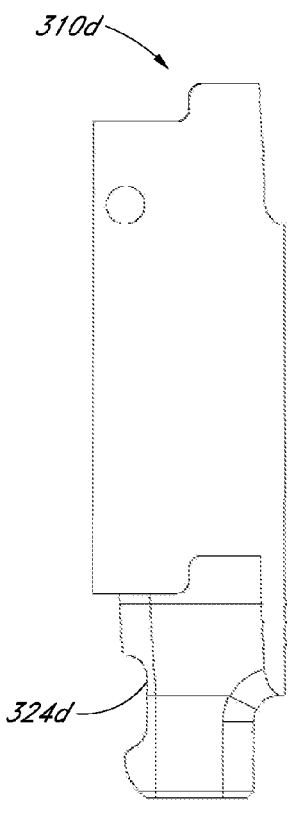 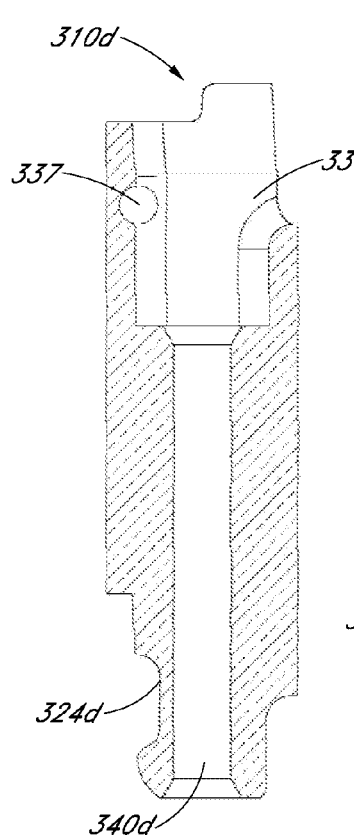 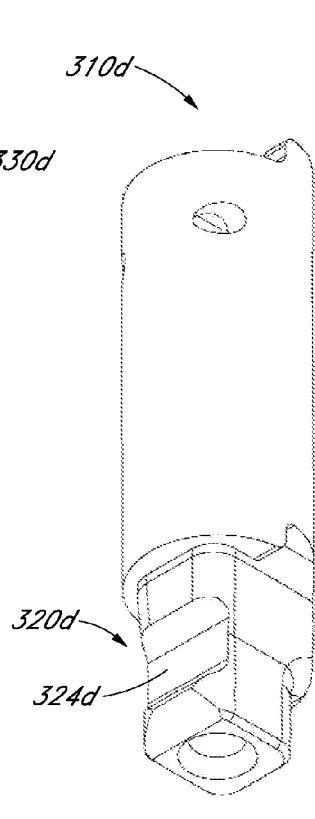
FIG. 48A  FIG. 48B  FIG. 48C

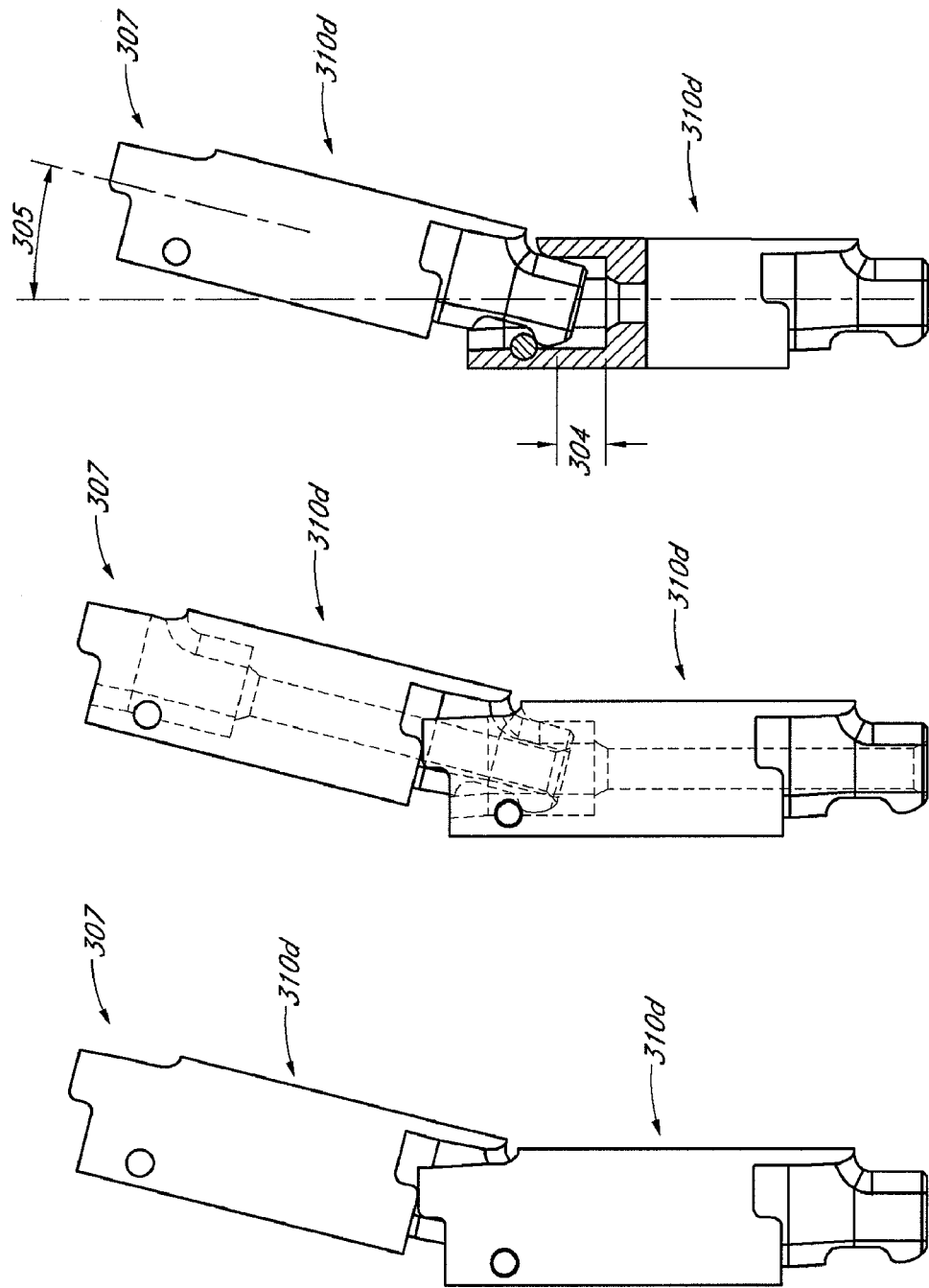

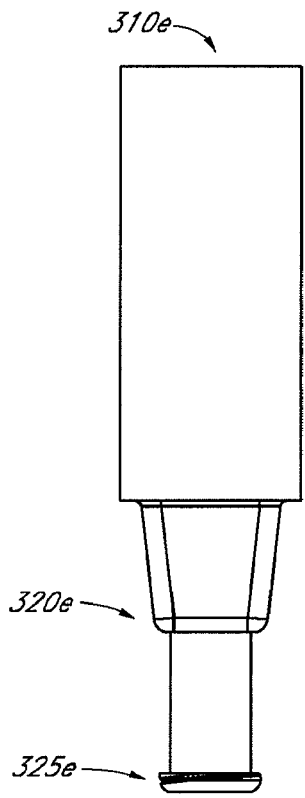
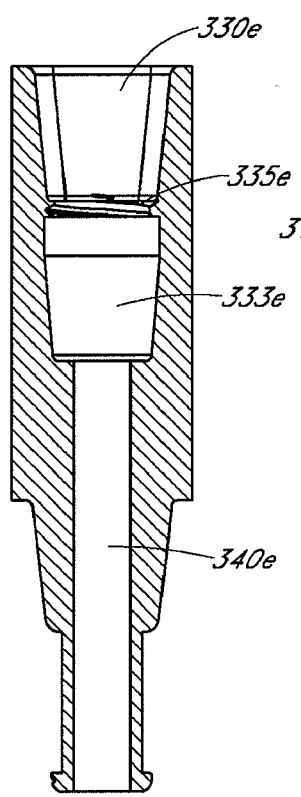
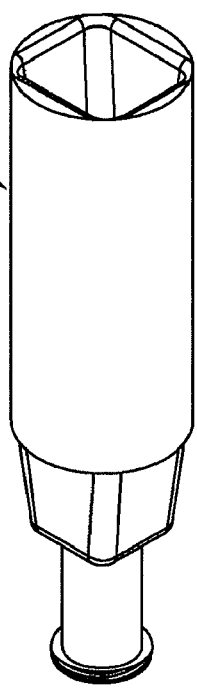
FIG. 51A     FIG. 51B     FIG. 51C
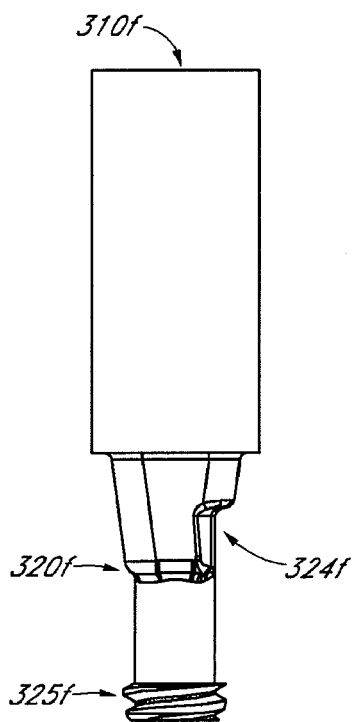
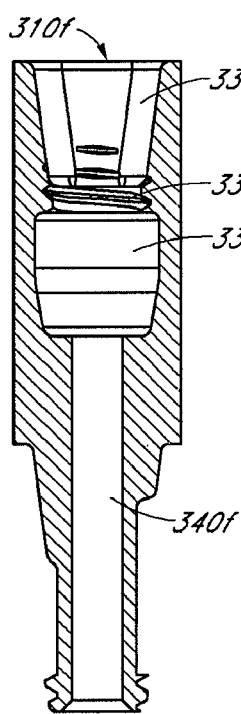
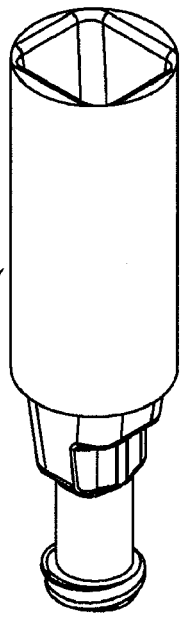
FIG. 52A     FIG. 52B     FIG. 52C

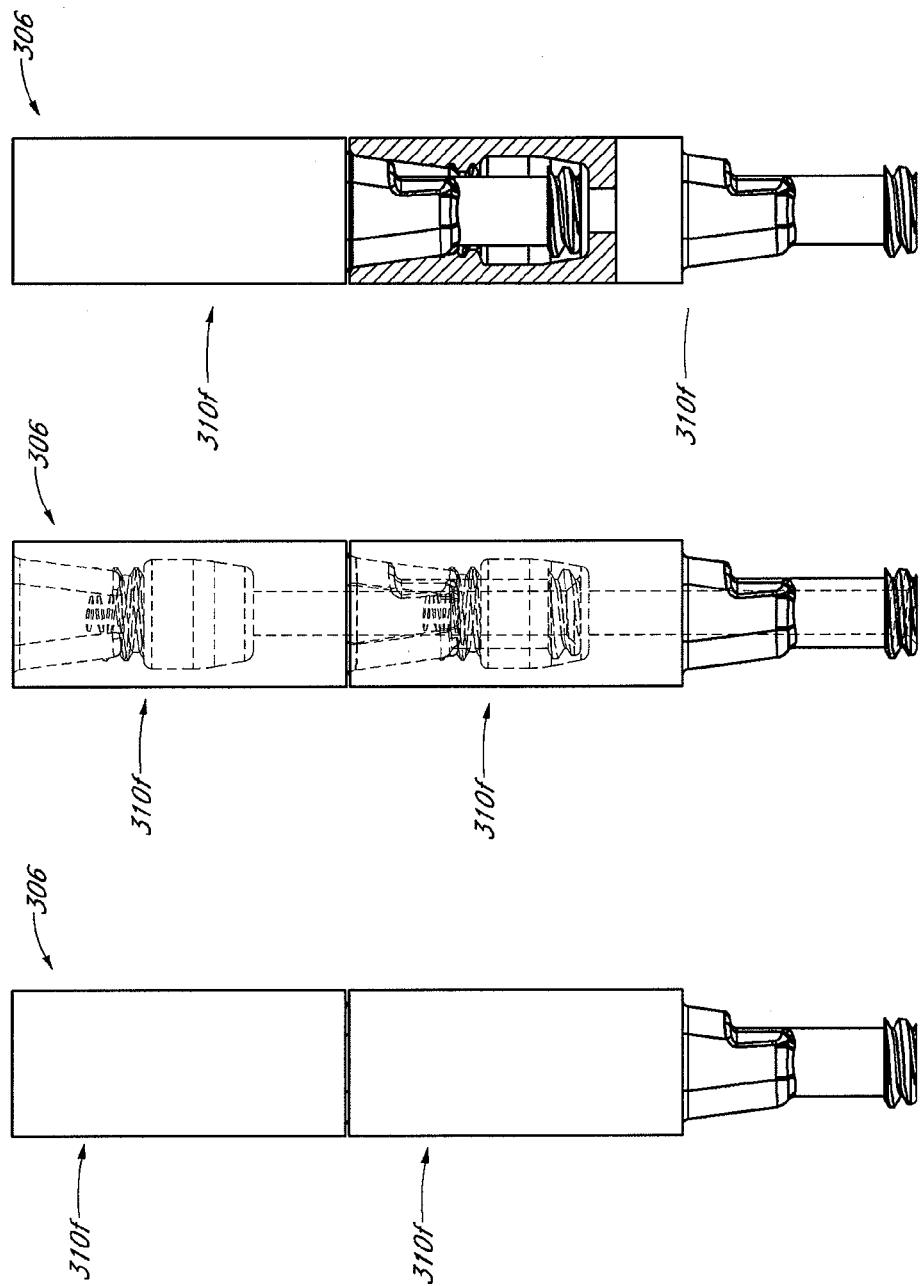

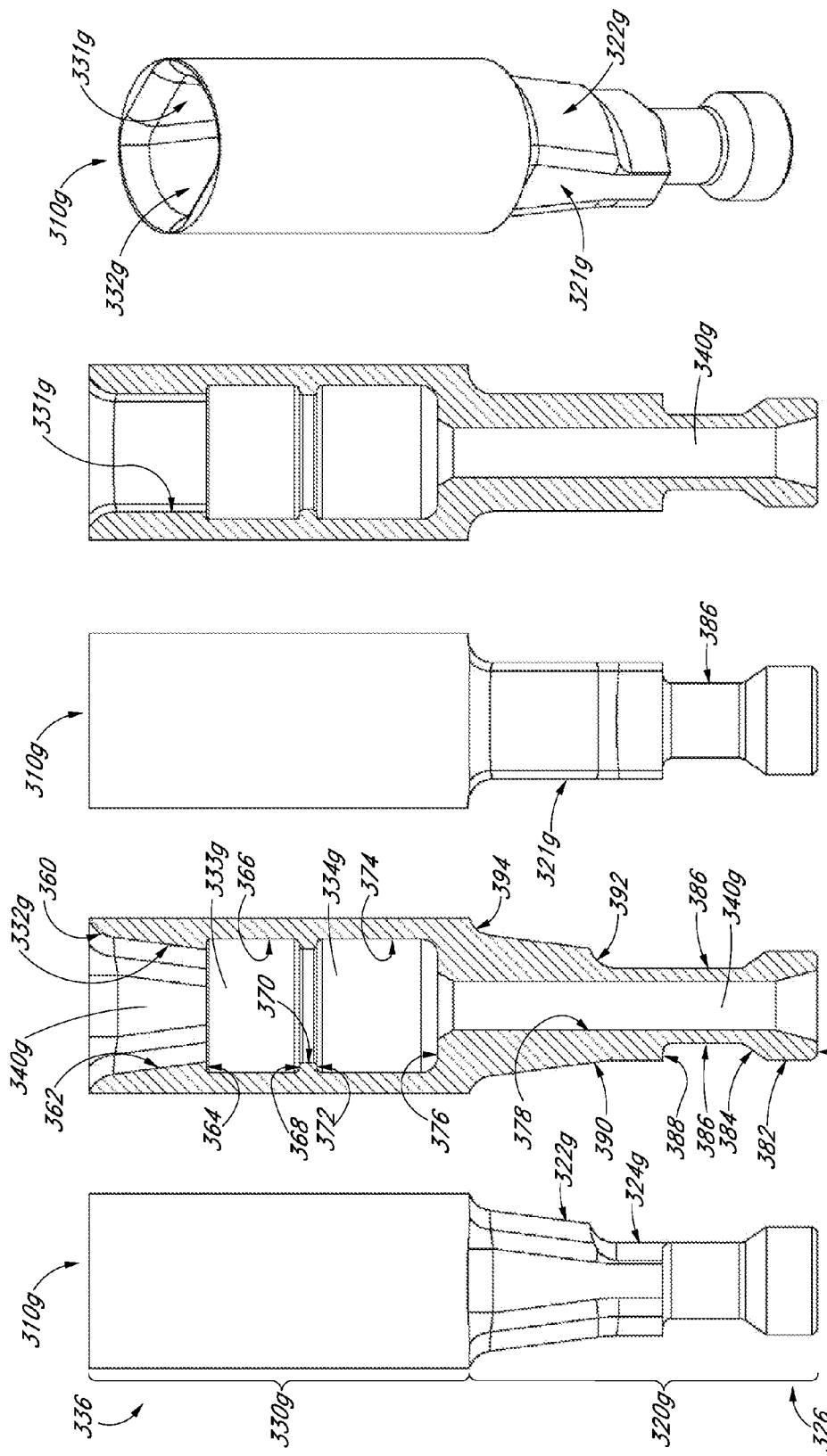

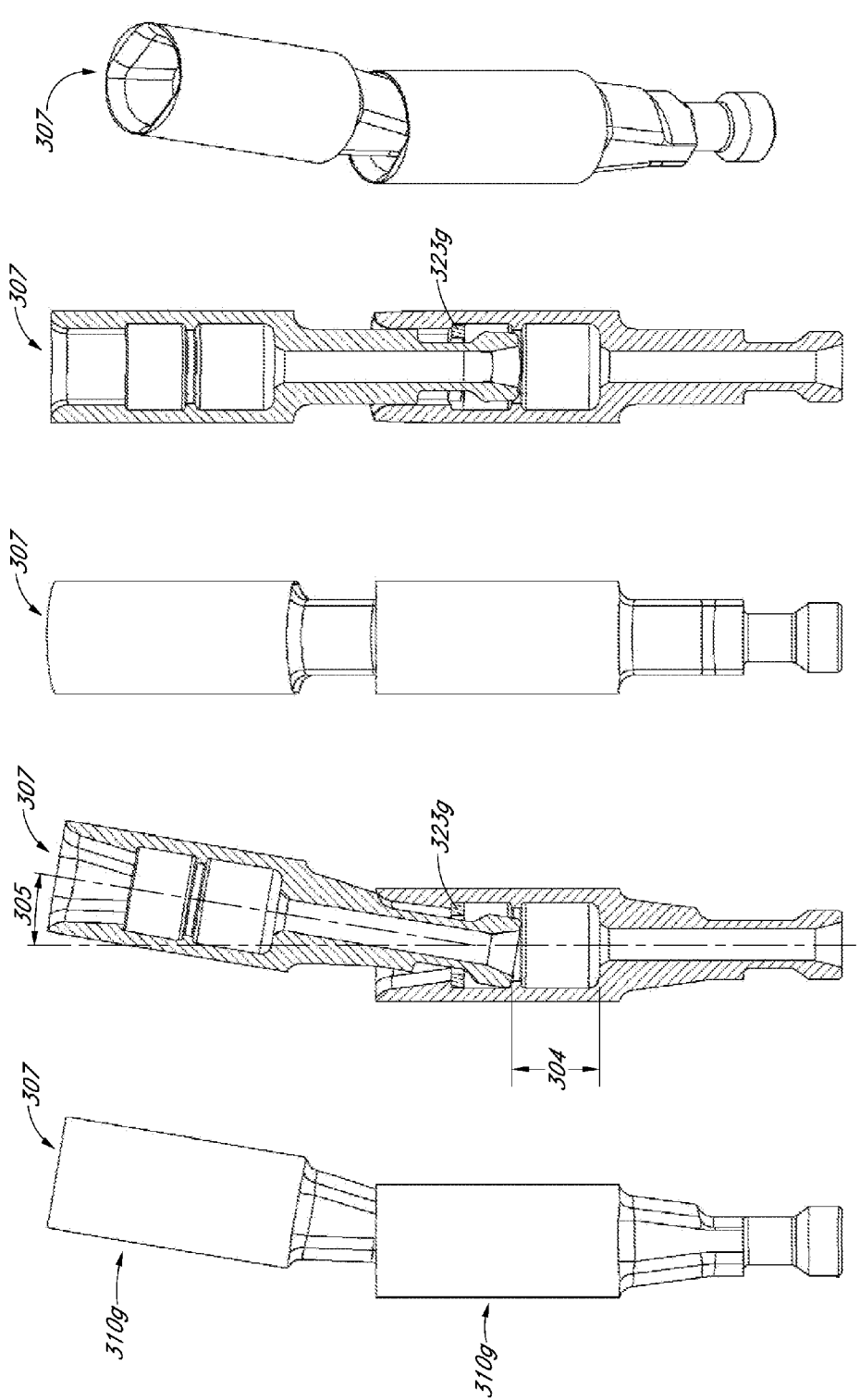

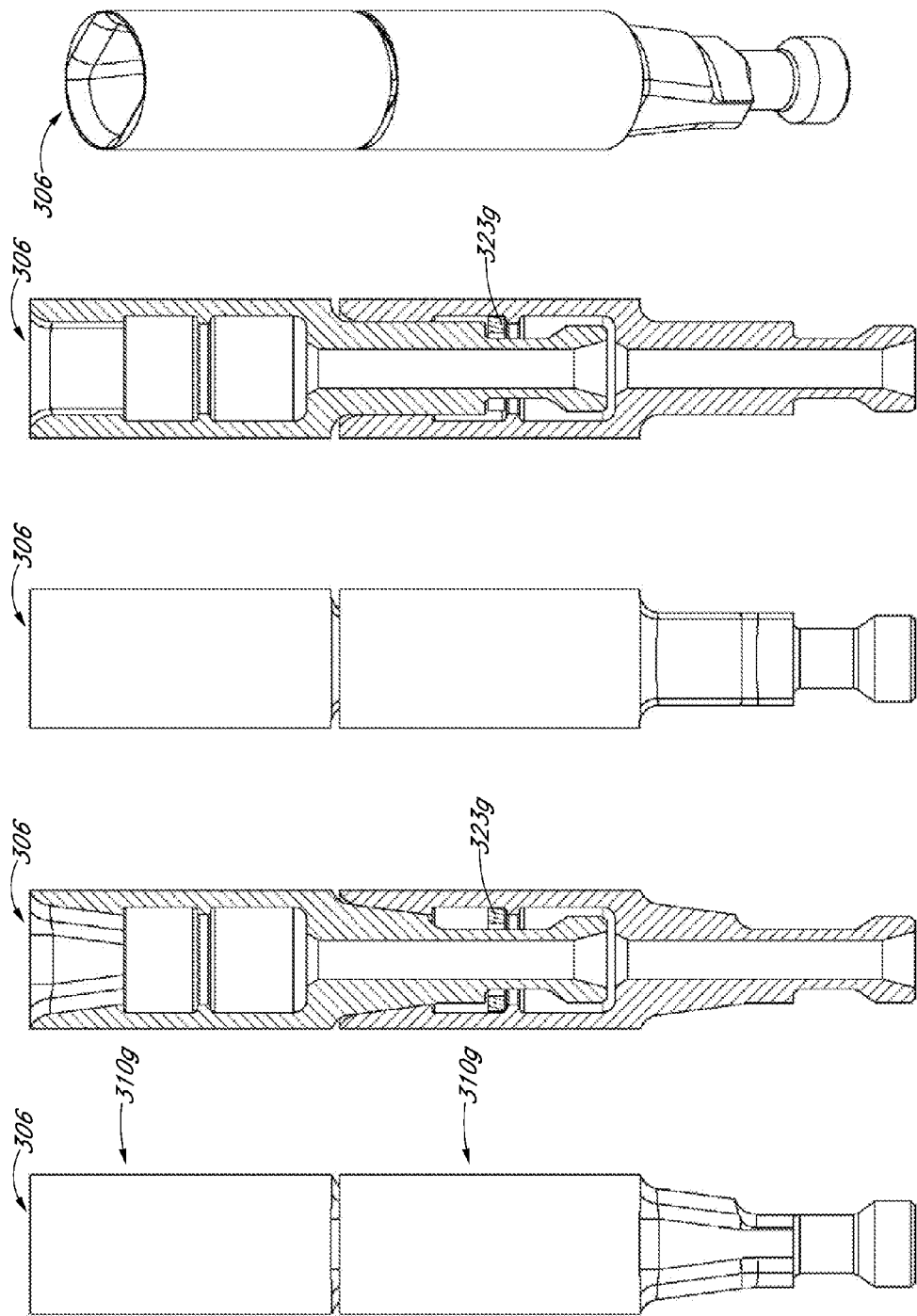

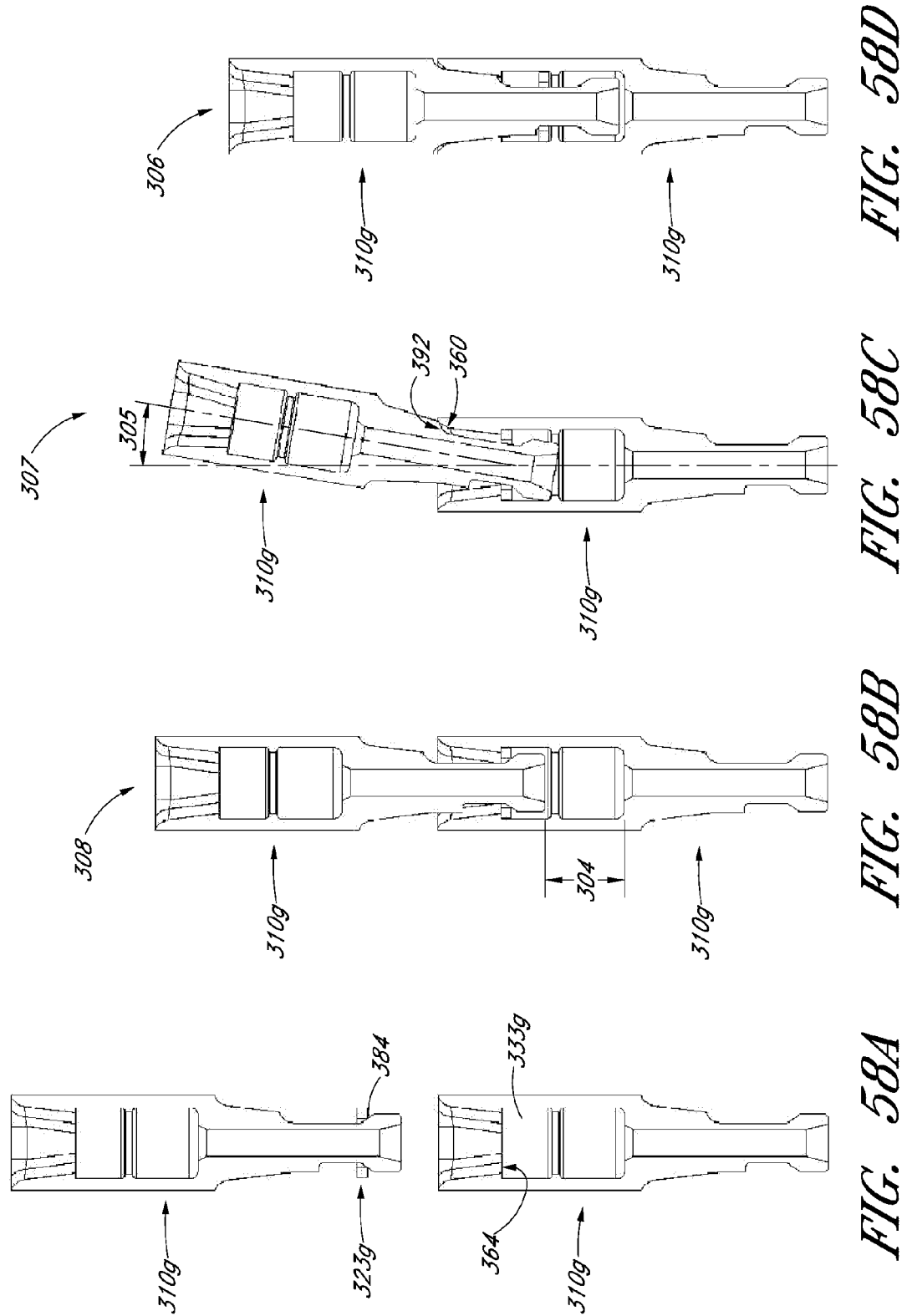

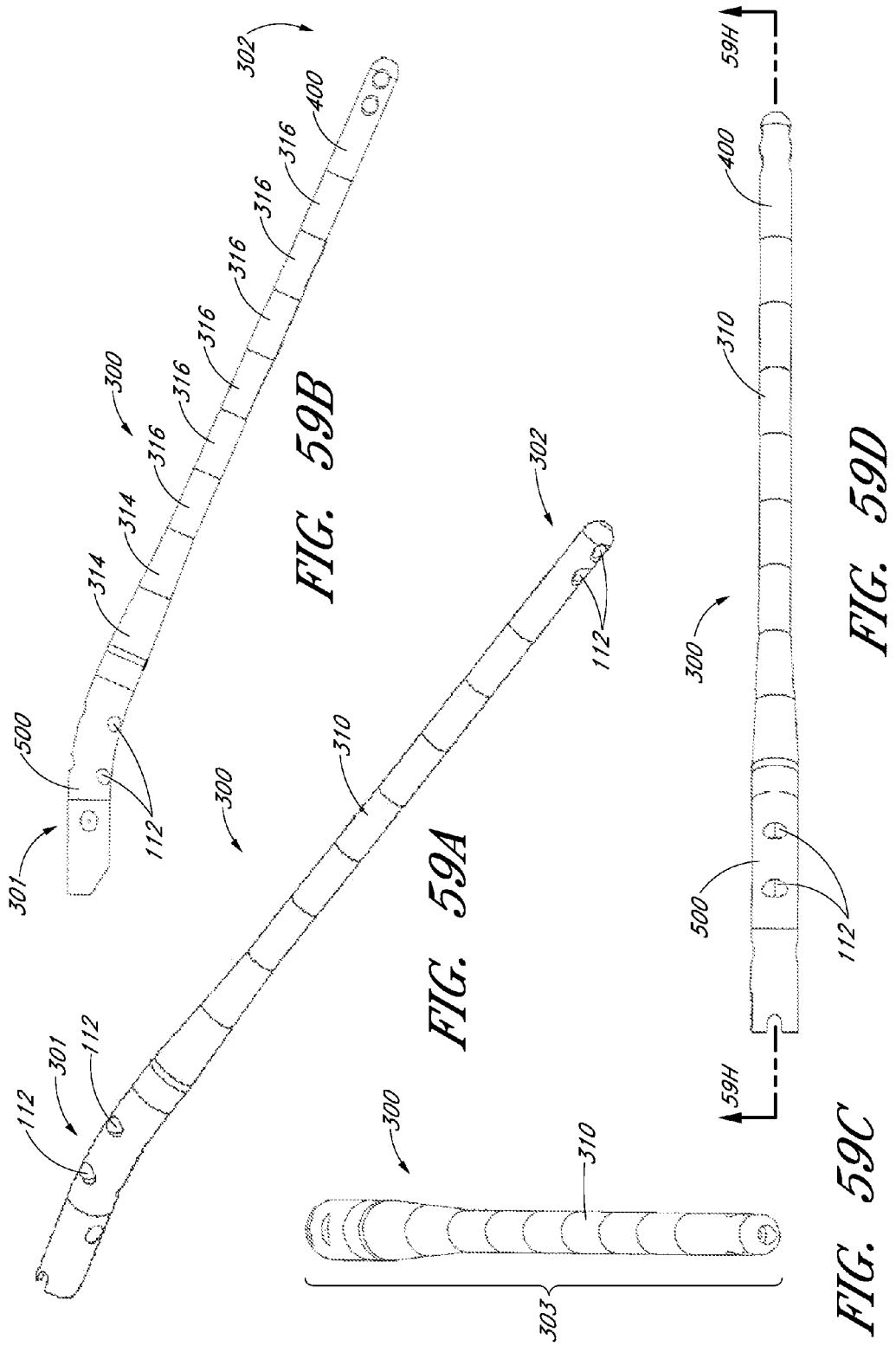

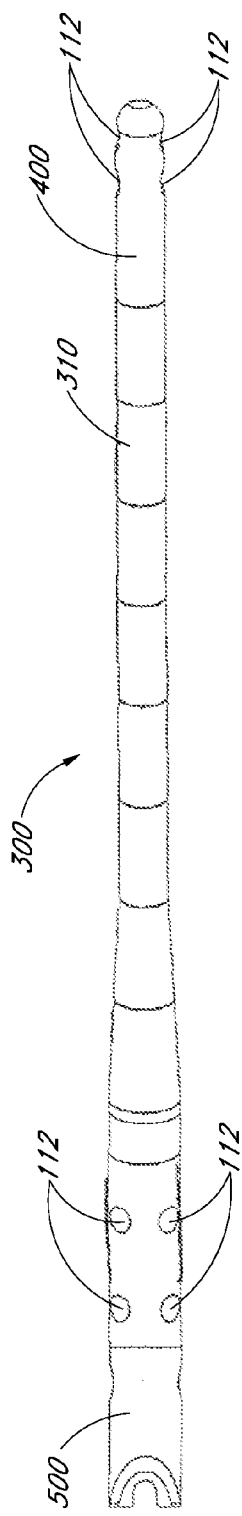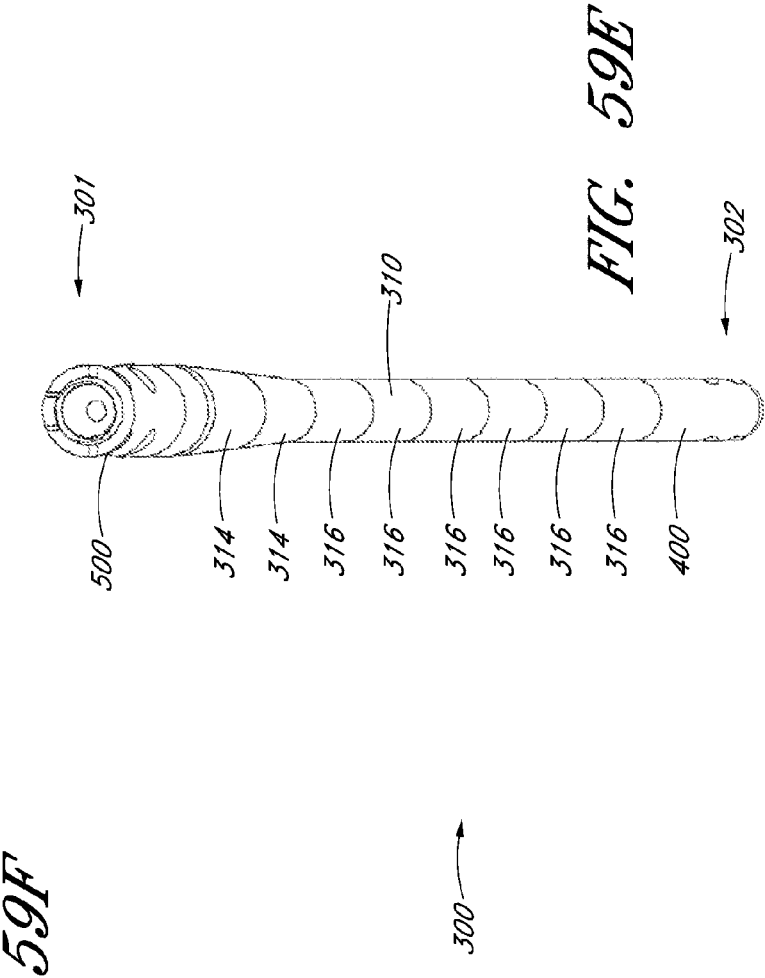
FIG. 59E
FIG. 59F

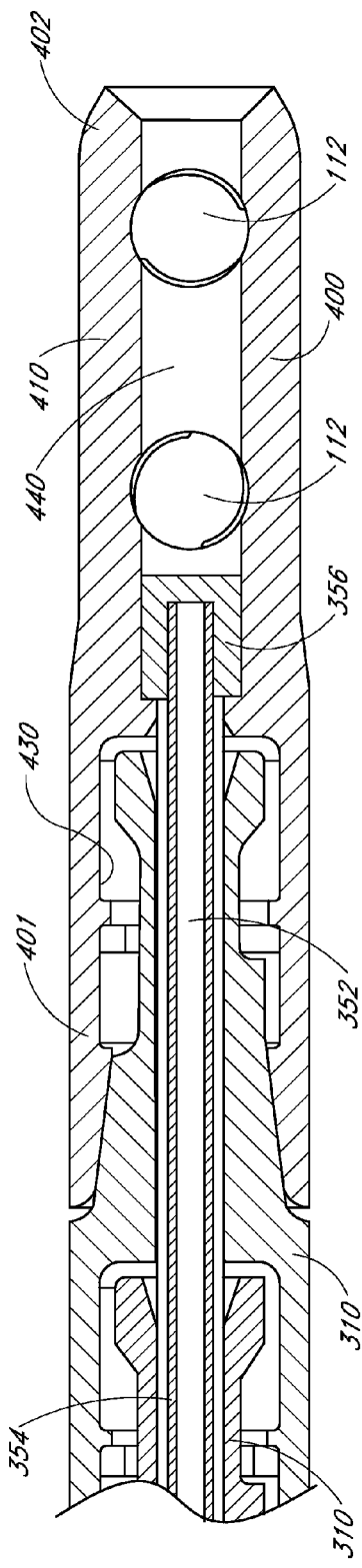
FIG. 64
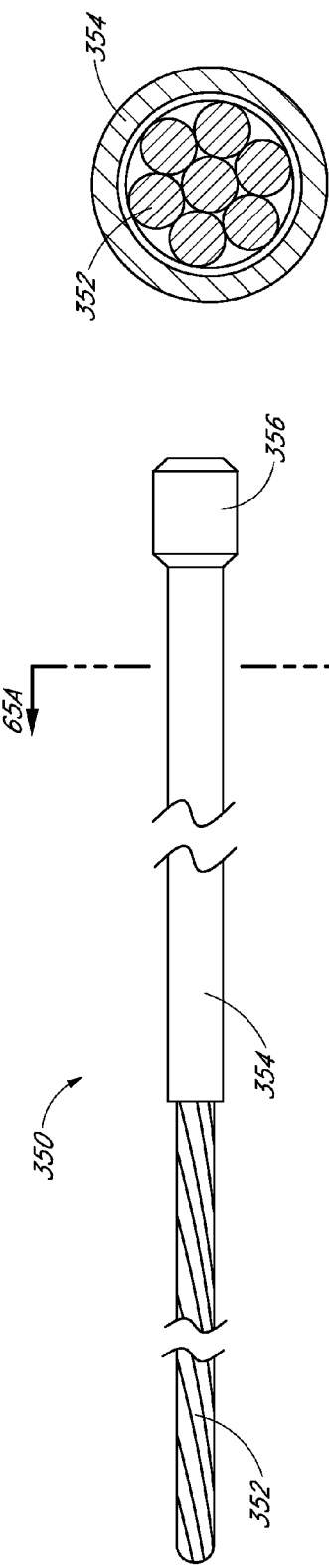
FIG. 65A
FIG. 65

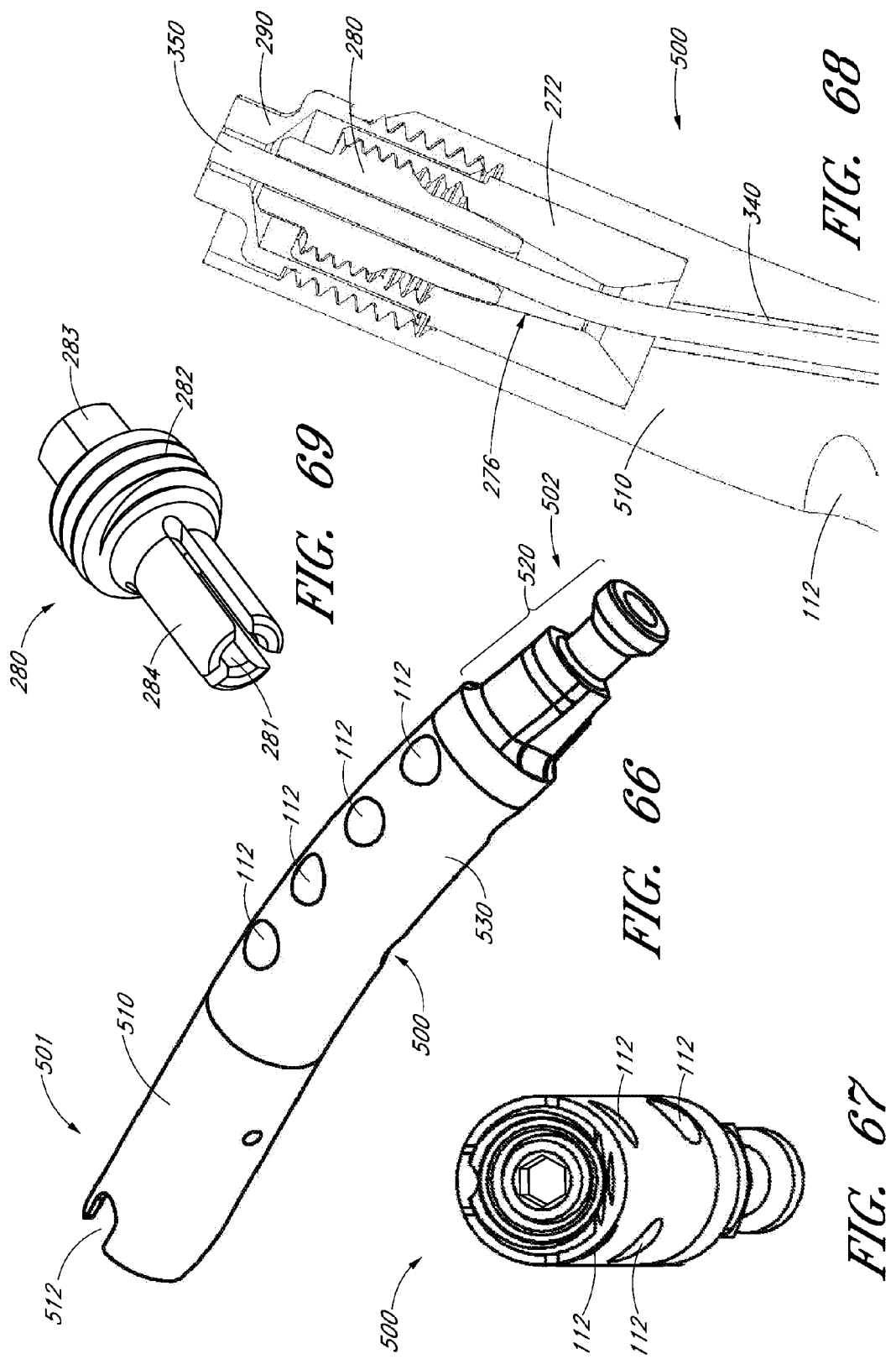

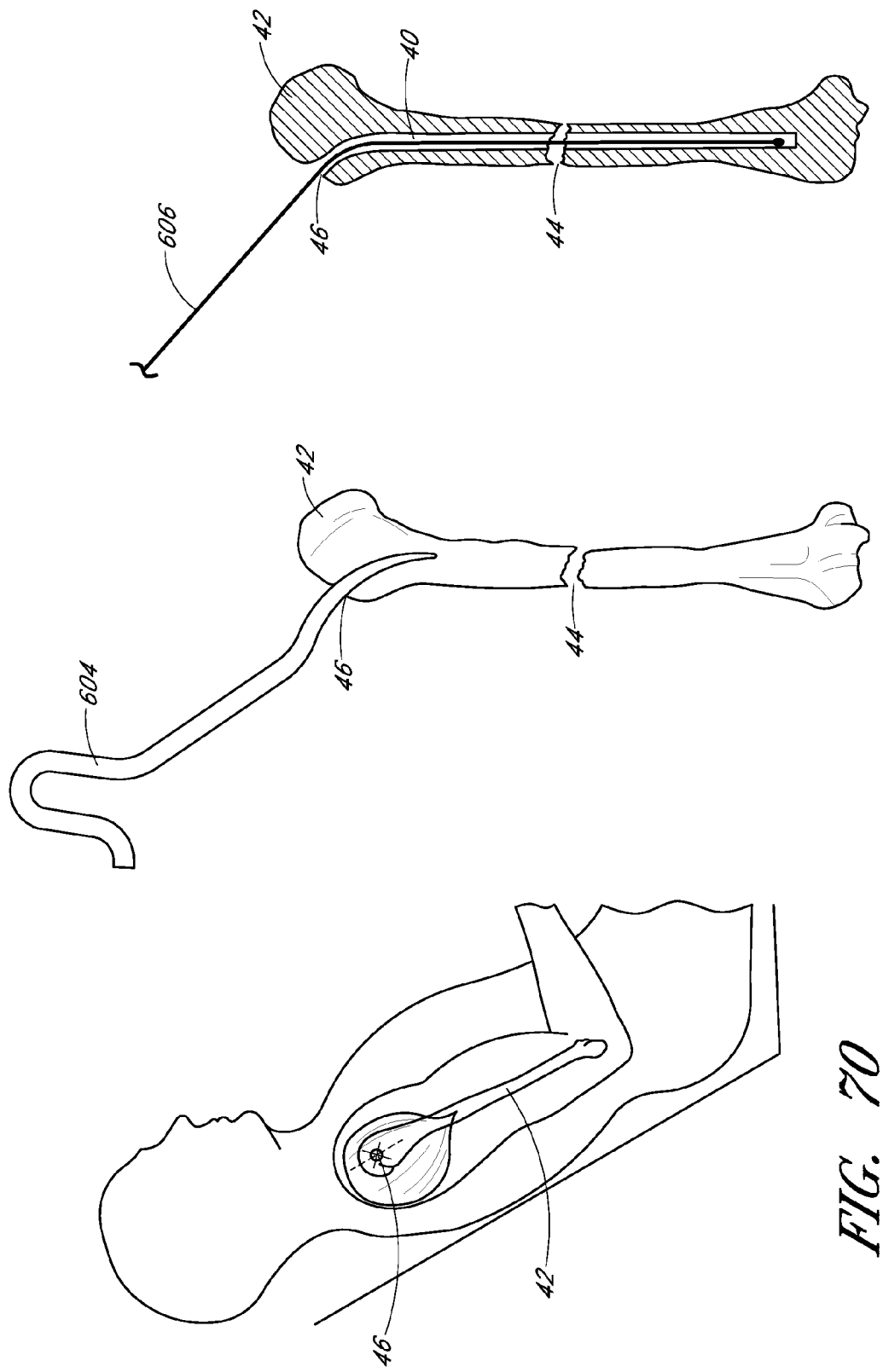

SEGMENTED INTRAMEDULLARY SYSTEM AND APPARATUS

CROSS-REFERENCE TO RELATED APPLICATIONS

This application is a continuation-in-part of U.S. application Ser. No. 12/052,919, filed Mar. 21, 2008, which claims the benefit of priority from U.S. Provisional No. 60/896,342 filed Mar. 22, 2007, all of which are incorporated by reference in their entireties herein.

This application claims the benefit of priority from U.S. Provisional No. 61/055,747, filed May 23, 2008, which is incorporated by reference in its entirety herein.

BACKGROUND

Embodiments of the present invention relate to an orthopedic prosthesis, and, more particularly, to an implantable structure, commonly called an intramedullary or IM nail, that is adapted to be received in the intramedullary canal for the treatment of long bone fractures.

SUMMARY

The intramedullary structure of the present disclosure, in one embodiment, utilizes a plurality of segments that are preferably introduced into the intramedullary canal over a guide member that has been previously introduced into the intramedullary canal through a percutaneous access hole, or access port at an access site. Each segment is preferably configured so that it interconnects with the segments adjacent thereto. In one embodiment an elongated tensioning member is received interiorly of the segments and is secured to the end segments to secure all the segments in the structure together. In one embodiment, the guide member is a wire or cable that can also serve as the tensioning member. In one embodiment each segment may have an aperture, in the form of an open interior, so that the segment can be threaded over a guide or tensioning member. The segments also have opposed ends that preferably are complementarily-shaped so that a first interface of a first segment is adapted to cooperatively engage with a second interface of a second segment adjacent thereto. In one embodiment each segment has a male end portion and a complementarily-shaped female end portion.

In one embodiment an implantable intramedullary fixation structure has a proximal end, a distal end and an elongate body adapted to be received in the intramedullary canal of a long bone. The implantable intramedullary fixation structure includes a plurality of segments, an elongate element and a lock. Each segment has a first interface and a complementarily-shaped second interface such that the first interface of a segment cooperatively engages the second interface of an adjacent segment. Each segment includes a channel. The elongate element extends through the channels to apply a compressive force along the longitudinal axis of the structure. The lock is in at least one of the proximal end and the distal end. The lock is for securing the tension member. Activation of the tensioning member causes the fixation structure to convert from a substantially flexible state to a substantially rigid state. In one embodiment the lock comprises a collet. In one embodiment the rigid state is non-linear. In one embodiment the rigid state conforms to the intramedullary canal. In one embodiment the complementarily-shaped ends of the segments permit relative movement between adjacent segments substantially in a single plane. In one embodiment the adjacent segments are secured to each other. In one embodiment the intramedullary structure also includes a guide for positioning each segment in the intramedullary canal.

In one embodiment an implantable intramedullary fixation device is adapted to be received in the intramedullary canal of a long bone. The implantable intramedullary fixation device includes an elongate body and a plurality of segments for defining the body. The elongate body is transformable between a flexible state for implantation within a bone, and a rigid state for fixing a fracture in a bone. Each segment has a first interface and a complementarily-shaped second interface such that the first interface of a segment cooperatively engages the second interface of an adjacent segment. The segments include a channel so as to be receivable over a guide for positioning in the intramedullary canal. The body is bendable in a single plane within the flexible state. In one embodiment the intramedullary device also includes a tensioning member extending the length thereof to apply a compressive force along the longitudinal axis of the structure. In one embodiment the axial length of the body is reduced as the body is transformed from the flexible state to the rigid state. In one embodiment the axial length of the body is reduced up to about 5 mm. In one embodiment the complementarily-shaped interfaces of the segments comprise friction enhancing surface structures. In one embodiment the adjacent segments are secured to each other. In one embodiment the intramedullary device also includes at least one fastener received in at least one of the segments for securing the device in place in the long bone.

Other features and aspects will become apparent upon reference to the accompanying drawings and description.

BRIEF DESCRIPTION OF THE DRAWINGS

These and other features, embodiments, and advantages of the present invention will now be described in connection with preferred embodiments of the invention, in reference to the accompanying drawings. The illustrated embodiments, however, are merely examples and are not intended to limit the invention.

FIG. 1 is a perspective of an assembled segmented intramedullary structure, such as a nail, according to a first embodiment of the disclosure.

FIG. 2 is a perspective view of a single segment of the intramedullary nail of FIG. 1.

FIG. 3 is a longitudinal cross-sectional view of the segment of FIG. 2.

FIG. 4 is a perspective view of an intramedullary nail utilizing a second embodiment of an individual nail segment.

FIGS. 9 and 10 are perspective views of a fifth embodiment of an individual segment and a plurality of such segments mounted together.

FIGS. 11 and 12 are perspective views of a sixth embodiment of a segment for use in an intramedullary nail in which a plurality of peripheral rods is used in the assembled nail.

FIG. 13 is a perspective of a seventh embodiment of an IM nail in which the segments are connected to each other by a hinge member so that the nail can be inserted into the intramedullary canal through an access hole that is oblique to the axis of the intramedullary canal.

FIGS. 14-22 schematically illustrate the procedure for installing a segmented intramedullary nail according to one embodiment of the present invention into the intramedullary canal of a long bone.

FIG. 47A is a schematic side view of an embodiment of a unidirectional segment of a segmented intramedullary structure.

FIG. 47B is a schematic cross-sectional side view of the unidirectional segment of FIG. 47A.

FIG. 47C is a schematic perspective view of the unidirectional segment of FIG. 47A.

FIG. 48A is a schematic side view of another embodiment of a unidirectional segment of a segmented intramedullary structure.

FIG. 48B is a schematic cross-sectional side view of the unidirectional segment of FIG. 48A.

FIG. 48C is a schematic perspective view of the unidirectional segment of FIG. 48A.

FIG. 49A is a schematic side view of an embodiment of a pair of adjacent unidirectional segments of FIG. 48A in a bent configuration.

FIG. 49B is a schematic transparent cross-sectional side view of the pair of adjacent unidirectional segments of FIG. 48A in a bent configuration.

FIG. 49C is a schematic partial cross-sectional side view of the pair of adjacent unidirectional segments of FIG. 48A in a bent configuration.

FIG. 51A is a schematic side view of an embodiment of a threaded segment of a segmented intramedullary structure.

FIG. 51B is a schematic cross-sectional side view of the threaded segment of FIG. 51A.

FIG. 51C is a schematic perspective view of the threaded segment of FIG. 51A.

FIG. 52A is a schematic side view of another embodiment of a threaded segment of a segmented intramedullary structure.

FIG. 52B is a schematic cross-sectional side view of the threaded segment of FIG. 52A.

FIG. 52C is a schematic perspective view of the threaded segment of FIG. 52A.

FIG. 54A is a schematic side view of an embodiment of a pair of adjacent threaded segments of FIG. 52A in a straightened configuration.

FIG. 54B is a schematic transparent cross-sectional side view of the pair of adjacent threaded segments of FIG. 52A in a straightened configuration.

FIG. 54C is a schematic partial perspective side view of the pair of adjacent threaded segments of FIG. 52A in a straightened configuration.

FIG. 55A is a schematic side view of an embodiment of a snap ring segment of a segmented intramedullary structure.

FIG. 55B is a schematic cross-sectional side view of the snap ring segment of FIG. 55A.

FIG. 55C is a schematic front view of the snap ring segment of FIG. 55A.

FIG. 55D is a schematic cross-sectional front view of the snap ring segment of FIG. 55A.

FIG. 55E is a schematic perspective view of the snap ring segment of FIG. 55A.

FIG. 56A is a schematic side view of an embodiment of a pair of adjacent snap ring segments of FIG. 55A in a bent configuration.

FIG. 56B is a schematic cross-sectional side view of the pair of adjacent snap ring segments of FIG. 55A in a bent configuration.

FIG. 56C is a schematic front view of the pair of adjacent snap ring segments of FIG. 55A in a bent configuration.

FIG. 56D is a schematic cross-sectional front view of the pair of adjacent snap ring segments of FIG. 55A in a bent configuration.

FIG. 56E is a schematic perspective view of the pair of adjacent snap ring segments of FIG. 55A in a bent configuration.

FIG. 57A is a schematic side view of an embodiment of a pair of adjacent snap ring segments of FIG. 55A in a straightened, compressed configuration.

FIG. 57B is a schematic cross-sectional view of the pair of adjacent snap ring segments of FIG. 55A in a straightened configuration.

FIG. 57C is a schematic front view of the pair of adjacent snap ring segments of FIG. 55A in a straightened configuration.

FIG. 57D is a schematic cross-sectional front view of the pair of adjacent snap ring segments of FIG. 55A in a straightened configuration.

FIG. 57E is a schematic perspective view of the pair of adjacent snap ring segments of FIG. 55A in a straightened configuration.

FIG. 58A is a schematic side view of an embodiment of a pair of adjacent segments in a detached configuration in one embodiment of a segmented intramedullary structure.

FIG. 58B is a schematic side view of the pair of adjacent segments of FIG. 58A in a distracted configuration with an axial displacement length between the adjacent segments.

FIG. 58C is a schematic side view of the pair of adjacent segments of FIG. 58A in a bent configuration with a rotational displacement angle between the adjacent segments.

FIG. 58D is a schematic side view of the pair of adjacent segments of FIG. 58A in a compressed configuration.

FIG. 59A is a schematic perspective view of an embodiment of a segmented intramedullary structure in a compressed configuration.

FIG. 59B is a schematic side view of the segmented intramedullary structure of FIG. 59A.

FIG. 59C is a schematic front view of the segmented intramedullary structure of FIG. 59A.

FIG. 59D is a schematic top view of the segmented intramedullary structure of FIG. 59A.

FIG. 59E is a schematic rear view of the segmented intramedullary structure of FIG. 59A.

FIG. 59F is a schematic bottom view of the segmented intramedullary structure of FIG. 59A.

FIG. 64 is a schematic cross sectional side view of the cross-screw distal fixation structure segment of an intramedullary structure of FIG. 61.

FIG. 65 is a schematic side view of a cable and cable tube according to one embodiment of the present invention.

FIG. 65A is a schematic cross sectional view of the cable and the cable tube according to FIG. 65.

FIG. 66 is a schematic perspective view of an embodiment of a proximal end segment.

FIG. 67 is a schematic top view of the proximal end segment of FIG. 66.

FIG. 68 is a schematic cross sectional side view of the proximal end segment of FIG. 66.

FIG. 69 is a schematic perspective view of a cable collet anchor according to one embodiment of the present invention.

FIG. 70 is a schematic side view of a surgical procedure in a bone according to an embodiment of the present invention.

FIG. 71 is a schematic side view of a surgical procedure in a bone with a broach according to an embodiment of the present invention.

FIG. 72 is a schematic side view of a surgical procedure in a bone with a guide wire according to an embodiment of the present invention.

FIG. 76 is a schematic side view of a segmented intramedullary structure being inserted in a bent configuration in to a sectional view of a bone according to an embodiment of the present invention.

FIG. 77 is a schematic side view of a surgical procedure in a bone with a segmented intramedullary structure being inserted in a bent configuration in to a sectional view of a bone with a proximal drill guide according to an embodiment of the present invention.

FIG. 78 is a schematic side view of a surgical procedure in a bone with a tensioner and a segmented intramedullary structure according to an embodiment of the present invention.

FIG. 79 is a schematic side view of a modular, customizable segmented intramedullary structure according to an embodiment of the present invention.

Figure 5:
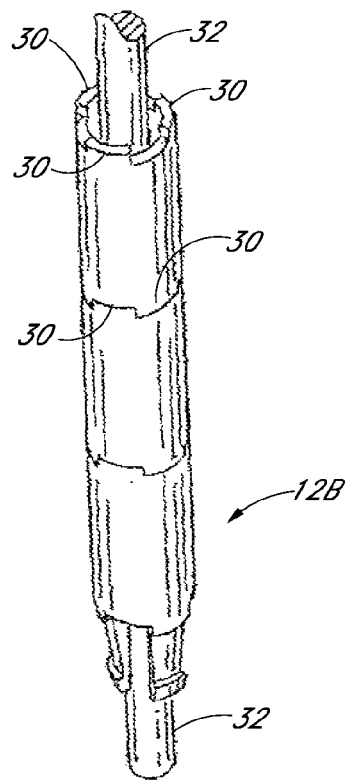
FIGS. 5 and 6 are perspective views of a third embodiment of an individual segment for use in an intramedullary structure and a plurality of such segments received over a guide member.

Throughout the figures, the same reference numerals and characters, unless otherwise stated, are used to denote like features, elements, components or portions of the illustrated embodiments. In certain instances, similar names may be used to describe similar components with different reference numerals which have certain common or similar features. Moreover, while the subject invention will now be described in detail with reference to the figures, it is done so in connection with the illustrative embodiments. It is intended that changes and modifications can be made to the described embodiments without departing from the true scope and spirit of the subject invention as defined by the appended claims.

DETAILED DESCRIPTION

In accordance with the present disclosure, various embodiments of an intramedullary structure are provided that are adapted to be received in the intramedullary canal of a bone, such as a long bone, including but not limited to a humerus, tibia, femur, radius, ulna, phalange, metatarsal, metacarpal, clavicle or other long bone. In various embodiments the structure comprises a plurality of segments, with complementary interfaces between the segments. In various embodiment the complementary interfaces can comprise complementary surfaces, complimentarily-shaped features, mating male and female portions, nested features, paired geometries, and the like which can interface a proximal, medial, intermediate, middle, or distal portion, area, or end of the respective segments. In one embodiment a segment has a first interface and a complementarily-shaped second end interface, so that the first interface of a segment cooperatively engages the second interface of an adjacent segment.

In various embodiments the segments can define a channel, aperture or lumen so as to be receivable over an elongate member for introduction of the segments into the intramedullary canal. In various embodiments, the elongate member can be a wire, guide wire, pull wire, push wire, cable, rod, threaded rod, or other similar structure. Use of terms related to embodiments of elongate members may be used interchangeably and should be understood to refer to the various types of embodiments of the elongate member being used. For example, cable may be used to describe any number of types of elongate members, but should not be necessarily limited to use only with a cable. For example, a cable tensioner tool can be understood to refer to other possible embodiments of elongate member tensioner tools. In one embodiment the elongate member is a tensioning member extending along the length of the segmented intramedullary structure that cooperates with the two or more segments, such as in one embodiment the end-most segments, of the structure to apply a compressive force along the longitudinal axis of the structure, thus providing the structure with enhanced rigidity. In one embodiment the compressive force for enhancing rigidity also provides secondary compression to the surrounding bone segments by brining bone segments closer together.

In various embodiments, different combinations of segments can be used or combined in a modular fashion to assemble custom made structures based on the bone and application for the structure. In some embodiments the intramedullary structure is removable from the body. In various embodiments the overall configuration or shape of the intramedullary structure may be straight, substantially straight, or curved along any one segment or any sets of segments. Each segment can be substantially straight or curved, and any set of straight segments can have interfaces providing for angles between adjacent segments. In one embodiment the intramedullary structure has a first configuration and a second configuration. In one embodiment the first configuration is substantially the configuration of the intramedullary structure once it is assembled and delivered into the intramedullary canal. In one embodiment the second configuration is the configuration of the intramedullary structure once it is locked. In one embodiment an intramedullary structure configuration is linear. In one embodiment an intramedullary structure configuration is substantially linear. In one embodiment an intramedullary structure configuration is curved. In one embodiment an intramedullary structure configuration is predetermined. In one embodiment a predetermined configuration mimics the contour of the intramedullary canal. In one embodiment an intramedullary structure configuration is governed by the native structure of the intramedullary canal in which the structure is inserted. In one embodiment an intramedullary structure configuration conforms to the structure of the surrounding tissue. In one embodiment an intramedullary structure configuration is flexible. In one embodiment an intramedullary structure configuration is substantially rigid. In one embodiment an intramedullary structure configuration is rigid. In one embodiment an intramedullary structure can change from a relatively longer configuration to a relatively shorter configuration. In one embodiment an intramedullary structure configuration is movable within one plane. In one embodiment an intramedullary structure configuration is movable in two planes. In one embodiment an intramedullary structure configuration is movable in three or more planes. In one embodiment an intramedullary structure configuration is axially compressible. In one embodiment an intramedullary structure configuration is rotatable about a longitudinal axis. In one embodiment an intramedullary structure configuration is axially rotatable. In one embodiment an intramedullary structure configuration is locked.

Turning to FIG. 1, a first embodiment of a segmented intramedullary structure 10 is shown. The illustrated embodiment of the segmented intramedullary structure 10 comprises eight segments 12 that are received over an optional tension rod 14 to provide an intramedullary structure 10 having an overall length of approximately 175 mm. Of course, the number of segments 12 and the overall length and other geometric measurements, including but not limited to diameter, curvature, fixation structures, and other features of the segmented intramedullary structure 10 can vary depending on the size and type of bone, and can depend upon the length of the intramedullary canal into which it is to be inserted, as well as any features the medical practitioner elects is preferred for a particular use.

As shown, in one embodiment the ends 16 of the tension rod 14 are threaded and the segments 12 are maintained thereon by complementarily threaded members (nuts 18 and washers 20 are shown) received on the threaded ends 16 of the tension rod 14. However, alternate methods for securing the segments 12 to the tension rod 14 may be employed, such as a swage fitting that is received on the tension rod and which seats in the open interior of the end segments, or a press nut received on the tension rod in engagement with the end segments.

FIGS. 2 and 3 show one embodiment of a single segment 12 of the intramedullary structure shown in FIG. 1. The specific configuration of the individual segment 12 shown in FIGS. 2 and 3 is by way of example only. In one embodiment the segment 12 comprises a male end 22 having a frusto-conical outer shape and a female end 24 having a cylindrical outer shape and a frusto-conical inner shape complementarily to the outer shape of the male end 22.

In one embodiment, the overall length of the segment 12 is preferably no greater than about 32 mm, which allows the segment 12 to be relatively easily introduced into the intramedullary canal through a 10 mm percutaneous access hole that is oriented at approximately 30 degrees with respect to the bone axis. The largest outside diameter of the segment 12 is dictated by the inside diameter of the intramedullary canal. In one embodiment the largest outer diameter of the segment 12 is about 9 mm. In one embodiment the inside diameter of the male end 22 of the segment is approximately 3.6 mm, which allows a 3 mm guide wire or cable to easily pass there through.

In one embodiment components of the implant are made of a biocompatible material of sufficient rigidity and strength, such as Titanium. In one embodiment the implant comprises materials made of a Titanium Alloy. In one embodiment the implant comprises material made of Ti-6Al-4V alloy. In one embodiment the segments 12 are made of a biocompatible material of sufficient rigidity and strength, such as Titanium or its alloys. In one embodiment the inside surface of the female end 24 and the outside surface of the male end 22 may be smooth ("mirror polished") to facilitate nesting. In one embodiment the outside surface of the female end 24 may be roughened or textured ("knurled") to promote tissue growth thereon. In various embodiments, various coatings may be applied to part or all of the external and/or internal surfaces of the segments. In one embodiment, segments can be anodized. In one embodiment, anodizing segment surfaces can reduce the likelihood of cold fusion from binding parts under compression together.

In the illustrated embodiment, adjacent segments 12 are secured to each other by a friction fit between the inside surface of the female end and the outside surface of the male end. However, a more positive interlocking can be obtained, if desired, by providing the segments with mechanically-interlocking structures, such as slots and pins, prongs, tabs, screw threads, etc. The segments may also be configured to prevent rotational movement there between when assembled. This may be accomplished by, e.g., providing the outer surface of the male end and the inner surface of the female end with complementary non-circular cross sections, such as a square with rounded-off corners. Alternatively, or additionally, bone cement or other hardenable surgical fluid may be introduced into the interior of the segments once in place in the intramedullary canal, to impart additional structural integrity for the assembly and to help secure the assembled structure in place.

FIG. 4 illustrates an embodiment of an intramedullary structure in accordance with the present disclosure utilizing a second embodiment of individual segments 12A. The male end 22A of the segments 12A comprise an externally-threaded standoff that is received in the complementary internally threaded female end 24A of an adjacent segment 12A.

Figure 6:
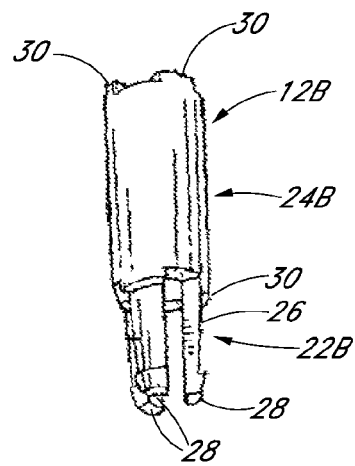

FIGS. 5 and 6 disclose a third embodiment of segments 12B for an intramedullary structure in accordance with the present disclosure. The male ends 22B of the segments comprise prongs 26 with shoulders or detents 28 on their distal ends that provide for a snap fit with the complementarily-shaped end 24B of the adjacent segment 12B. A series of interfitting spaced tabs 30 on the periphery of both the male and female ends provides for alignment of the segments and serve to prevent rotation of the segments 12B with respect to each other. When introduced into the intramedullary canal, the segments are preferably received over a rod or guidewire 32 to facilitate their mating engagement.

Figure 7:
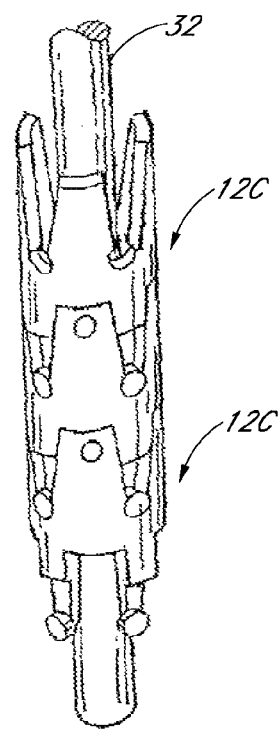
FIGS. 7 and 8 are perspective views of a fourth embodiment of an individual segment and a plurality of such structures received over a guide member.
Figure 8:
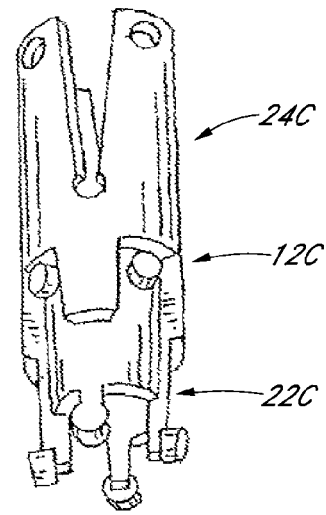

FIGS. 7 and 8 disclose a fourth embodiment of segments 12C for use in an intramedullary structure that is similar to the embodiments of FIGS. 4 and 5. However, the segments 12C have a more elaborate interlocking configuration of the tabs, prongs and detents.

FIGS. 9 and 10 illustrate a fifth embodiment of segments 12D for an intramedullary structure in accordance with the present disclosure. The male end 22D of the segment presents a plurality of longitudinal splines that provide a cross-section similar in appearance to a gear. The female end 24D has a complementarily gear shape and includes a concentric ring 34 that provides a close fit with the inside diameter of the male end 22D. As can be appreciated, this configuration also provides for interfitting segments that are not rotatable with respect to each other.

FIGS. 11 and 12 illustrate a sixth embodiment of segments 12E for use in an intramedullary structure according to the present disclosure. In one embodiment the segments 12E are generally cylindrical in configuration with complementary interfitting tabs 30E on their male and female ends 22E, 24E. The segments 12E also contain a number of spaced, longitudinal throughbores 36 in the walls of the segments (four such throughbores 36 are shown in FIGS. 11 and 12). In one embodiment the throughbores 36 receive elongated peripheral rods 38 that provide the assembled intramedullary structure with additional rigidity and strength. In one embodiment the throughbores 36 receive guide wires or guide mechanisms to help direct a distal end of the intramedullary structure during insertion.

With reference to FIG. 13, a further embodiment of a segmented intramedullary structure 10 is shown. In one embodiment the segmented intramedullary structure 10 is a hinged structure 62. The hinged structure 62 comprises a plurality of segments 64 that are joined to each other by a hinge member 66. The hinge member 66 permits the segments 64 to pivot with respect to each other to facilitate introduction of the structure into the intramedullary nail through an angled access hole.

In various embodiments segmented intramedullary structures 10 can be bent into a curvature for insertion into an access hole to avoid damaging articulating surfaces, joints, or other tissue structures at or near the ends of a long bone. Instead of introducing a rigid nail, embodiments of the segmented intramedullary structures can be inserted in less-invasive access points, which can result in less tissue damage and an easier surgical process for insertion or removal of the intramedullary structure. The various curvatures that are contemplated can vary depending on the type of bone being repaired, but can vary depending on size of the bone, tissue anatomy around the access site, retrograde access, antegrade access, and other potential considerations. For one non-limiting example, an access curvature of the intramedullary structure configured for a humerus can be roughly 80 mm, in the general range of 60-100 mm, and/or in the general range of 20-200 mm. For other bones, the curvature can be larger or smaller, again depending on factors such as bone size. As shown in FIG. 13 one embodiment of the intramedullary structure 10 is made of a single cylindrical member with the V-shaped notches cut out at regular intervals along the length of the structure 62, the material from which the cylindrical member is made providing a "living hinge" between the adjacent segments at the apex of each notch. In one embodiment, once the intramedullary structure 10 is inserted into the intramedullary canal, bone cement is introduced to keep the intramedullary structure straight and provide further structural integrity.

FIGS. 14-22 schematically illustrate the insertion of an embodiment of a segmented intramedullary structure 10 into the intramedullary canal 40 of a long bone 42. In one non-limiting embodiment the long bone 42 is a humerus. In another non-limiting embodiment the long bone is a tibia. In other embodiments, the long bone 42 can be any long bone, such as but not limited to a radius, ulna, femur, fibula, phalange, or other bone.

Figure 14:
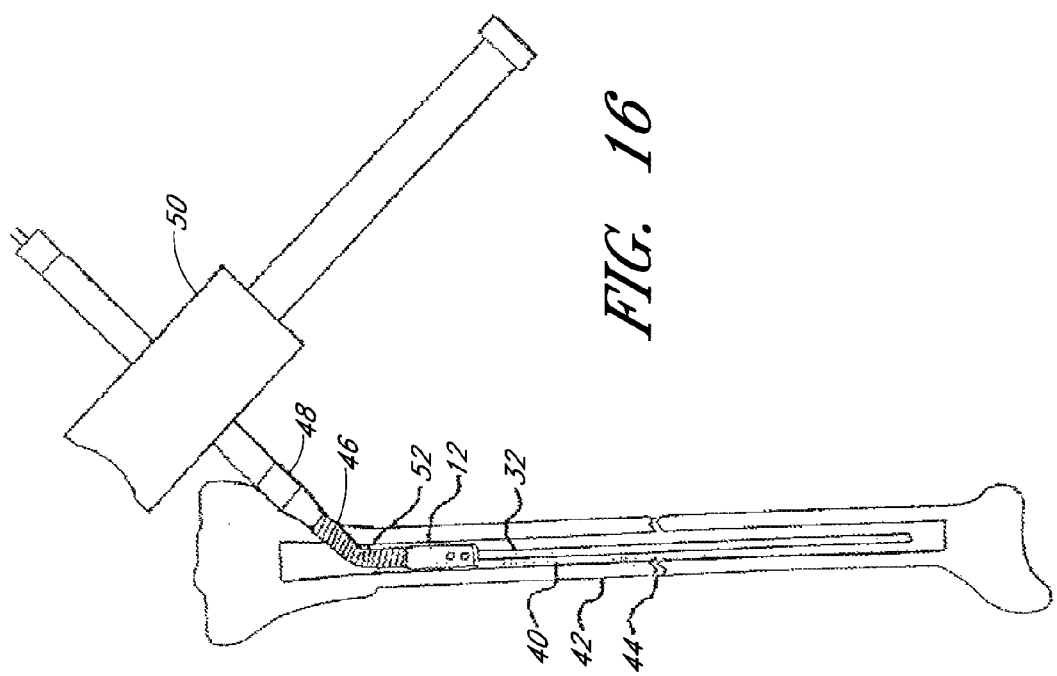

With reference to FIG. 14, a long bone 42 is shown having a fracture 44 intermediate it's proximal and distal ends or regions. In one embodiment an access hole 46 is percutaneously made into the intramedullary canal 40 at the proximal end of the intramedullary canal 40 at an angle oblique to the axis or centerline of the long bone, and preferably at an angle of approximately 30 degrees with respect to the axis of the long bone. In other embodiments the angle can be in the range of 10-90 degrees with respect to the longitudinal axis of the long bone. In various embodiments an access hole 46 can be made in the proximal end, proximal region, intermediate region, distal region, or distal end of the intramedullary canal 40. In one embodiment an access hole 46 can be made for retrograde insertion of a segmented intramedullary structure 10 into the bone. The access hole 46 is of a diameter to accommodate the introduction of the individual segments 12 that comprise the intramedullary structure. In one embodiment the access hole 46 is approximately 10 mm in diameter, but other diameters are contemplated depending on the size of the embodiment of the intramedullary structure being used. In one embodiment, after the access hole 46 is made, a guide wire or cable 32 is inserted there through and advanced into the intramedullary canal 40 and across the fracture site 44 to the distal end of the intramedullary canal 40.

Figure 15:
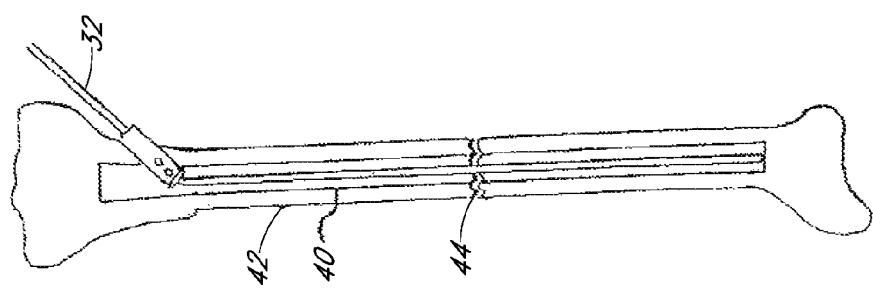
Figure 16:
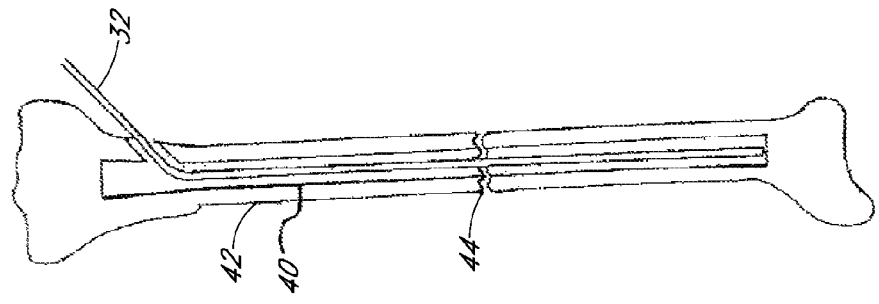

Turning to FIG. 15, a second step of one embodiment is shown in which a first or distal-most segment 12 is threaded over the guidewire and advanced through the percutaneous access hole 46 into the intramedullary canal 40. In one embodiment as shown in FIG. 16, the segment 12 is forced through the access hole 46 and advanced along the guidewire 32 by means of an inserter 48 that also fits over the guidewire 32. The inserter 48 has a slotted hammer 50 associated therewith to impart additional force to the segment 12 as it is advanced into the intramedullary canal 40.

Figures 17, 18, 19:
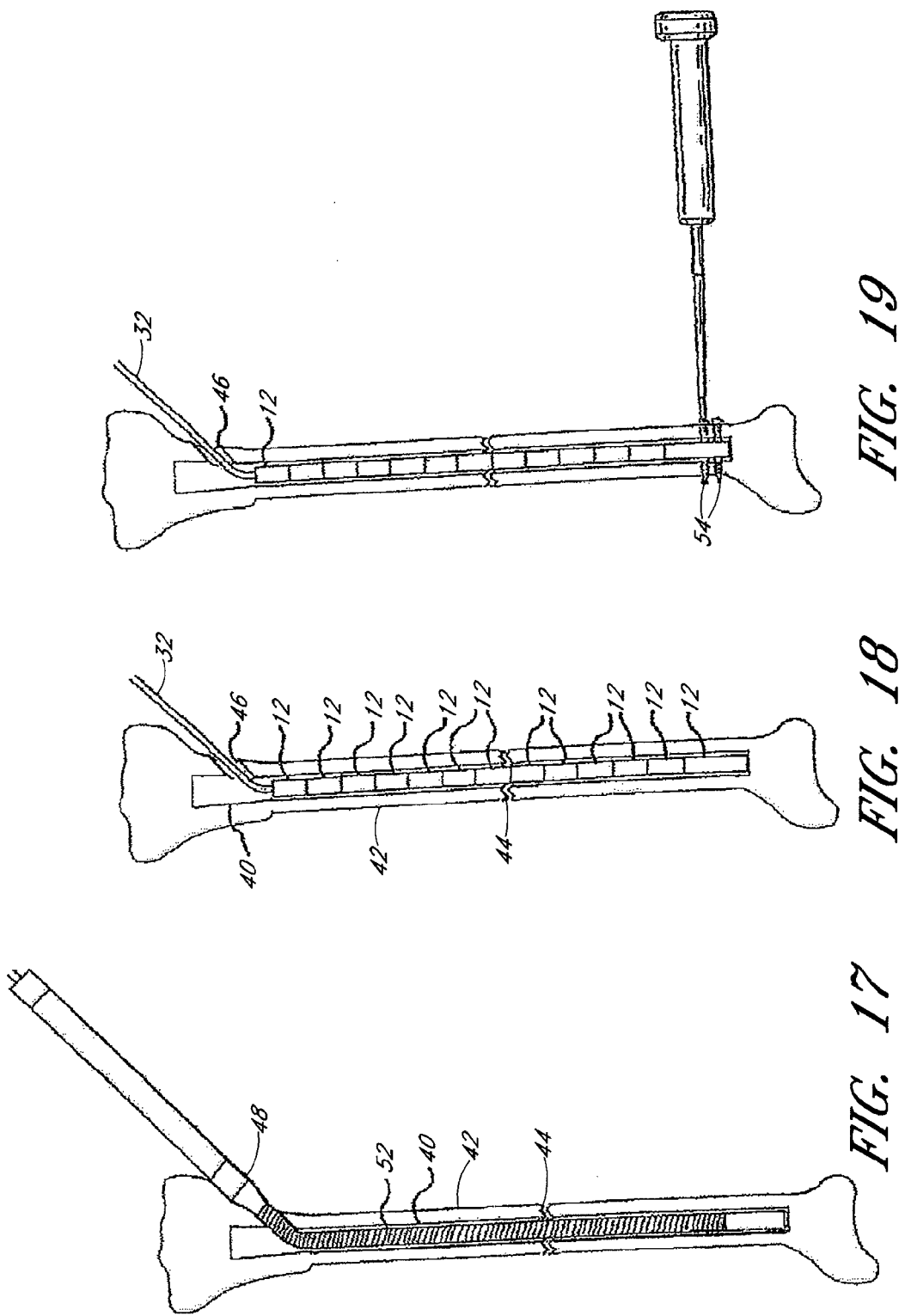
Figure 23:
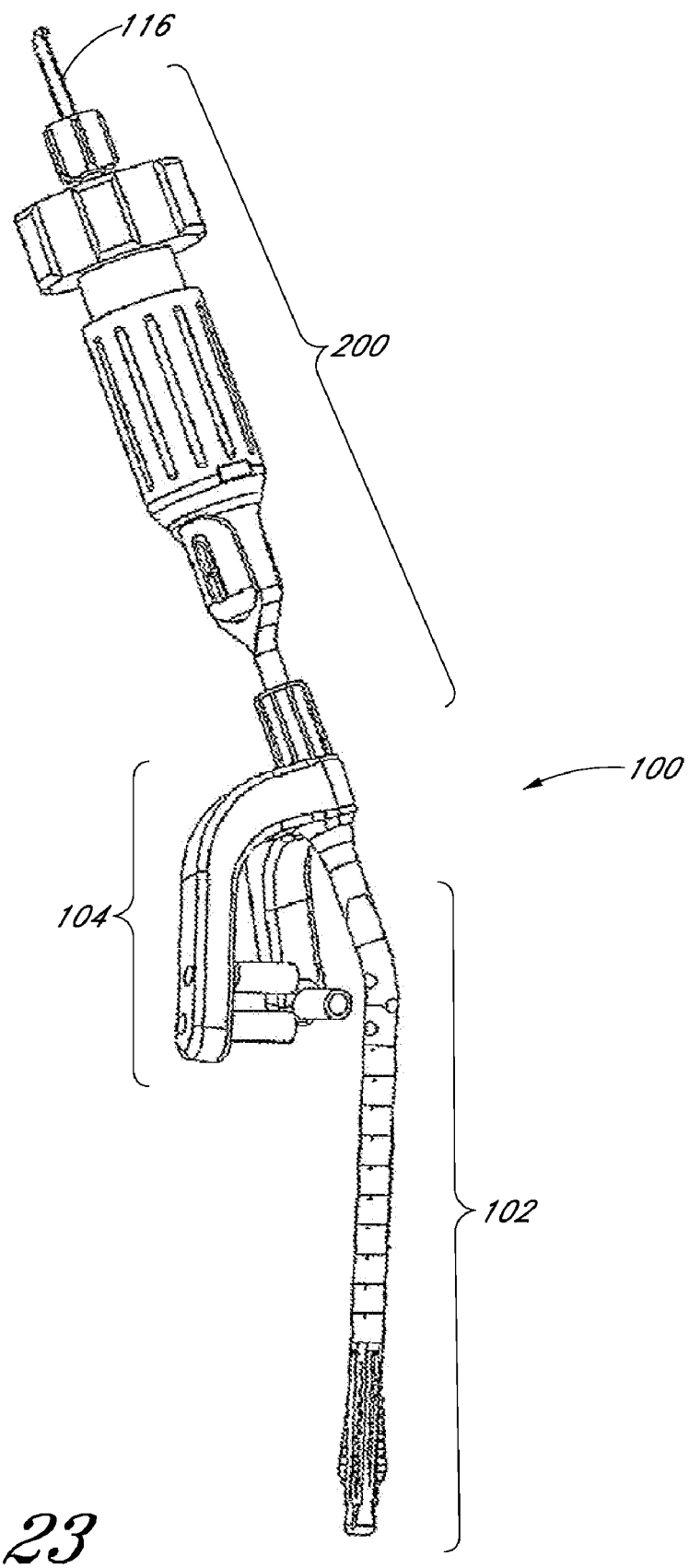
FIG. 23 is a perspective view of a system for implanting an intramedullary fracture fixation device comprising the implantable fracture fixation device, a screw guide, and a cable tensioner according to one embodiment of the present invention.

In one embodiment as reflected in reference to FIG. 17, once the segment 12 is positioned within the intramedullary canal 40, it is advanced along the guidewire 32 to the distal end of the IM canal 40 using a flexible push rod 52. The steps of inserting a segment 12 over the guidewire and advancing it distally along the guidewire, shown in FIGS. 15-17, can be repeated until an intramedullary structure of the desired length is created. With reference to the embodiment illustrated in FIG. 18, the segmented intramedullary structure 10 has thirteen segments. Therefore the steps of FIGS. 15-17 are repeated twelve times. Other numbers of segments can be used. In one embodiment the doctor can add or subtract one or more segments during the insertion process. Modifications to the overall segment structure can be made and changed during, or in the midst of a device implantation.

With reference to FIG. 19, in one embodiment the segmented intramedullary structure 10 is secured to the distal end of the IM canal. In one embodiment the distal-most and proximal-most segments include one or more throughbores for receiving bone screws, or locking bolts 54. In one embodiment locking bolts 54 are introduced percutaneously and are advanced through bores in the distal-most and proximal-most segments, using fluoroscopy for guidance. In the illustrated method, the guidewire 32 is left in place. However, if the segments comprising the IM nail positively interlock, the guidewire 32 may be removed after all the segments comprising the IM nail are interconnected. With reference to FIG. 20, a locking nut 56 is inserted over the guidewire 32 and into the proximal-most segment, a flexible driver 58 being used to tighten the nut 56 to a prescribed torque. In one embodiment the exposed portion of the guidewire 32 is then cut off (see FIG. 21) and in one embodiment percutaneous locking bolts 60 are used to secure the proximal-most segment in place (see FIG. 22). Means other than locking bolts, fixation screws, or other fasteners may be used to secure the intramedullary structure in place in the intramedullary canal, including but not limited to a bone cement or other hardenable surgical fluid, or radially expandable elements.

With reference to FIGS. 23-38, a further embodiment of a segmented intramedullary system, generally designated 100, is disclosed. The system 100 comprises three basic components: an implantable segmented intramedullary fracture fixation device structure 102 (which can be the same or similar to any embodiment of a segmented intramedullary structure 10), a proximal fixation screw guide-interface 104, and a cable tensioner assembly 200.

Figure 24:
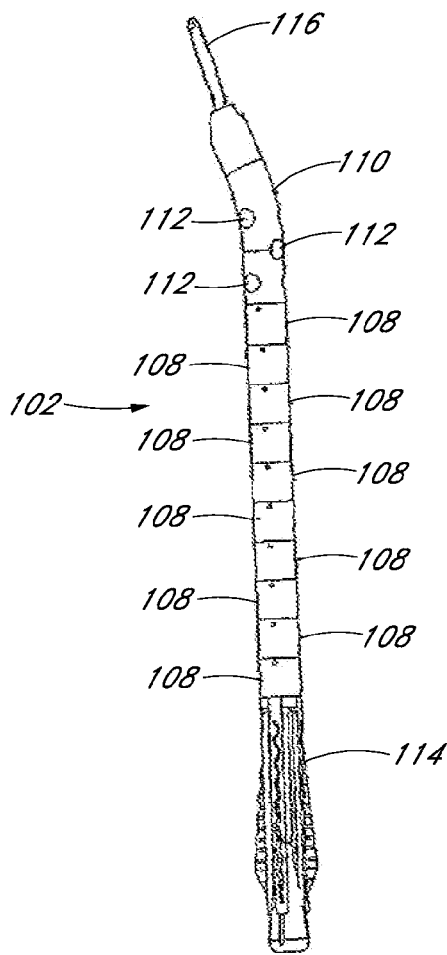
FIG. 24 is a front view of the implantable intramedullary fracture fixation device shown in FIG. 23.
Figure 25:
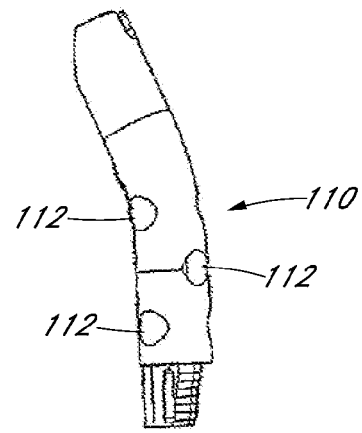
FIG. 25 is a front view of the proximal-most segment of the implantable fracture fixation device shown in FIG. 24.
Figure 26:
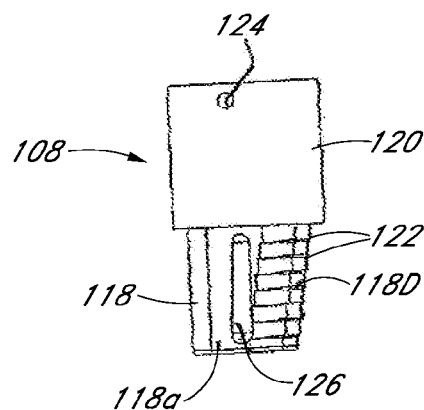
FIG. 26 is a front view of a typical intermediate segment of the implantable fracture fixation device shown in FIG. 24.

With reference to FIGS. 24-26, one embodiment of an implantable fixation structure 102 comprises a plurality of substantially identical, inter-fitting intermediate segments 108, (nine shown), a proximal end segment 110 having a plurality of holes or throughbores 112 adapted to receive fixation screws, and a radially-expandable distal end segment 114. A cable 116 is secured to the distal end segment that extends through the implantable structure beyond the proximal end segment 110 and through the cable tensioner 200 to apply a compressive force to the segments so as to result in a rigid implant. Each of the segments 108, 110 proximal to the distal end has an open interior to permit the tensioning cable 116 to pass there through and to allow the segments to slide along the cable 116 during insertion into the intramedullary canal.

In one embodiment the proximal end segment 110 and the intermediate segments 108 are pre-assembled, with the various segments hingedly secured to each other. In one embodiment, in order to facilitate insertion of the fixation structure 102 into the head of a long bone, where the entry point for the implant is offset from the axis of the long bone, the various segments 108, 110 of the implantable structure are configured to be relatively moveable only axially and laterally in a single plane. To this end, and with reference to FIGS. 26, 28 and 29, the intermediate segments 108 have inter-fitting male and female portions, 118 and 120, respectively, that comprise three substantially planar faces (118a, 118b and 118c for the male portion, and 120a, 120b and 120c for the female portion). The faces 118a, 120a are generally parallel to faces 118c, 120c, respectively, while the faces 118b and 120b are generally perpendicular to the faces 118a, 118b and 120a, 120b, respectively. A fourth face 118d, 120d is obliquely oriented relative to the longitudinal axis of the segment. Adjacent surfaces are joined by an arcuate surface. The three planar surfaces ensure that the assembled structure is flexible substantially only in a plane substantially parallel to the parallel faces of the male and female portions of the segments.

Experience has shown that when members with smooth or regular tapered or conical surfaces nest, there can be a tendency for the tapered surfaces to lock together. This, of course, would be disadvantageous in the present structure when trying to insert or remove the structure in its non-rigid state, as it would result in a reduced flexibility of the implantable structure required for insertion into and removal from the intramedullary canal. Accordingly, in one embodiment the obliquely-oriented surfaces 118d, 120d of the male and female portions 118, 120 of the segments 108 are formed with a series of steps 122 having surfaces that are substantially parallel to the axis of the segment. This ensures that if tension is not applied to the cable 116, and the fixation structure 102 is not under compression, the mating portions of the segments freely slide apart.

In one embodiment the various segments 108, 110 of the structure are secured to each other in a manner that permits limited axial movement relative to the adjacent segments, and ensures the proper orientation of the faces of the male portion of a segment with the female portion of the adjacent segment. In one embodiment, the limited axial movement can be in the range of 1 mm to 5 mm. In the structure of one embodiment, this is accomplished by providing the female portion 120 of the segment with a pin 124 (best seen in FIG. 28) lying in a plane perpendicular to that in which the assembled implant flexes. The pin 124 extends through the open interior of the female portion 120 of its associated segment and is captured in an axially-oriented, elongated slot 126 in the male portion 118 of the proximally adjacent segment. As seen in the drawings, the slot 126 is wider at the distal end than at the proximal end, providing for greater flexibility of the expanded implantable structure. Of course, the pin could be carried by the male portion 118 of the segment and ride in a slot in the female portion 120 to achieve the same or similar result.

In one embodiment the proximal end segment 110 has an open interior for passage of the tensioning cable and comprises two sections: an arcuate section 128 and a mating section 130, the latter having a male portion 118 as described above for seating in the female portion 120 of the immediately distal intermediate segment. In one embodiment, to allow for fixation of the proximal end of the implantable structure to the bone, the arcuate segment includes one or more throughbores 112 (three shown) oriented generally perpendicular to the axis of the implantable fixation structure 102 for the receipt of bone screws (not shown). The throughbores 112 are located so as to not intersect the open interior of the arcuate section, thus ensuring that the tensioning cable 116 is not contacted by the fixation screws. In one embodiment, throughbores 112 can be configured for insertion into a left-sided bone, a right-sided bone, or for both sides. For example, throughbores 112 can be configured for insertion into a right humerus, a left humerus, or either humerus, with throughbores 112 oriented in light of anatomy or access.

In one embodiment the proximal end of the arcuate section 128 is configured to receive a two-part distal collet assembly 132 (FIGS. 35 and 38) for locking the tensioning cable 116 (as will be described in greater detail below) and to also seat the screw guide interface 104 in a predetermined orientation.

As described in connection with the prior embodiments, the distal portion of the implantable structure can be configured to be fixed to the bone by bone screws, bone cement, or other fixing means. In one embodiment the fixation of the implantable structure to the distal portion of the long bone is accomplished by having the distal-most segment 140 be radially expandable so as to engage the surface of the intramedullary canal. To this end, and with reference to FIGS. 27, 32 and 33, in some embodiments the distal segment 140 comprises an expanding member 142 that receives a wedge member 144 on the interior thereof. The wedge member 144 is secured to the distal end of the tensioning cable so that as tension is placed on the cable 116, the wedge member 144 is moved proximally into the expanding member 142 to cause the expanding member 142 to radially expand into engagement with the surface of the intramedullary canal.

Figure 27:
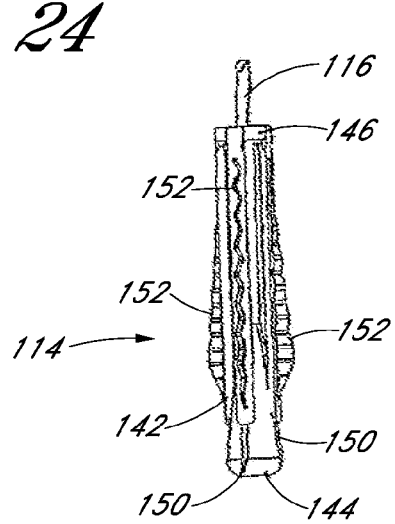
FIG. 27 is a front view of the distal-most segment of the implantable fracture fixation device shown in FIG. 24.
Figure 28:
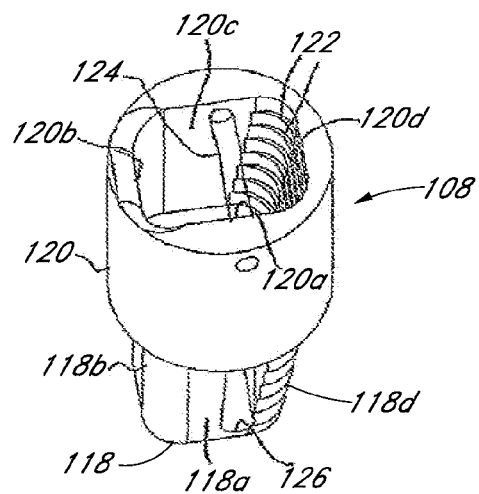
FIGS. 28 and 29 are perspective views of the intermediate segment shown in FIG. 26.
Figure 30:
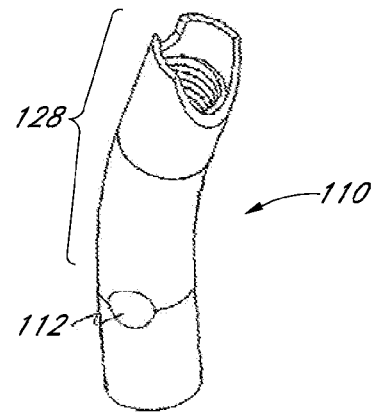
FIGS. 30 and 31 are perspective view of the proximal-most segment shown in FIG. 25.
Figure 29:
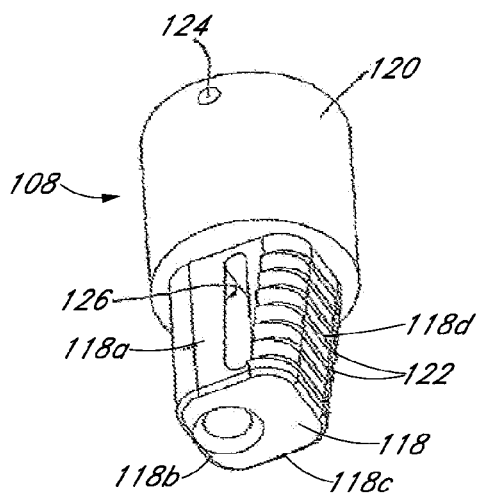
Figure 31:
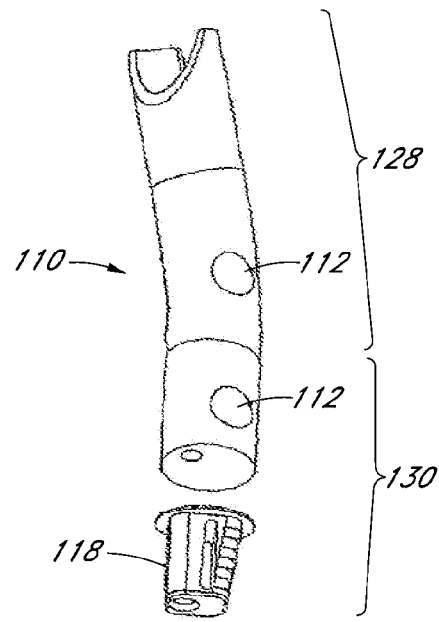
Figure 32:
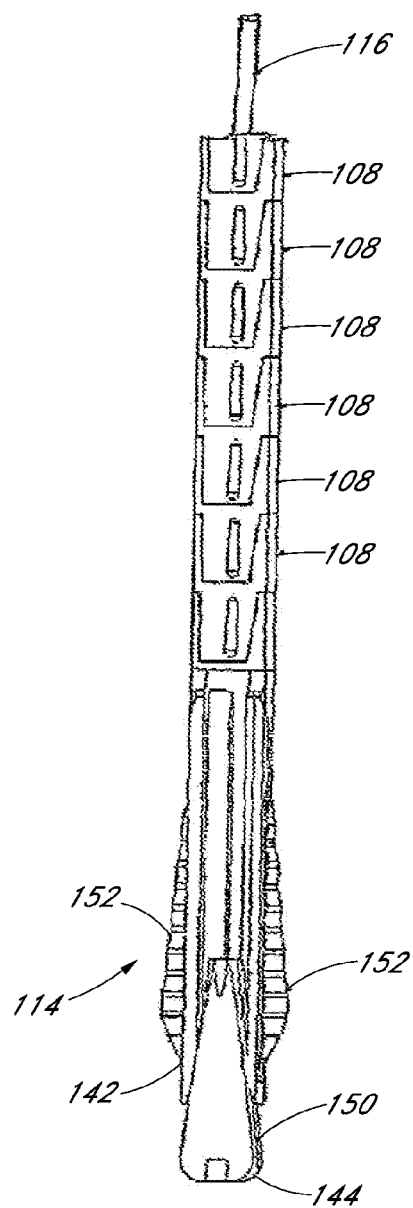
FIG. 32 is a cross-sectional view of the distal portion of the implantable fracture fixation device of FIG. 23, showing details as to the distal-most segment.
Figure 33:
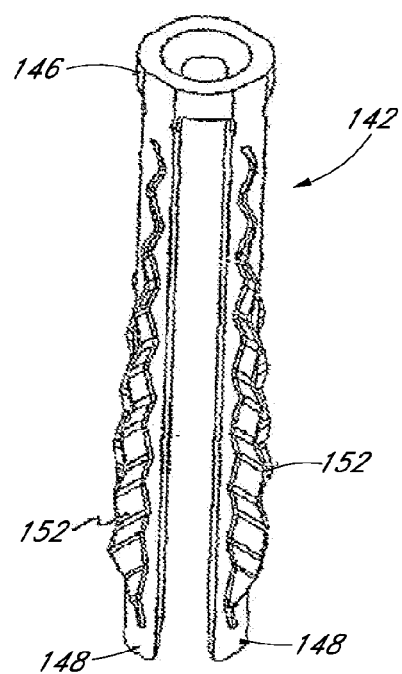
FIG. 33 is a perspective view of an expander forming a portion of the distal-most segment of FIG. 32.
Figure 34:
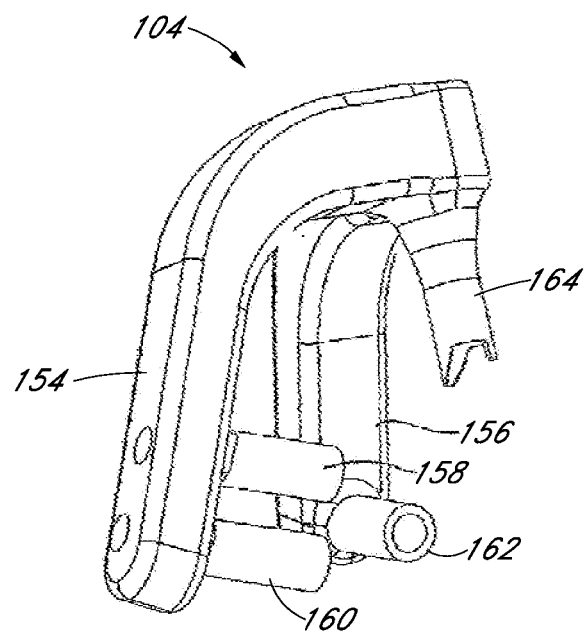
FIG. 34 is a perspective view of a screw guide interface adapted to be seated on the proximal end of the implantable fracture fixation device shown in FIG. 23.
Figure 35:
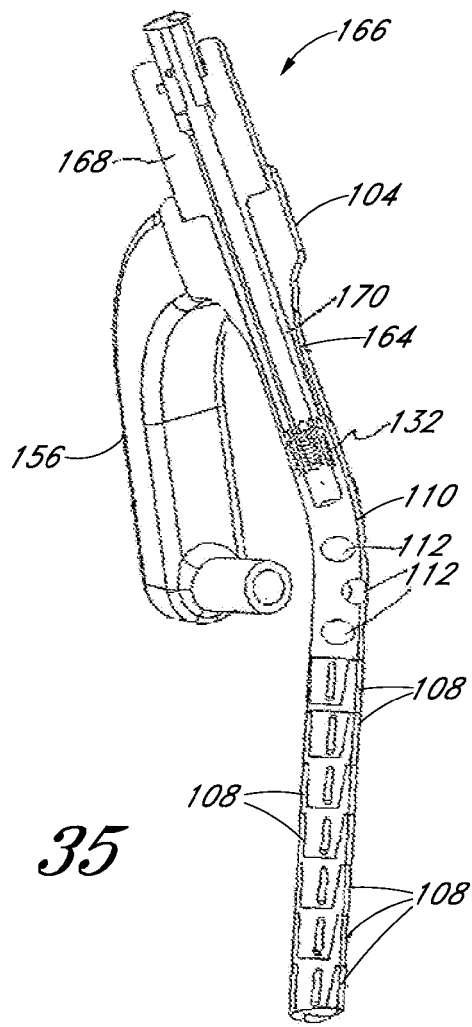
FIG. 35 is a cross-sectional view of the screw guide interface and the proximal end of the fracture fixation structure shown in FIG. 24.

The illustrated embodiments of an expander 142 in FIGS. 27, 32 and 33 can comprise an upper collar portion 146 from which extend in cantilever fashion a plurality of legs 148. In one embodiment the plurality of legs 148 are evenly radially-spaced legs 148 (four shown). In one embodiment in its undeformed state, the expander 142 has a radial dimension no greater than that of the other segments 108, 110 of the implantable fixation structure 102 in order to facilitate insertion into the intramedullary canal. The wedge member 144 is generally conical in shape, and has elongated grooves 150 in its surface for seating the legs 148 of the expander 142. Preferably, the grooves 150 have a cross-sectional shape that is complimentary to the inner surfaces of the legs 148.

In order to enhance the anchoring of the expander in the intramedullary canal, the outer surfaces of the legs may be formed with structures designed to more easily penetrate into the boney surface of the intramedullary canal. Such structures may take the form of points or a narrow edge or blade-like structure. In the illustrated embodiment, the outer surface of each leg is provided with a continuous raised spine 152. In one embodiment the spines 152 have a wavy or zig-zag configuration, which provides resistance to both axial and rotational movement of the embedded expander 142.

As noted above, in one embodiment, the proximal end segment 110 includes one, two, three, four or more throughbores 112 for receiving bone screws to secure the proximal end of the implant 102 in position. In one embodiment, multiple optional throughbores 112 can be configured for the optional use of bone screws for particular orientations or anatomy. To facilitate the placement of the screws, in one embodiment the proximal segment 110 is adapted to mount a screw guide interface 104. In various embodiments, the screw guide interface 104 can be configured to guide the one, two, three, four or more screws in proper orientation. In the illustrated embodiment, three screws are being used for illustrative purposes. In one embodiment a collet is adapted to mount a screw guide interface 104. As seen in the embodiments in FIGS. 34 and 35, the screw guide 104 comprises a pair of depending arms 154, 156, with a first arm 154 mounting a pair of guide tubes 158, 160 and a second arm 156 mounting a single guide tube 162. When the screw guide interface 104 is secured to the proximal end segment 110 of the implant 102, the guide tubes 158, 160, 162 are aligned with the throughbores 112. The upper ends of the arms 154, 156 are joined together, with a tubular-shaped segment 164 depending downwardly from the juncture of the arms 154, 156. The lower end of the tubular-segment 164 and the upper end of the proximal segment 110 are configured so that the screw guide interface 104 seats on the proximal segment 110 in proper orientation, with the screw guide tubes 156, 160, 162 aligned with their intended throughbores 112. Once properly seated, the screw guide interface 104 is secured to the implant by an insertion guide 166. The insertion guide 166 has an enlarged gripping surface 168 and a depending tubular section 170. The gripping surface 168 of the insertion guide 166 seats in a recessed portion of the screw guide interface 104, with the tubular section 170 of the insertion guide 166 extending through the tubular segment 164 of the screw guide interface 104 so as to be received in the proximal end of the proximal segment 110 of the implant 102. The distal end of the tubular section 170 of the insertion guide 166 is externally threaded, while the interior surface of the proximal end of the proximal segment 110 is internally threaded. Thus, the insertion guide 166 can be screwed into the proximal end segment 110 to secure the screw guide interface 104 in position on the implantable fixation device 102.

Figure 36:
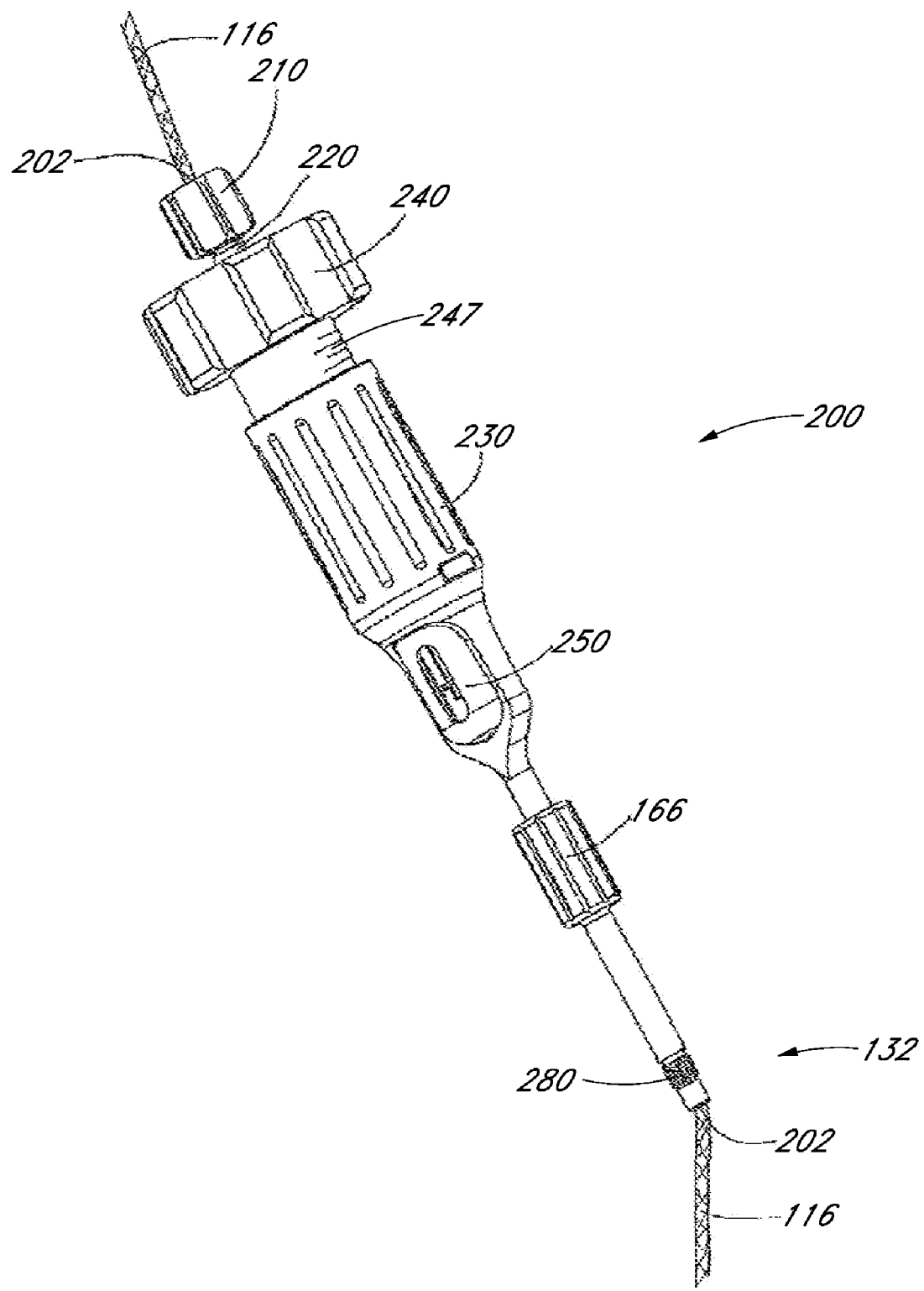
FIG. 36 is an enlarged perspective view of the cable tensioner according to one embodiment of the present invention.

A tensioner tool assembly may be utilized to regulate and/or lock tension on the cable in the fixation device. In one embodiment the tensioner tool assembly 200 may comprise a cable, a locking feature, a tensioner, and a locking mechanism actuator. Referring to FIG. 36, a perspective view of one embodiment of a tensioner tool assembly 200 is shown. It is appreciated that the tensioner tool assembly 200 may be used to provide and regulate tension to a cable, cord, tether or other flexible member connected to a segmented intramedullary fracture fixation device as set forth above, or may be used to provide and regulate tension for other implants, devices or systems. When used with a segmented intramedullary fracture fixation device such as segmented intramedullary structure 10 or fixation device 102, the tensioner tool assembly 200 may be guided over the cable 116 (connected to and extending from the fixation device, not shown), and releasably attached to the proximal end of the device. In one embodiment a proximal collet screw, a tensioner and a distal collet assembly comprising a cable collet screw may be actuated in sequence to attain and lock down the tension on the cable in the fixation device at a preferred level. The tensioner tool assembly 200 may then be removed, and the cable extending outside of the fixation device 200 may be cut off, while the cable inside the fixation device remains at the preferred tension.

In one embodiment the tensioner tool assembly 200 comprises a proximal collet 210 which engages within a threaded shaft 220. Distal to the proximal collet is a threaded knob 240 which partially extends into a housing 230. The housing 230 is shaped to be dockable in the insertion guide 166, which can connect to the proximal end of the fixation device. A collet driver 250 is captured within the housing 230 and is configured to be rotatable within the housing 230. Within the connection between the insertion guide 166 and the fixation device is the distal collet assembly 132. A cable bore 202 extends longitudinally along a straight path within the entire length of the assembly 200.

In one embodiment, when connecting the tensioner tool assembly 200 to the fixation device 102, first the insertion guide 166 may be guided over the cable 116 and attached to the fixation device 102, and then the remainder of the tensioner tool assembly 200 guided over the cable 116 and docked via the housing 230 within the insertion guide 166. Alternately, the tensioner tool assembly 200 may first be docked to the insertion guide 166, and the entire assembly then guided over the cable 116 and attached to the fixation device 102. Threads or other coupling features may provide an interface to dock the housing 230 to the insertion guide 166.

Figure 37:
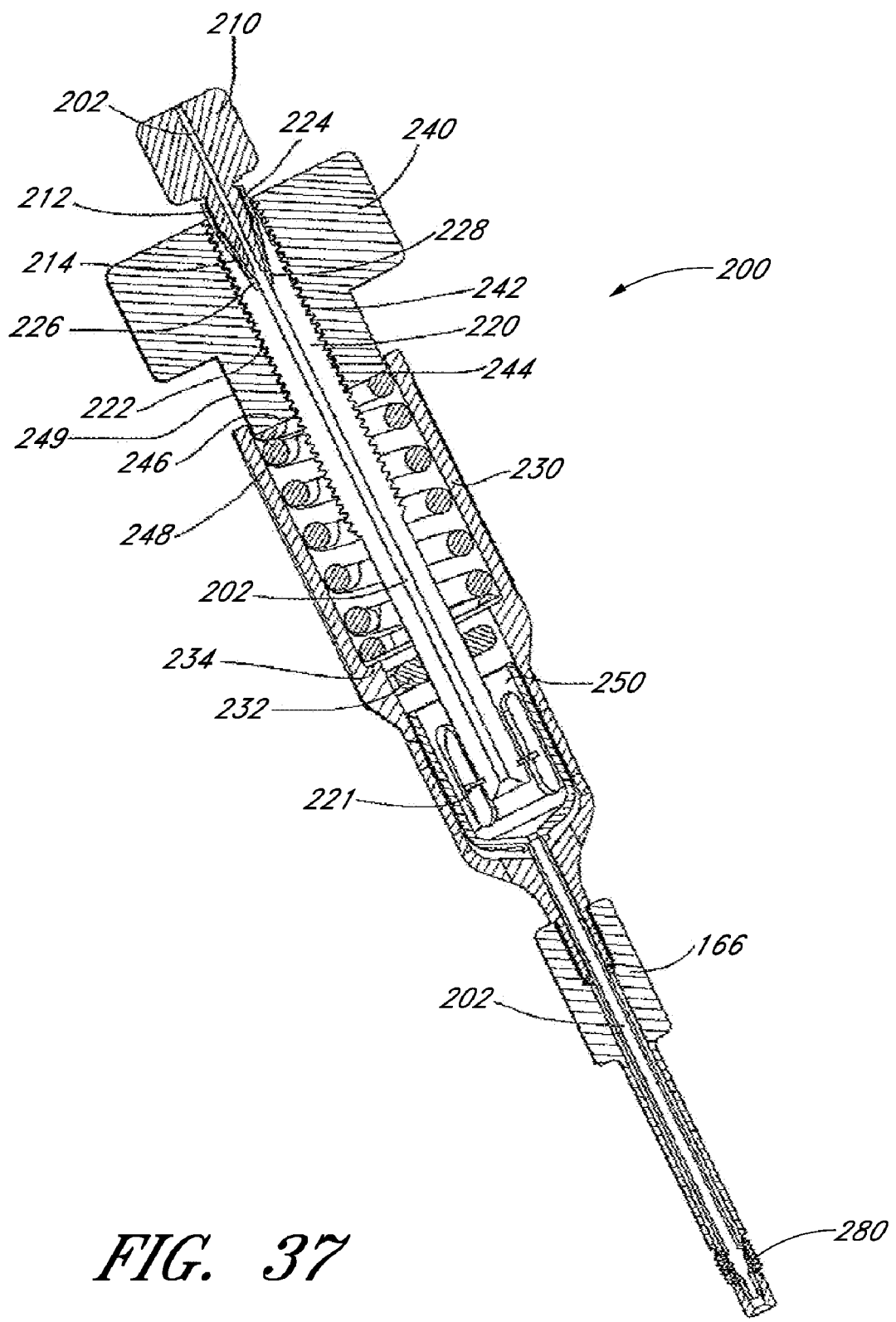
FIG. 37 is a cross-sectional view of the cable tensioner shown in FIG. 36.

Referring to FIG. 37, a longitudinal partial cross-sectional view of the tensioner tool assembly 200 is shown. For clarity in distinguishing the parts of the tensioner tool assembly, the cable is not shown. The cable bore 202 is seen extending the length of the assembly 200 along a straight path. The threaded knob 240 has an internally threaded lumen 242 through which the threaded shaft 220 extends. The threaded shaft 220 extends through the lumen 242 from the proximal end of the threaded knob 240, and into the housing 230. A crossbar 232, through which the shaft 220 passes, may provide an anti-rotation feature preventing rotation of the shaft. A retaining feature 221 may retain the distal end of threaded shaft within the housing 230, preventing accidental withdrawal of the threaded shaft 220 from the lumen 242. The threaded shaft 220 has external threads 222 which extend for a distance along its exterior. At the proximal end of the threaded shaft 220 is a short section of internal threads 224, and distal to the internal threads 224 is a chamber 226 with a tapered wall 228.

The proximal collet 210 fits into the proximal end of the threaded shaft 220. External threads 212 engage with the internal threads 224 on the threaded shaft to hold the collet 210. A plurality of flexible fingers 214 extend distally from the collet 210, into the chamber 226. As previously described, the tensioner tool assembly 200 is guided over the cable 116 (not shown), and the cable extends through the cable bore 202 and out the proximal end of the proximal collet 210. The proximal collet 210 is a locking feature which may be locked onto a location on the cable by screwing the proximal collet 210 into the threaded shaft 220. As the collet 210 is screwed in, the fingers 214 advance distally into the chamber 226. As the fingers 214 bias against the tapered wall 228, they are urged together, engaging and constricting the cable, until the cable is securely gripped. As the fingers 214 engage the cable, they may substantially circumferentially surround the cable. In this position, the cable is locked and prevented from being pulled in either direction. However, the cable can again be freely moved by simply unscrewing collet 210 from within threaded shaft 220 so that fingers 214 are able to freely, outwardly flex and disengage from the cable. In one embodiment it is noted that in the locking process, the cable 116 remains oriented substantially along a straight path within the assembly 200 and is not bent, curved, crimped or severed.

Once the cable is locked the tensioner may be actuated to regulate tension to the cable. In one embodiment the tensioner may comprise the housing 230, the threaded knob 240, the threaded shaft 220, the crossbar 232, and the retaining feature 221. The threaded knob 240 may be actuated by turning it to provide tension to the cable. As the knob 240 is turned, internal threads 244 engage with the external threads 222 on the threaded shaft 220, and the knob 240 moves distally while the threaded shaft 220 moves proximally as the rotational motion is translated into linear motion. Since the cable is connected to the fixation device at a first location at the distal end segment of the fixation device, and locked within the collet 210 within the shaft 220 at a second location, moving the shaft 220 proximally moves the collet 210 relative to the fixation device, putting tension on the cable between the first location at the fixation device and the second location at the collet.

In one embodiment, as the knob 240 moves distally, a distal face 246 of the knob 240 pushes on a spring 248 which surrounds the threaded shaft 220 in the housing 230. As the knob 240 is turned further, the spring 248 is compressed between the knob distal face 246 and a lip 234 formed in the wall of the housing 230. This compression may provide a measure of the amount of force applied to the knob. Indicator markings 247 (shown in FIG. 36) may be present on the outside of a distal wall 249 of the threaded knob 240 to indicate a measurement. In one embodiment the indicator markings 247 indicate the amount of force as the knob is turned. In one embodiment the indicator markings 247 indicate the amount of axial movement by the cable with respect to the distal end of the fixation device in terms of length as the knob 246 is turned. The knob 246 is actuated by turning either direction, increasing or decreasing the tension, until a preferred level of tension is reached.

Figure 38:
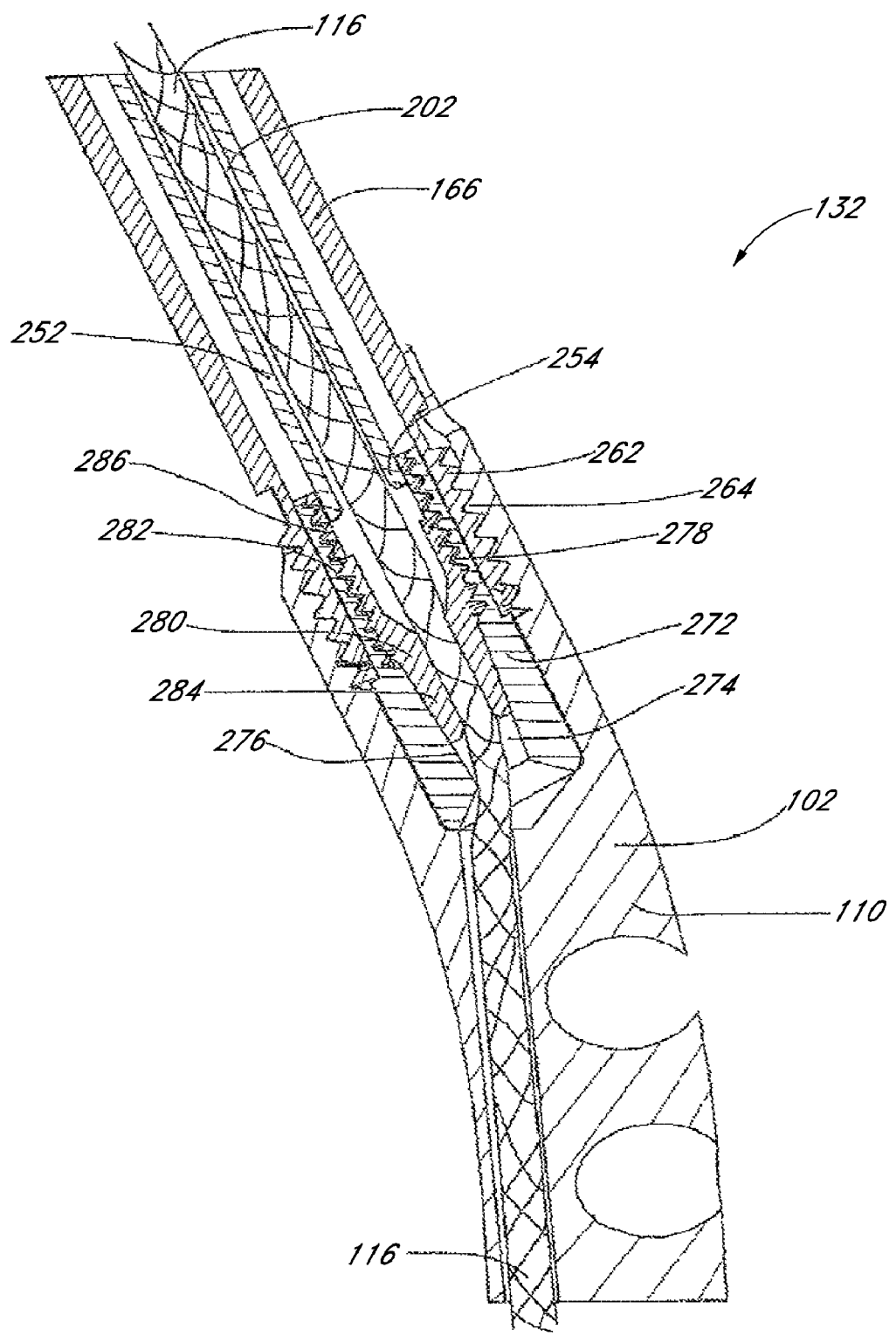
FIG. 38 is an enlarged cross-sectional view of the cooperating structure of the cable tensioner and the proximal-end segment of the fracture fixation device according to one embodiment of the present invention.

Referring to FIG. 38, a partial cross-sectional view of a cable 116 passing through the distal collet assembly 132, which is surrounded by a connection between a portion of the insertion guide 166 and a proximal end segment 110 of the fixation device 102, is shown. For clarity, the cable 116 is not shown in cross-section, but a stylized outer surface of the cable 116 is shown. External connection threads 262 on the insertion guide 166 engage with internal connection threads 264 on the fixation device 102 to hold the insertion guide 166 in a fixed position relative to the fixation device 102. A cable collet anchor 272 fits within the proximal end 110 of the fixation device 102 and extends for a short distance into the insertion guide 166. The cable collet anchor 272 may be integrally formed in, welded, bonded, press-fit or otherwise connected to the fixation device 102. A chamber 274 having a tapered wall 276 is in a distal end of the cable collet anchor 272, and the proximal end of the cable collet anchor has internal collet threads 278.

A cable collet screw 280 fits within the cable collet anchor 272, held in place by external collet threads 282 which engage with the internal collet threads 278. At a proximal end of the cable collet screw 280, a shaped inner wall 286 surrounds the cable bore 202. A plurality of flexible fingers 284 extend distally, into the chamber 274. In one embodiment, together the cable collet screw 280 and the cable collet anchor 272 form a locking mechanism.

Extending distally through the insertion guide 166 is a driver shaft 252 of the collet driver 250. As seen in FIG. 38, the collet driver 250 is captured within the tensioner, but operates independently from the tensioner. A working end 254 of the driver shaft 252 is shaped to mate with the shaped inner wall 286 of the cable collet screw 280. In various embodiments the working end 254 may be shaped as a hexagon or any other shape configured to mate with the cable collet screw. In various embodiments, the working end 254 of the driver shaft 252 can be configured to operate with any shaped interface on the cable collet screw 280.

In one embodiment, after the cable 116 has been tensioned as set forth above, the collet driver 250 is actuated to actuate the locking mechanism which includes the cable collet screw 280 and anchor 272. To lock the position of the tensioned cable 116 at a third location, which is relative to the fixation device 102, the cable collet screw 280 is tightened. To tighten the cable collet screw 280, the collet driver 250 is turned, turning the collet driver shaft 252. The working end 254 mates with the shaped inner wall 286 of the cable collet screw, and consequently the cable collet screw 280 is turned. As the collet screw 280 turns and advances within the anchor 272, the fingers 284 advance into the chamber 274. As the collet fingers 284 bias against the tapered wall 276, they are urged together, gripping the cable 116 and locking its position relative to the fixation device 102. In this position, cable 116 is prevented from being pulled in either direction. However, cable 116 can again be freely moved by simply unscrewing collet screw 280 from within the anchor 272 so that fingers 284 are able to freely, outwardly flex.

In one embodiment, once the cable 116 is locked in the cable collet screw 280, the tension on the cable relative to the fixation device 102 is fixed. The proximal collet 210 may be unscrewed, releasing its grip on the cable 116. The housing 230 may be undocked from the insertion guide 166, allowing removal of the tensioner tool 200 from the insertion guide 166. The insertion guide may then be unscrewed and removed from the fixation device 102, leaving the cable 116 locked in the cable collet screw 280. Alternately, in one embodiment, the housing 230 may remain docked within the insertion guide 166, and the insertion guide 166 may be uncoupled from the fixation device 102, bringing the docked tensioner tool 200 with it. After both the insertion guide and tensioner tool are removed, the cable 116 extending proximally from the distal collet screw 280 may be cut to a preferred length proximal to the cable collet screw 280.

Various embodiments of intramedullary structures as disclosed herein may list various parameters, such as sizes, lengths, diameters, widths, curvatures and geometry that can conform to or be implanted based on various parameters of bones and of structures in which embodiments of the devices may be configured to be implanted. Listings provide some examples, but should not be read to limit the disclosure to those specific dimensions or characteristics. For example, the number of segments used in a device and its various size and shape and feature characteristics can vary depending on parameters of the bone and/or patient, the type of fracture, and other factors. Embodiments of the intramedullary structures are scalable. For example, some non-limiting diameters (or widths) of certain embodiments could range from about 5 mm (for such uses as pediatric bones, or adult clavicle, radius) to about 18 mm (for such uses as an adult femur). Embodiments of lengths could very from a few inches to 800 mm in a knee fusion nail (from ankle to hip). Various embodiments may be configured for implantation in any long bone anatomies, including but not limited to a femur, tibia, fibular, humerus, ulna, radius, clavicle, metatarsals, metacarpals, and others.

In one embodiment a segmented intramedullary structure 300 comprising segments 310 is similar or has features the same or similar to the features of intramedullary structure 10 with segments 12 and/or implantable segmented intramedullary fracture fixation device structure 102 with segments 110, 108 and 114, or any other implant with segments described herein. In one embodiment a segmented intramedullary structure 300 comprises a number of primary components: a segment construct, a braided cable, a stiffening tube for the cable, a collet, an end cap and bone screws. In one embodiment the segment construct contains a series of segments 310 with complementary interfaces between the segments 310. In various embodiments the complementary interfaces can comprise complementary surfaces, complimentarily-shaped features, mating male and female portions, nested features, paired geometries, and the like which can interface a proximal, medial, intermediate, middle, or distal portion, area, or end of the respective segments. In one embodiment a segment 310 has a first interface and a complementarily-shaped second end interface, so that the first interface of a segment 310 cooperatively engages the second interface of an adjacent segment 310. In one embodiment segments 310 have a male geometry at one end, a female geometry on the opposite end and a hole or channel substantially extending along the linear axis. In various embodiments the segment construct can contain straight segments and/or transition segments. In one embodiment the individual segments are rigid. In one optional embodiment the individual segments are flexible. In one embodiment transition segments increase or decrease in width or diameter along the length of the transition segment. One or more transition segments can be used to transition the width, size, diameter, or thickness of the segment construct between proximal, intermediate, and/or distal ends or regions. In one embodiment the male geometry of the links comprises an elliptical shaped cone or taper which mates with a similar elliptical taper on the female geometry of the adjacent link. In one embodiment the individual links are connected together with a snap ring so that the male geometry resides within the female geometry.

In various embodiments the complementary interfaces of the individual links or segments 310 can be configured to allow movement of segments 310 with respect to each other between two, three, or more configurations. In one embodiment the segments 310 can be distracted from each other, in a distracted configuration 308 in which two or more segments 310 are at least axially moved away from each other. See FIG. 58B. In one embodiment distracted segments 310 can still be attached to each other, but farther apart. In one embodiment segments 310 are removably attachable from each other to prevent segments 310 from completely separating from each other when distracted. In one embodiment segments 310 are locked to each other to prevent segments 310 from completely separating from each other when distracted. In one embodiment segments 310 are permanently attached to each other to prevent segments 310 from completely separating from each other when distracted. In one embodiment the segments 310 can have an axial displacement length 304, indicating the axial distance along a longitudinal axis of one or both adjacent segments 310 that the adjacent segments 310 can move with respect to each other while still connected to each other. In various non-limiting embodiments, the axial displacement length 304 between adjacent segments can be anywhere in a range of 2-10 mm, including but not limited to roughly 2 mm, 3 mm, 4 mm, 5 mm, 6 mm, 7 mm, 8 mm, 9 mm and 10 mm. In one embodiment, the overall length of a segmented intramedullary structure 300 increases as segments are distracted with respect to each other with segments 310 in one or more respective distracted configurations 308. In one embodiment a segmented intramedullary structure 300 can maintain an overall configuration, such as a straight configuration, while distracted. In one embodiment a segmented intramedullary structure 300 can be configured to bend or flex or have segments 310 that move rotationally with respect to each other in a distracted configuration 308.

In one embodiment the segments 310 can be flexed, rotated or bent with respect to each other, in a bent configuration 307 in which two or more segments 310 are at least radially rotated with respect to each other. See FIG. 58C. In one embodiment the segments 310 can have a rotational displacement angle 305, indicating the angle between the respective longitudinal axes of the adjacent segments 310 that the adjacent segments 310 can move with respect to each other while still connected to each other. In various non-limiting embodiments, the rotational displacement angle can be up to 4, 5, 10, 15, 20, 30, 45 or 90 degrees. In one embodiment the segments 310 are distracted in order to bend with respect to each other. In one embodiment, pushing segments 310 together or compressing them causes the segments 310 to move towards each other in to a compressed configuration. In one embodiment pushing segments 310 together or compressing them while the segments 310 are more than a specific angle with respect to each other temporarily locks the segments 310 in a bent configuration 307, allowing the segments 310 to be pushed or to transmit an axial load without collapsing out of its bent configuration 307. In one embodiment segments 310 are configured to remain in a first bent configuration 307a while adjacent segments 310 are at least a first rotational displacement angle 305a. In one embodiment segments 310 are configured to move out of a first bent configuration 307a while adjacent segments 310 are less than the first rotational displacement angle 305a. For example, in one embodiment the overall shape of a segmented intramedullary structure 300 can be bent, flexed, or curved with two or more of its segments 310 rotated with respect to each other with an angle of at least a first rotational displacement angle 305a. When the segments 310 are at an angle of at least the first rotational displacement angle 305a, the curved segmented intramedullary structure 300 can be pushed or pulled through a hole in tissue such as skin or bone while still curved. Once the angle between segments 310 reduces to an angle less than the first rotational displacement angle 305a, the segments 310 can move out of the first bent configuration 307a. In various embodiments, multiple rotational displacement angles 305 can determine multiple bent configurations 307.

In various embodiments, a compressed configuration may have an overall shape for the adjacent segments in a curved or straight configuration. In one embodiment two or more segments 310 can be compressed against each other, in a compressed configuration 306 in which two or more segments 310 are configured to be aligned with respect to each other with a reduced axial displacement and a reduced rotational displacement with respect to each other. See FIG. 58D. In one embodiment segments 310 are in a straightened configuration when compressed. In one embodiment the axial displacement length between segments 310 is substantially zero when in the compressed configuration 306. In one embodiment the rotational displacement angle 305 between segments 310 is substantially zero when in the compressed configuration 306. The measurement of various lengths and angles may depend on the application, size of the segments, number of segments, size of bone for implantation, approach (retrograde, etc.), or other factors. In various embodiments, interaction between features on the interior and/or exterior surfaces of adjacent segments 310 can be configured to adjust or determine the axial distraction range of motion and/or rotational bending range of motion of the segments 310 with respect to each other.

In one embodiment the individual links can be partially separated to provide flexibility but will become substantially rigid once the individual links are compressed together. In one embodiment the individual links can be partially separated to provide a first level of flexibility but will become a different, second level of flexibility once the individual links are compressed together. In one embodiment the second level of flexibility is less than the first level of flexibility. In one embodiment an attachment structure prevents the segments from becoming permanently separated, thus aiding with device removal or extraction if necessary. In various non-limiting embodiments, the attachment structure can include a pin, slot, snap fit, threads, or a snap ring. In one embodiment, during the surgical procedure, the segment construct will be inserted into the bone canal over the cable and cable stiffening tube. Tension is applied to the cable in order to compress the tapered male geometry and tapered female geometry together to form a rigid nail. The cable tension will be held by a collet that is threaded into the proximal end of the segment construct. In one embodiment, the device is intended to function as a flexible intramedullary nail during the surgical procedure but will become rigid once the cable is tensioned and the segment construct is compressed. In one embodiment the rigid device is secured to the bone with bone screws that are inserted through the proximal and distal segments. In one embodiment, two bone screws are used in the proximal segment and two bone screws are used in the distal segment. In one embodiment, an end cap is threaded into the proximal segment after the device is secured in order to prevent bone in-growth around the cable collet. Once the end cap is in place the cable will be cut flush with the end cap.

In one embodiment, a segmented intramedullary structure is configured for insertion in a humeral bone. In one embodiment the bone screws are 4.0 mm in diameter. In one embodiment of a humeral segmented intramedullary structure the hole, or channel, is 2.25 mm in diameter. In various embodiments the humeral segmented intramedullary structure can be provided in various diameters, such as (but not limited to) 8 mm, 9 mm or 10 mm. In various embodiments the humeral segmented intramedullary structure can be provided in various lengths, such as (but not limited to) 170 mm, 187 mm, 205 mm, 222 mm, 240 mm, 257 mm, 275 mm or 292 mm. In various embodiments the humeral stiffening tube can be provided in various lengths which can correspond to the increasing length of the segmented intramedullary structure. In various embodiments the humeral end cap can be provided in various lengths, such as (but not limited to) 12.7 mm, 17.7 mm or 22.7 mm. In various embodiments the humeral bone screws can have a 4.0 mm diameter and any of the following non-limiting examples of lengths: 16 mm, 18 mm, 20 mm, 22 mm, 24 mm, 26 mm, 28 mm, 30 mm, 32 mm, 34 mm, 36 mm, 38 mm, 40 mm, 42 mm or 46 mm. In various embodiments, the cable length can be configured to work with any device, depending on device length. In one embodiment the cable has a pre-cut length of 914 mm.

In various embodiments a segmented intramedullary structure is configured for insertion in bones of varying shapes and/or sizes. In various embodiments, the nominal diameter of a segmented intramedullary structure can be 8 mm, 9 mm, 10 mm, 11 mm, 12 mm, 13 mm, 14 mm, 15 mm or other dimensions. In various embodiments, the diameter of a proximal end segment of a segmented intramedullary structure can be 11 mm, 14 mm, 16 mm or other dimension. In various embodiments, transition segments can range in width or diameter from 8 to 9 mm, 9 to 10 mm, 10 to 11 mm, 11 to 12 mm, 12 to 13 mm, 13 to 14 mm, 14 to 15 mm, 15 to 16 mm, or other transition sizes. In various embodiments, straight segments can have a width or diameter of 8 mm, 9 mm, 10 mm, 11 mm, 12 mm, 13 mm, 14 mm, 15 mm, or other sizes. In one embodiment, a distal segment can be tapered. In various embodiments a distal segment can be tapered distally by 1 mm, 0.5 mm or other values. In various embodiments, a segmented intramedullary structure can built to varying lengths, comprising varying numbers of segments (transition, straight, or otherwise) as needed. In various embodiments, lengths can be about 170 mm to about 500 mm.

Secondary Compression

Figure 39A:
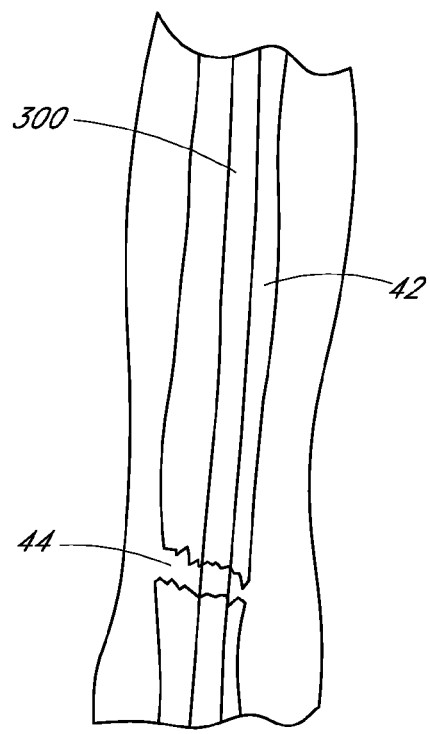
FIGS. 39A-39B are schematic representations of secondary compression in a long bone using an embodiment of a segmented intramedullary structure.
Figure 39B:
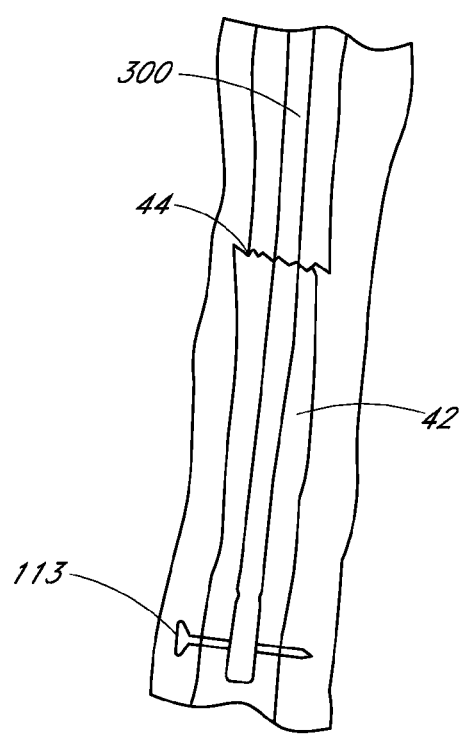
Figure 40A:
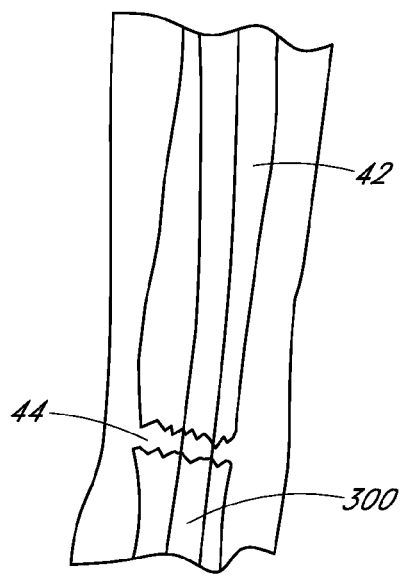
FIGS. 40A-40B are schematic representations of secondary compression in a humerus using an embodiment of a segmented intramedullary structure.
Figure 40B:
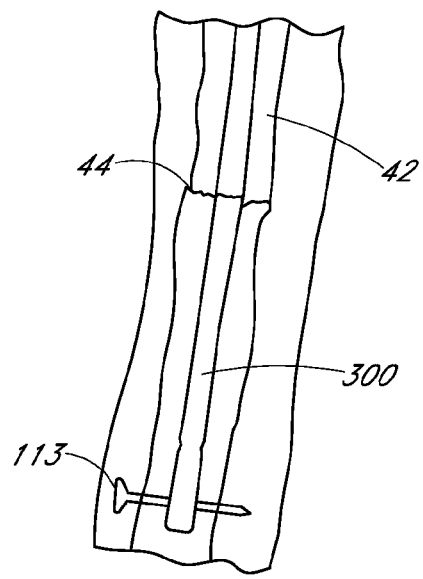

Various embodiments of segmented intramedullary structures as disclosed herein allow the surgeon to compress the fracture site after placing the segmented intramedullary structure in the bone and fixating the proximal and distal bone segments. See FIGS. 39A-B and FIGS. 40A-B, which illustrate an embodiment of a segmented intramedullary structure 300 before and after secondary compression in a bone 42. Segmented intramedullary structure 300 can have the same or similar aspects as segmented intramedullary structure 10 and implantable segmented intramedullary fracture fixation device structure 102. Bone 42 can be any type of bone, such as, but not limited to, a long bone. FIGS. 39A and 40A illustrate one embodiment of a segmented intramedullary structure 300 with the fractured long bone 42 attached superiorly and inferiorly to the fracture site to the segmented intramedullary structure 300. After this superior and inferior anchoring or attaching at a proximal and distal sites, an embodiment of the segmented intramedullary structure 300 can have an interior cable or tensioning mechanism lock or rigidly connect the segments of the segmented intramedullary structure 300 together, imparting a compressive load across the bone fracture site 44 to assist in healing the fracture 44, as shown in FIGS. 39B and 40B. This compression feature is particularly useful in non-load bearing bones 42 such as in the arm where even a 1 mm gap at the fracture site can prevent healing. In one embodiment, this type of compression can be called "Secondary Compression."

In some embodiments secondary compression may be expressed in terms of compressive force applied to bring bone segments together with a device. In some embodiments secondary compression may be expressed in terms of the tensile force applied to a tensioning mechanism to bring bone segments together with a device. In some embodiments, secondary compression can be described in terms of a distance, such as the distance that bone segments are brought together in secondary compression. In one embodiment secondary compression is expressed in terms of the decrease in the decrease in axial length of the device along the direction of the secondary compression. In one embodiment the distance associated with secondary compression is proportional to the amount of compressive or tensile force applied to the device. In one embodiment segmented intramedullary structures can be configured to provide substantially one level or one distance in secondary compression. In one embodiment segmented intramedullary structures can be configured to provide varying levels or ranges of secondary compression. In one embodiment a segmented intramedullary structure can provide a smooth, continuous transition between levels of secondary compression. In one embodiment a segmented intramedullary structure can provide a discrete transition between levels of secondary compression. In one embodiment a segmented intramedullary structure can provide a discrete transition between levels of secondary compression with a ratcheting action.

In one embodiment a segmented intramedullary structure can provide no secondary compression. In various embodiments a segmented intramedullary structure can be configured to provide a single secondary compression distance with a value in the range of about 1 mm to 5 mm. In various embodiments a segmented intramedullary structure can be configured to provide 1 mm, 2 mm, 3 mm, 4 mm, or 5 mm of secondary compression. In one embodiment a segmented intramedullary structure is configured to provide anywhere in the range of about 1 mm to 5 mm of secondary compression.

Studies were performed with various embodiments of the segmented intramedullary structure confirming that secondary compression of the fracture site after the fracture has been reduced and proximal and distal fixation is in place helps ensure that the surgeon reaches full reduction at the fracture site. In one embodiment, an additional benefit of secondary compression is that it takes some of the load off the implant which will help in implant longevity.

Segments

With reference to FIGS. 41A-78, further embodiments of segmented intramedullary structures 300 with segments, generally designated 310, are disclosed. In one embodiment, segment 310 can have features similar to the various embodiments of the various other segments described herein, such as segments 12, 108, or others. Various terms or parts may have features which can be the same or similar to other described embodiments herein. In various embodiments segment 310 has a male mating section 320 and a female mating section 330. In various embodiments segment 310 has a channel 340 extending through a longitudinal axis of the segment 310.

In various embodiments, segments 310 can be subjected to secondary compression with an elongate member 350. In various embodiments elongate member 350 can be a wire, guide wire, pull wire, push wire, cable, rod, threaded rod, or other similar structure. In one embodiment the elongate member is a tensioning member extending along the length of the segmented intramedullary structure. In one embodiment elongate member 350 is a tensioning rod 14, which is extended through the segment 310. In one embodiment the elongate member 350 is cable 116. In one embodiment the elongate member 350 provides a means for holding the segments 310 together in a generally axial, straight, straightened or curved configuration. Although the term "straight" or "straightened" may be used with respect to the segments, it is contemplated that segments may be configured to align an assembly in a straight line, but may also be configured in certain embodiments to "lock" in a rigid configuration that has a curvature or bend to the overall structure. The segments 310 can be distracted from each other in order to allow bending in one or more planes or about one or more axes.

Figure 41C:
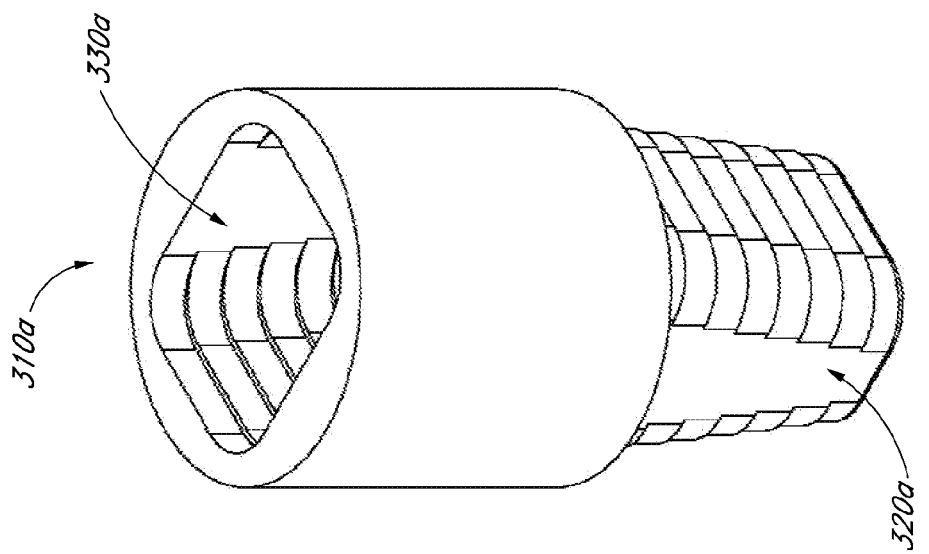
FIG. 41C is a schematic perspective view of the stepped segment of FIG. 41A.
Figure 41B:
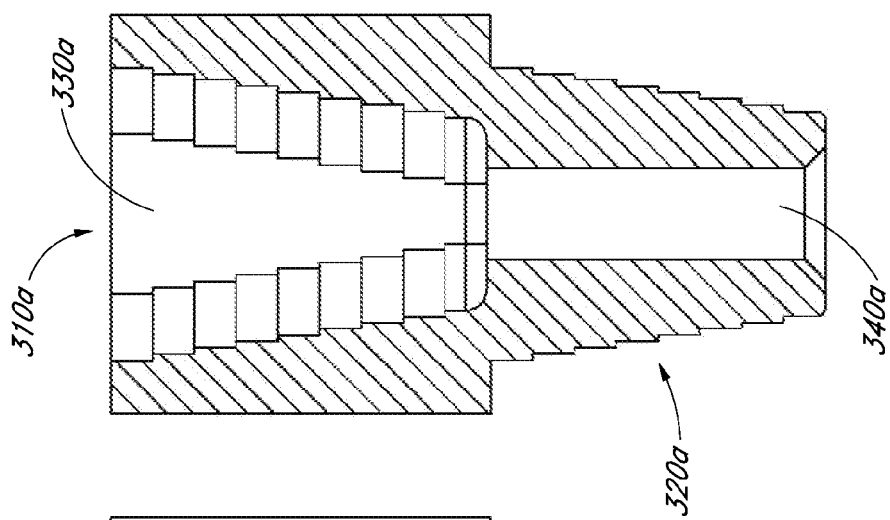
FIG. 41B is a schematic cross-sectional side view of the stepped segment of FIG. 41A.
Figure 41A:
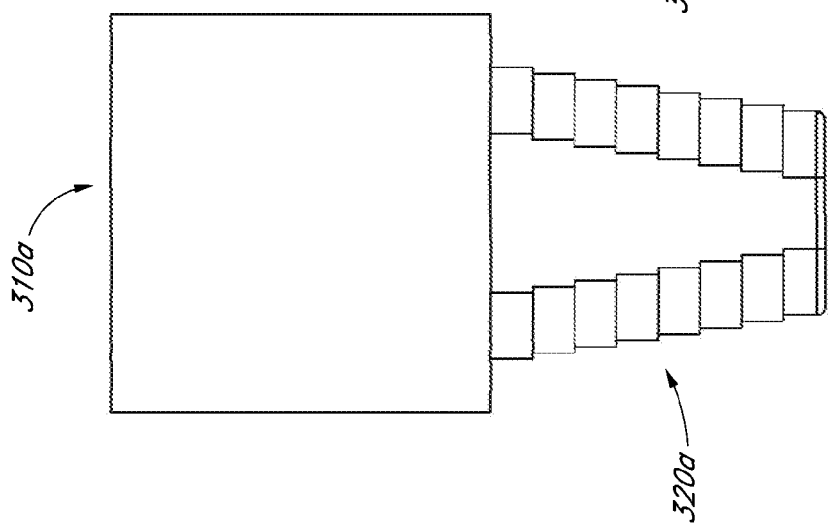
FIG. 41A is a schematic side view of an embodiment of a stepped segment of a segmented intramedullary structure.
Figures 42A, 42B, 42C:
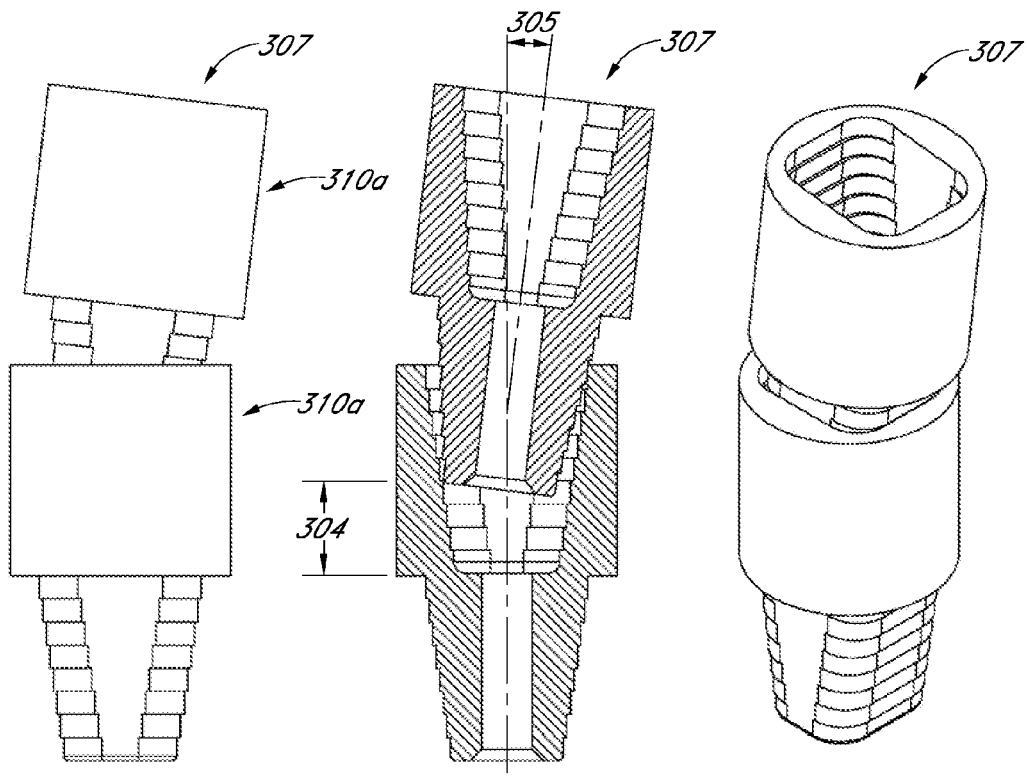
FIG. 42A is a schematic side view of an embodiment of a pair of adjacent stepped segments of FIG. 41A in a bent configuration.
FIG. 42B is a schematic cross-sectional side view of the pair of adjacent stepped segments of FIG. 41A in a bent configuration.
FIG. 42C is a schematic perspective view of the pair of adjacent stepped segments of FIG. 41A in a bent configuration.
Figures 43A, 43B, 43C:
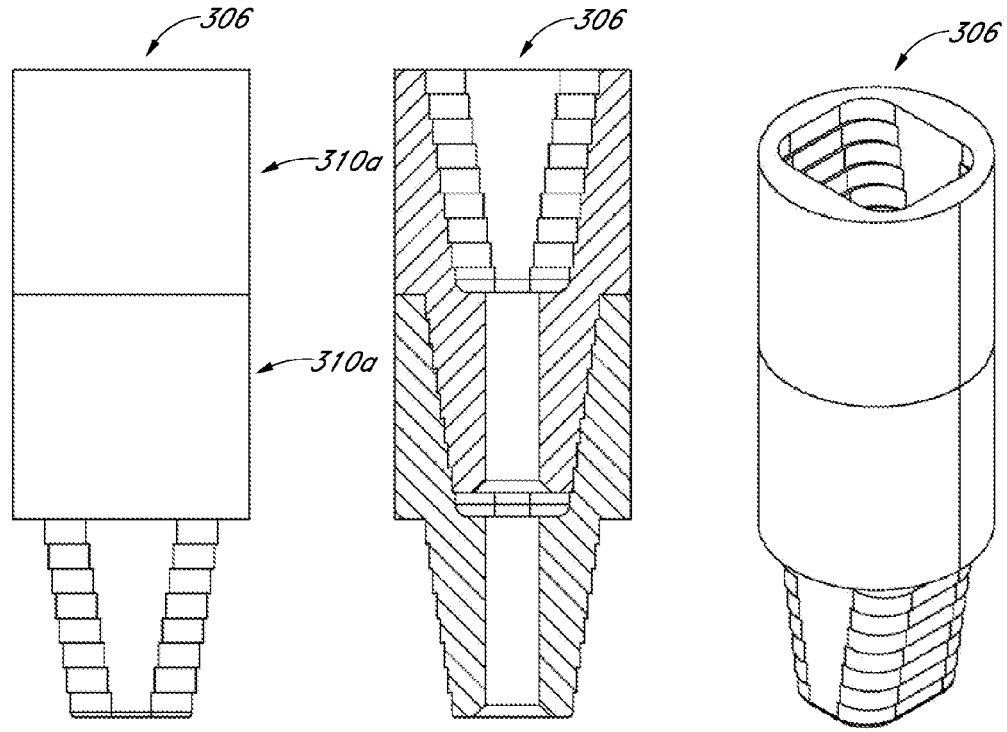
FIG. 43A is a schematic side view of an embodiment of a pair of adjacent stepped segments of FIG. 41A in a straightened, or compressed configuration.
FIG. 43B is a schematic cross-sectional side view of the pair of adjacent stepped segments of FIG. 41A in a straightened configuration.
FIG. 43C is a schematic perspective view of the pair of adjacent stepped segments of FIG. 41A in a straightened configuration.
Figures 44A, 44B, 44C, 44D, 44E:
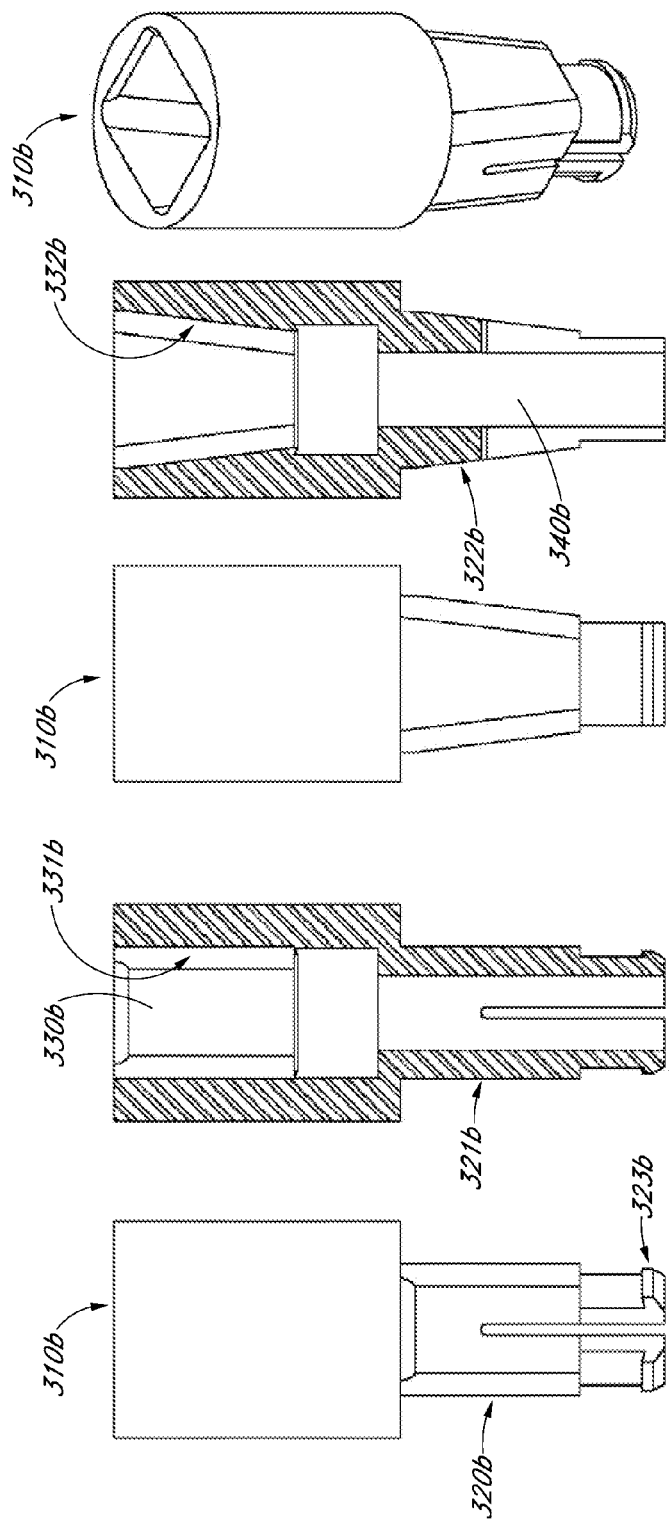
FIG. 44A is a schematic front view of an embodiment of a snap segment of a segmented intramedullary structure.
FIG. 44B is a schematic cross-sectional front view of the snap segment of FIG. 44A.
FIG. 44C is a schematic side view of an embodiment the snap segment of FIG. 44A.
FIG. 44D is a schematic cross-sectional side view of the snap segment of FIG. 44A.
FIG. 44E is a schematic perspective view of the snap segment of FIG. 44A.
Figures 45A, 45B, 45C, 45D, 45E:
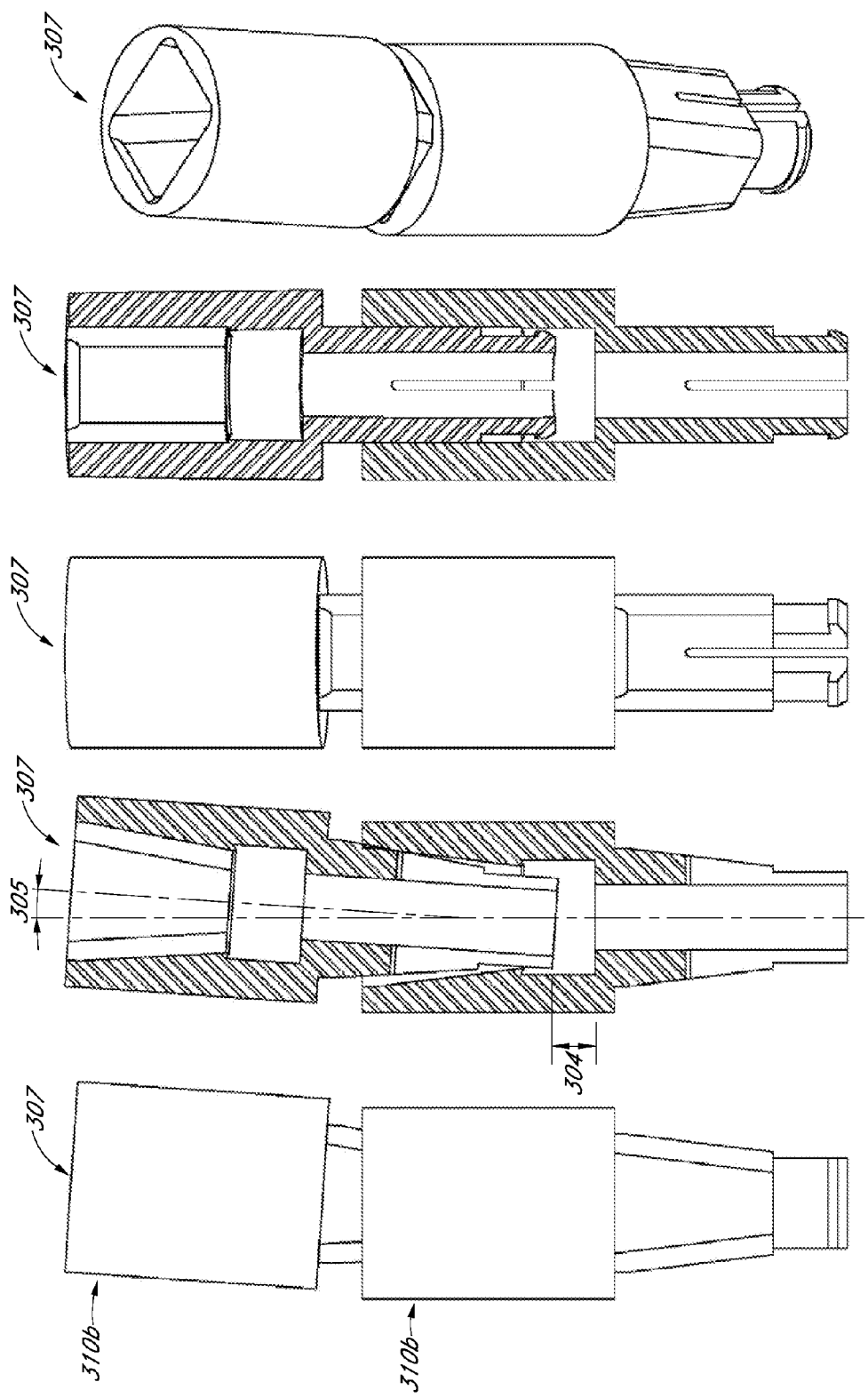
FIG. 45A is a schematic side view of an embodiment of a pair of adjacent snap segments of FIG. 44A in a bent configuration.
FIG. 45B is a schematic cross-sectional side view of the pair of adjacent snap segments of FIG. 44A in a bent configuration.
FIG. 45C is a schematic front view of the pair of adjacent snap segments of FIG. 44A in a bent configuration.
FIG. 45D is a schematic cross-sectional front view of the pair of adjacent snap segments of FIG. 44A in a bent configuration.
FIG. 45E is a schematic perspective view of the pair of adjacent snap segments of FIG. 44A in a bent configuration.
Figures 46A, 46B, 46C, 46D, 46E:
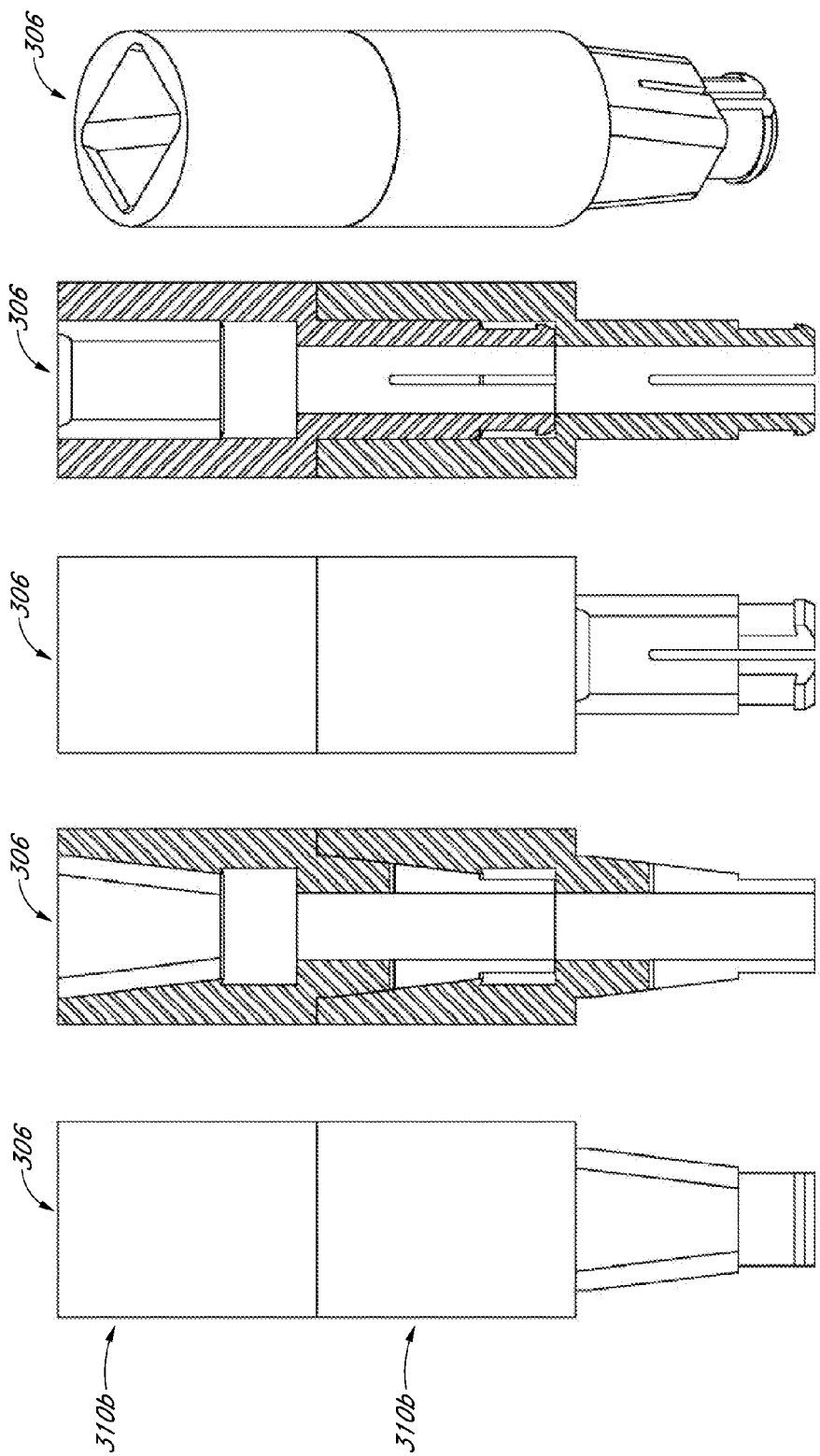
FIG. 46A is a schematic side view of an embodiment of a pair of adjacent snap segments of FIG. 44A in a straightened configuration.
FIG. 46B is a schematic cross-sectional view of the pair of adjacent snap segments of FIG. 44A in a straightened configuration.
FIG. 46C is a schematic front view of the pair of adjacent snap segments of FIG. 44A in a straightened configuration.
FIG. 46D is a schematic cross-sectional front view of the pair of adjacent snap segments of FIG. 44A in a straightened configuration.
FIG. 46E is a schematic perspective view of the pair of adjacent snap segments of FIG. 44A in a straightened configuration.

With reference to FIGS. 41A-C, in one embodiment, a stepped segment 310a can be distracted or pulled apart axially to allow two or more stepped segments 310a to bend in one plane. In one embodiment a stepped segment 310a can be distracted or pulled apart axially to allow two or more stepped segments 310a to bend about one axis. With reference to FIGS. 42A-C in one embodiment, a pair of stepped segments 310a are bent with respect to each other. With reference to FIGS. 43A-C in one embodiment, a pair of stepped segments 310a are in axial alignment with respect to each other in a straightened configuration.

With reference to FIGS. 44A-E, in one embodiment a snap segment 310b has male mating section 320b with a flat feature 321b and a taper feature 322b and a female mating section 330b with a flat feature 331b and a taper feature 332b which are configured to allow bending in one plane when at least partially distracted. In one embodiment the taper features 322b and 332b enable easier engagement of the adjacent segments 310b when they are compressed together. The snap feature 323b provides for ease of assembly of adjacent snap segments 310b. The snap feature 323b can also lock to retain adjacent snap segments 310b together so they do not fall apart when the assembly is distracted, moved or subjected to tensile forces. In one embodiment a snap segment 310b can be distracted or pulled apart axially to allow two or more snap segments 310b to bend in one plane. In one embodiment a snap segment 310b can be distracted or pulled apart axially to allow two or more snap segments 310b to bend about one axis. With reference to FIGS. 45A-E in one embodiment, a pair of snap segments 310b are bent with respect to each other in the side view in FIGS. 45A-45B but remain straight and distracted in the front view in FIGS. 45C-45D. In one embodiment, segments may be distracted from one view while bent from another view. Although the segments are bent with respect to each other, the rotational displacement may occur substantially within one only one plane. With reference to FIGS. 46A-E in one embodiment, a pair of snap segments 310b are in axial alignment with respect to each other in a straightened configuration. In one embodiment, adjacent snap segments 310b have corresponding taper features 322b and 332b to enable easier engagement of the snap segments 310b when they are compressed together. The snap feature 323b allows the segments 310b to be assembled together easily and retains the snap segments 310b together so they do not fall apart when the assembly is distracted.

With reference to FIGS. 47A-C, in one embodiment a unidirectional segment 310c has a male mating section 320c and a female mating section 330c and a channel 340c. Adjacent unidirectional segments 310c can be mated together and a pin 361 (not illustrated here) is placed in a pin hole 337 to retain the unidirectional segments 310c together. In one embodiment a step surface 324c is slideably and/or rotationally moveable with respect to the pin 361 allowing the pin 361 to keep the segments 310c from falling apart while allowing movement to actuate the system between straightened and bent configurations. In various embodiments, interaction between the pin 361 and step surface 324c can be configured to adjust or determine the axial, bend, and/or rotational range of motion of the segments with respect to each other.

Figure 50C:
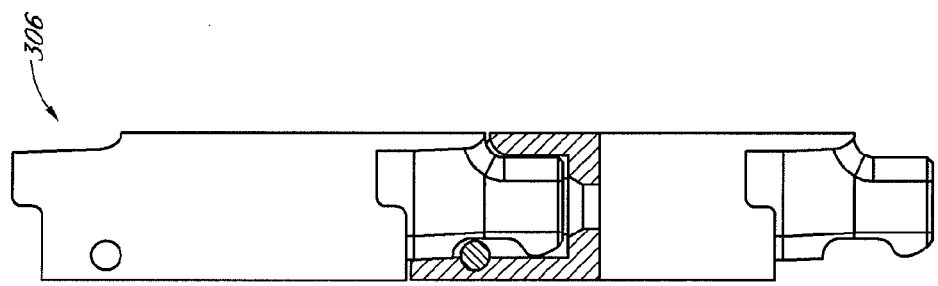
FIG. 50C is a schematic partial perspective side view of the pair of adjacent unidirectional segments of FIG. 48A in a straightened configuration.
Figure 50B:
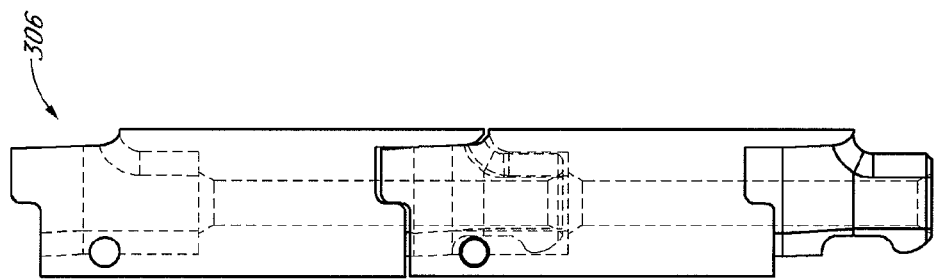
FIG. 50B is a schematic transparent cross-sectional side view of the pair of adjacent unidirectional segments of FIG. 48A in a straightened configuration.
Figure 50A:
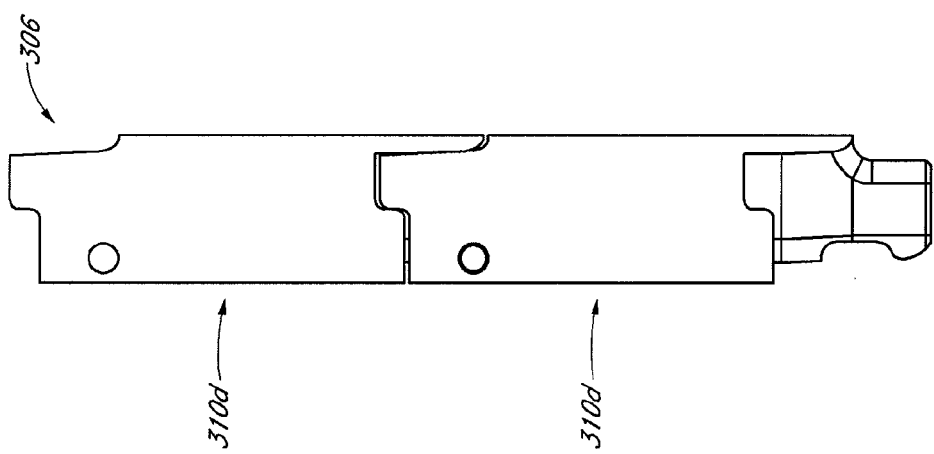
FIG. 50A is a schematic side view of an embodiment of a pair of adjacent unidirectional segments of FIG. 48A in a straightened configuration.

With reference to FIGS. 48A-C, in one embodiment a unidirectional segment 310d has a male mating section 320d and a female mating section 330d and a channel 340d. In one embodiment unidirectional segment 310d is similar to unidirectional segment 310c, but is longer. In one embodiment, a slight taper on both the male and female mating sections, 320d and 330d respectively, keeps the parts locked together tightly and greatly reduces play between the unidirectional segments 310d when they are assembled with a tensioned elongate member 350. Adjacent unidirectional segments 310d can be mated together and a pin 361 (not illustrated here) is placed in a pin hole 337 to retain the unidirectional segments 310d together. In one embodiment a step surface 324d is slideably and/or rotationally moveable with respect to the pin allowing the pin to keep the unidirectional segments 310d from falling apart while allowing movement to actuate the system between straightened and bent configurations. In one embodiment, the step surface 324d is located in a plane perpendicular to the plane of bending, and strengthens the assembled intramedullary structure in bending and also serves as a stop when the assembled intramedullary structure is bent. This allows the bent intramedullary structure to be pushed into the intramedullary canal without the unidirectional segments 310d seating. The assembled intramedullary structure 300d is bent by pulling the unidirectional segments 310d apart longitudinally and then bending or rotating the unidirectional segments 310d with respect to each other. In one embodiment the unidirectional segments 310d are designed such that bending mainly occurs in one direction. With reference to FIGS. 49A-C in one embodiment a pair of unidirectional segments 310d are bent with respect to each other. With reference to FIGS. 50A-C in one embodiment, a pair of unidirectional segments 310d are in axial alignment with respect to each other in a straightened configuration.

With reference to FIGS. 51A-C, in one embodiment a threaded segment 310e has a male mating section 320e, a male threaded section 325e, a female mating section 330e, a female threaded section 335e, an articulation chamber 333e, and a channel 340e. Adjacent threaded segments 310e can be assembled by threading the male threaded section 325e of a first threaded segment 310e into the female threaded section 335e of a second threaded segment 310e. In one embodiment, after threading the male threaded section 325e of a first threaded segment 310e through the female threaded section 335e of a second threaded segment 310, the male threaded section 325e and a portion of the male mating section 320e can move within an articulation chamber 333e. In various embodiments the articulation chamber 333e is sized and configured to allow motion in one, two, three or more planes. In one embodiment the articulation chamber 333e is sized and configured to allow rotation between adjacent first and second segments 310e. In one embodiment the male threaded section 325e and the female threaded section 335e is designed such that as they reach the last half (½) to quarter (¼) turn there is a small amount of interference between the male and female portions to help secure the threaded segments 310e together. As the adjacent threaded segments 310e are forced past this interference the male threaded section 325e drops into the articulation chamber 333e. In one embodiment the articulation chamber 333e is an undercut area in the female mating section 330e of the mating part. The adjacent threaded segments 310e then cannot be disassembled by pulling axially but must be unthreaded and forced past the point of interference again. This feature keeps the adjacent threaded segments 310e together unless they are deliberately disassembled. In one embodiment there is a slight taper on both the male mating section 320e and female mating section 330e which keeps the adjacent threaded segments 310e locked together tightly and reduces or eliminates play between the adjacent threaded segments 310e when they are assembled with a tensioned elongate member 350.

Figure 53C:
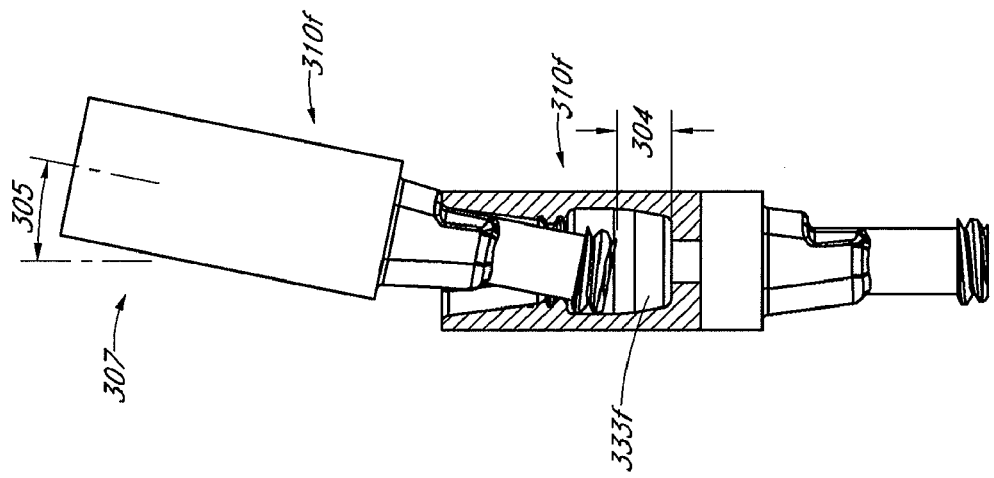
FIG. 53C is a schematic partial cross-sectional side view of the pair of adjacent threaded segments of FIG. 52A in a bent configuration.
Figure 53B:
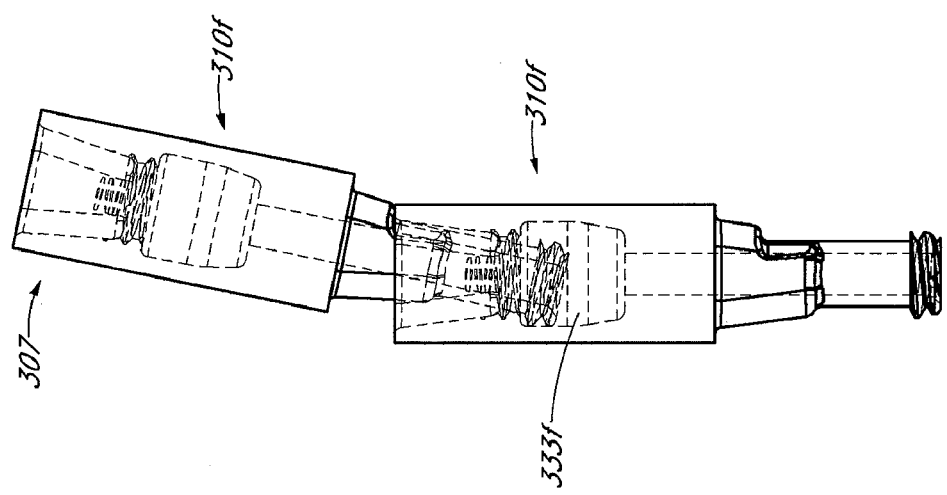
FIG. 53B is a schematic transparent cross-sectional side view of the pair of adjacent threaded segments of FIG. 52A in a bent configuration.
Figure 53A:
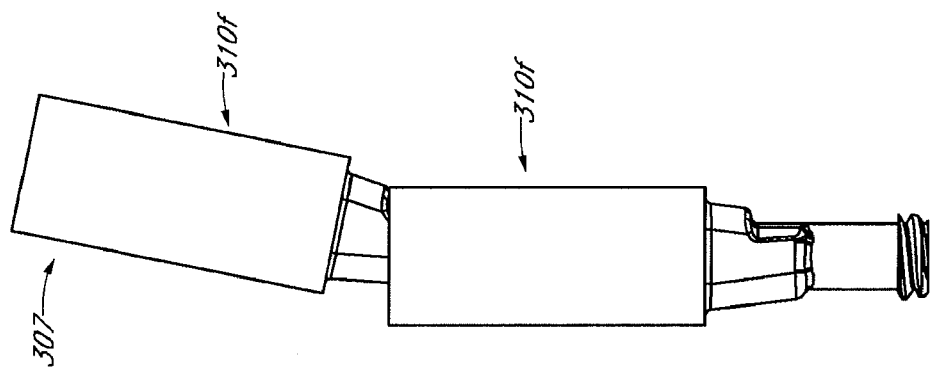
FIG. 53A is a schematic side view of an embodiment of a pair of adjacent threaded segments of FIG. 52A in a bent configuration.

With reference to FIGS. 52A-C, in one embodiment a threaded segment 310f has a male mating section 320f, a male threaded section 325f, a female mating section 330f, a female threaded section 335f, an articulation chamber 333f, and a channel 340f and is similar to threaded segment 310e but also comprises a step surface 324f on the male mating section 320f that allows adjacent threaded segments 310f to bend more in one direction than another, and can also serve as a stop when the threaded segments 310f of an intramedullary structure 300f are bent. This allows the bent intramedullary structure to be pushed into the intramedullary canal without the threaded segments 310f seating. The assembled intramedullary structure 300f is bent by pulling the threaded segments 310f apart longitudinally and then bending or rotating the threaded segments 310f with respect to each other. In one embodiment the threaded segments 310f are designed such that bending mainly occurs in one direction. With reference to FIGS. 53A-C in one embodiment a pair of threaded segments 310f are bent with respect to each other. With reference to FIGS. 54A-C in one embodiment, a pair of threaded segments 310f are in axial alignment with respect to each other in a straightened configuration.

In one embodiment a snap ring segment 310g of a segmented intramedullary structure 300 can be configured to connect with an adjacent snap ring segment 310g with a snap ring 323g. In various embodiments, the snap ring 323g is a separate and moveable component from the two adjacent snap ring segments 310g, allowing a range of relative movement between the two adjacent snap ring segments 310g. In one embodiment the snap ring 323g is moveable with respect to both the adjacent snap ring segments 310g. The snap ring segment 310g in FIGS. 55A-E is illustrated without a snap ring 323g. For some illustrations of an embodiment of a snap ring 323g, see FIGS. 56B, 56D, 57B and 57D.

In one embodiment the snap ring segment 310g includes a distal end 326, a proximal end 336, a male mating section 320g, a female mating section 330g, and a central lumen or channel 340g extending through a longitudinal axis of the snap ring segment 310g. In the illustrated embodiment in FIGS. 55A-E, the male mating section 320g is at the distal end 326 and the female mating section 330g is at the proximal end 336. In another embodiment, the male mating section 320g can be at the proximal end 336 and the female mating section 330g is at the distal end 326. The external surfaces of the male mating section 320g are configured to interface with the internal surfaces of the female mating section 330g, along the channel 340g.

In one embodiment a snap segment 310g has male mating section 320g with a flat feature 321g and a taper feature 322g and a female mating section 330g with a flat feature 331g and a taper feature 332g which are configured to allow bending in one plane when at least partially distracted. In one embodiment a snap ring segment 310g can have one or more flat features 321g, 331g along one or more surfaces to limit or substantially restrict relative lateral motion between adjacent snap ring segments 310g to relative motion between the segments 310g in a single plane or an axis substantially parallel to the flat feature 321g, 331g. In various embodiments, a maximum rotational displacement angle 305 (see FIG. 56B) along a flat feature 321g in a compressed configuration 306 is no more than about zero degrees, 0.5 degrees, 1 degree, 2 degrees, 3 degrees, or 5 degrees or less. In various embodiments, a maximum rotational displacement angle 305 along a flat feature 321g in a distracted configuration 308 or a bent configuration 307 can be no more than about 0.5 degrees, 1 degree, 5 degrees, 15 degrees, or 20 degrees or less.

In one embodiment a snap ring segment 310g can have a taper feature 322g, 332g along one or more surfaces to help seat adjacent snap ring segments 310g with each other when in a straightened, rigid or an axially compressed configuration. In various embodiments, a maximum rotational displacement angle 305 along a taper feature 322g in a compressed configuration 306 can be no more than about zero degrees, 0.5 degrees, 1 degree, 2 degrees, 3 degrees, or 5 degrees or less.

In one embodiment a snap ring segment 310g can have one or more flat features 321g and one or more taper features 322g along the surfaces defining central lumen or channel 340g that are configured to allow bending between adjacent segments of the segmented intramedullary structure 300 in only a single plane when the adjacent segments are at least partially distracted and/or bent with respect to each other. In various embodiments, a maximum rotational displacement angle 305 along a taper feature 322g in a bent configuration 307 can be 1 degree, 3 degrees, 5 degrees, 10 degrees, 20 degrees, 30 degrees, 45 degrees, or 60 degrees or less.

In one embodiment corresponding taper features 322g, 332g enable easier engagement of the adjacent snap ring segments 310g when they are compressed together. In one embodiment the male mating section 320g includes one or more taper features 322g configured to interface with one or more taper features 332g on the female mating section 330g.

In various embodiments segments 310 can have various features along the chamber 340 and the outside surfaces. In various embodiments, surfaces may have chamfers, radii, or other transition structures. As illustrated in one embodiment illustrated at FIG. 55B, starting at the proximal end 336 of the chamber 340g, the snap ring segment 310g female mating section 330g has a proximal chamber edge 360 and a proximal chamber surface 362. In some embodiments, the proximal chamber surfaces 362 can be substantially linear and inclined from the longitudinal axis to provide a frusto-conical chamber increasing in inside diameter in the proximal direction.

In one embodiment a first articulation chamber 333g has proximal transverse stop or surface 364, a first articulation wall surface 366, and a distal surface 368. An optional second articulation chamber 334g has proximal stop or surface 372, a second articulation wall surface 374, and a distal stop or surface 376. The stop surfaces on articulation chambers 333g and 334g may be in the form of an annular shelf or transverse surface residing on a plane transverse to the longitudinal axis.

The chamber 340g surface continues to extend from the female mating section 330g into the male mating section 320g with lumen surface 378, which extends toward the distal end 326 of the snap ring segment 310g. In one embodiment the exterior of the male mating section 320g has a distal end surface 380, a distal lip wall 382, a distal snap ring articulation surface 384, a snap ring articulation wall surface 386, a proximal snap ring articulation surface 388, step surface 324g, a proximal step surface edge 392, a distal male exterior surface 390 and a distal male exterior surface edge 394. In various embodiments, the distal male exterior surfaces 390 can be a linear or flat feature 321g parallel to the longitudinal axis or a taper feature 322g, inclined with respect to the longitudinal axis and decreasing in a transverse dimension in the distal direction.

With reference to FIGS. 56A-E in one embodiment, a pair of snap ring segments 310g in a bent configuration 307 are rotated with respect to each other in the side view in FIGS. 56A-56B but remain substantially axially aligned in the front view in FIGS. 56C-56D. With reference to FIGS. 57A-E in one embodiment, a pair of snap ring segments 310g are in axial alignment with respect to each other in a compressed configuration 306. In one embodiment the snap ring 323g allows the snap ring segments 310g to be assembled together easily and retains the snap ring segments 310g together so they do not fall apart when the assembly is distracted.

FIGS. 58A-58D illustrate embodiments of segments 310 in various configurations. FIG. 58A illustrates an embodiment of a pair of segments 310 that are detached. FIG. 58B illustrates an embodiment of a pair of segments 310 that are in an assembled but distracted configuration 308. FIG. 58C illustrates an embodiment of a pair of segments 310 that are in a bent configuration 307. FIG. 58B illustrates an embodiment of a pair of segments 310 that are in a compressed configuration 306. In one embodiment a snap ring 323g is disposed on a snap ring articulation wall surface 386 of a male mating section 320g of a first snap ring segment 310g. The first snap ring segment 310g can be pushed or advanced in to a second snap ring segment 310g, deflecting the snap ring 323g into a radially reduced configuration that snaps back into a radially expanded configuration inside a first articulation chamber 333g or a second articulation chamber 334g. In one embodiment, the snap ring 323g permanently connects the adjacent segments 310g together so that the adjacent segments 310g do not detach from each other.

In one embodiment the snap ring 323g (see FIGS. 56A-58D) provides for ease of assembly of adjacent snap ring segments 310g. The snap ring 323g can also lock to retain adjacent snap ring segments 310g together so they do not fall apart when the segmented intramedullary structure 300 is distracted, moved or subjected to tensile forces. In one embodiment a snap ring segment 310g can be distracted or pulled apart axially to allow two or more snap ring segments 310g to bend in one plane. In one embodiment a snap ring segment 310g can be distracted or pulled apart axially to allow two or more snap ring segments 310g to bend about one axis.

In one embodiment the snap ring 323g is an annular or arcuate length of a resilient material such as stainless steel, Nitinol, Titanium, a Titanium alloy, or other material with an open section configured to allow a certain range of bending or flexing or temporary deformation of the snap ring 323g in order to snap the snap ring 323g in to a location. In one embodiment snap ring 323g is a C-shaped ring and serves to create an interference fit between adjacent snap ring segments 310g to permanently join them together. In various embodiments snap rings 323g are sized proportionately depending on the size of the snap ring segments 310g being joined. In one embodiment the snap ring 323g has a feature for assisting in the removal of the snap ring 323g from the location. In one embodiment a snap ring 323g is disposed to be rotatable, and axially slideable along the snap ring articulation wall surface 386 at least between the distal snap ring articulation surface 384 and the proximal snap ring articulation surface 388. In one embodiment a snap ring 323g is configured to stop or limit motion against one or more surfaces in one or more articulation chambers 333g, 334g. In one embodiment a snap ring 323g can be configured to stop against a surface in order to connect adjacent snap ring segments 310g while limiting the relative motion between the adjacent snap ring segments 310g. For example, in various embodiments a snap ring 323g is configured to stop against a proximal surface 364 of a first articulation chamber 333g and a distal snap ring surface 384 to prevent adjacent snap ring segments 323g from detaching from each other as illustrated in FIGS. 56B, 56D and 58B.

In one embodiment a snap ring 323g is configured to stop against a distal surface 368 of a first articulation chamber 333g and a proximal snap ring articulation surface 388 to limit the compression of adjacent snap ring segments 323g. In one embodiment a distal end surface 380 of a male mating section 320g contacts a distal surface 376 of a second articulation chamber 334g to limit the compression of adjacent snap ring segments 323g.

In one embodiment the step surface 324g is slideably and/or rotationally moveable with respect to the distal chamber surface 362 and the distal chamber edge 360. For example, in an embodiment with two adjacent segments 310, there is a proximal segment and a distal segment. In one embodiment of a compressed configuration, the distal male exterior surface edge 394 of the proximal segment is close to or in complementary contact with distal chamber edge 360 of the distal segment. In articulating the proximal segment and the distal segment between the compressed and the bent configurations (see FIGS. 57B and 56B, respectively), the distal lip wall 382 of the proximal segment's male mating section 320g moves in a proximal direction through the second articulation chamber 334g with respect to the distal segment. The distal lip wall 382 of the proximal segment's male mating section 320g can move in a proximal direction through the second articulation chamber 334g and into the first articulation chamber 333g. As the proximal segment moves away from the distal segment, the tapered features 322g open up and get wider to allow the proximal segment to rotate or bend substantially within a plane parallel to flat features 321g in the male and female mating sections 320g and 330g. In one embodiment of the bent configuration 306, the proximal step surface edge 392 of the proximal segment is close to or in contact with distal chamber edge 360 of the distal segment.

In various embodiments, interaction between features on the interior and/or exterior surfaces of adjacent segments 310 can be configured to adjust or determine the axial distraction range of motion and/or rotational bending range of motion of the segments 310 with respect to each other. For example, in various non-limiting embodiments the axial displacement length 304 and/or the rotational displacement angle 305 can be altered by changing tapers, radii, dimensions of parts, or features, such as changing the snap ring 323g thickness, changing the distance between the proximal step surface edge 392 and the distal male exterior surface edge 394 on a snap ring segment 310g, changing the distance between the proximal snap ring surface 388 and the distal snap ring surface 384 on a snap ring segment 310g, or changing the first articulation chamber 333g height (distance from proximal surface 364 and distal surface 368).

Referring to FIGS. 58B-58D, operation of the segmented intramedullary structure 300 implant is best illustrated. In FIG. 58B, a first, proximal segment 310g is interlocked with a second, distal segment 310g, and placed under axial traction. Proximal movement of the proximal segment 310g causes surface 384 to advance snap ring 323g to the proximal limit of travel within first articulation chamber 333g. At that point, further relative axial distraction of the two segments is limited by stop surface 364. In this distracted configuration 308, the two segments 310 may be inclined with respect to each other, enabling the assembled implant to be bent into a curved configuration 307, such as for implantation around a curve, and to facilitate removal as will be discussed below.

In one embodiment during implantation, the implant needs to be able to be placed under axial compression as it is advanced around a curve. This is permitted as seen in FIG. 58C, with the distally facing proximal step surface edge 392 engaging proximally facing proximal chamber edge 360 to permit axial compression without axial shortening of the implant, and simultaneously permit axial compression while permitting the implant to retain a curve.

Once the implant has reached the approximately linear configuration of the intramedullary canal, distally facing proximal step surface edge 392 disengages laterally from proximally facing proximal chamber edge 360 as the angle between the two segments 310 decreases. This enables the proximal segment 310g to axially advance further into distal segment 310g under further axial compression such as by pushing distally on a deployment tool, as illustrated in FIG. 58D. As seen therein, the complementary internal surfaces of the two segments 310 urge the axially compressed construct into a linear or substantially linear predetermined configuration.

Thus, the implant has a first length, when under axial tension as illustrated in FIG. 58B. The implant can be shortened to a second length upon application of an axially compressive force, while the implant is in a nonlinear configuration as illustrated in FIG. 58C. The implant can be further axially shortened to a third length by applying an axially compressive force while the implant is in a substantially linear configuration as seen in FIG. 58D. Preferably, the implant is thereafter locked in the axially compressed and linear configuration of FIG. 58D such as by applying axial tension on a tightening elongate member 350 as is discussed elsewhere herein.

When removal is desired, proximal traction on a proximal segment 310 may be applied as will be discussed in additional detail below. Once the proximal segment 310 has broken free of any bony ingrowth that may have occurred, it will advance proximally to the proximal limit of travel as illustrated in FIG. 58B. This enables further proximal traction on the proximal segment 310 to be transferred on the next segment 310 in the distal direction along the length of the implant 300. In this manner, a proximal, removal force can be transmitted directly from segment 310 to segment 310 along the length of the implant 300, in addition to or in place of reliance on the tensioning elongate member 350 extending through central lumen or channel 340g.

In one embodiment a segmented intramedullary structure 300 comprises a segment construct 303. The segment construct 303 comprises two or more segments 310 including a distal end segment 400 and a proximal end segment 500. In various embodiments, segments 310 can also comprise one or more transition segments 314 and/or uniform segments 316 disposed between the distal end segment 400 and the proximal end segment 500.

In one embodiment transition segment 314 has a varying outer nominal diameter or width dimension, and is configured to provide a transition between segments 310 with different outer nominal diameter or width dimensions. A plurality of transition segments 314 may be used to transition across nominal dimensions in incremental transition steps. For example, in the illustrated embodiment of FIGS. 56A-H, two transition segments 314 are used to transition from a nominal width or diameter dimension from the proximal end segment 500 to a uniform segment 316. In various embodiments, different combinations of transition segments 314 can be used to transition between a plurality of nominal segment 310 dimensions. In one embodiment, the nominal dimension changes can be gradual, such as with a smooth taper. In one embodiment one or more transition segments 314 taper distally and serve to gradually reduce the outer diameter of the segment construct 303. For example, in one embodiment, three transition segments 314 can be used to transition the body of the segment construct 303 down from an 11 mm diameter of one embodiment of a proximal end segment 500 to one embodiment of a uniform segment 316 nominal diameter of 8.0 mm diameter. The transition segments 314 can include an 11 to 10 mm transition segment 314, a 10 to 9 mm, and a 9 to 8 mm transition segment 314.

In one embodiment uniform segment 316 has a uniform outer nominal diameter or width dimension. In one embodiment a uniform segment 316 has a fixed diameter. In one embodiment a uniform segment 316 is a straight segment. In one embodiment a uniform segment 316 is a curved segment. In various embodiments distal end segment 400 and proximal end segment 500 are configured with a male mating section 320 or a female mating section 330 that corresponds to the mating structure of an adjacent segment 310. In various embodiments the proximal end segment 500 and/or the distal end segment 400 can have a transition in nominal outer dimension width or diameter. In one embodiment the distal end segment 400 tapers distally.

Figure 59G:
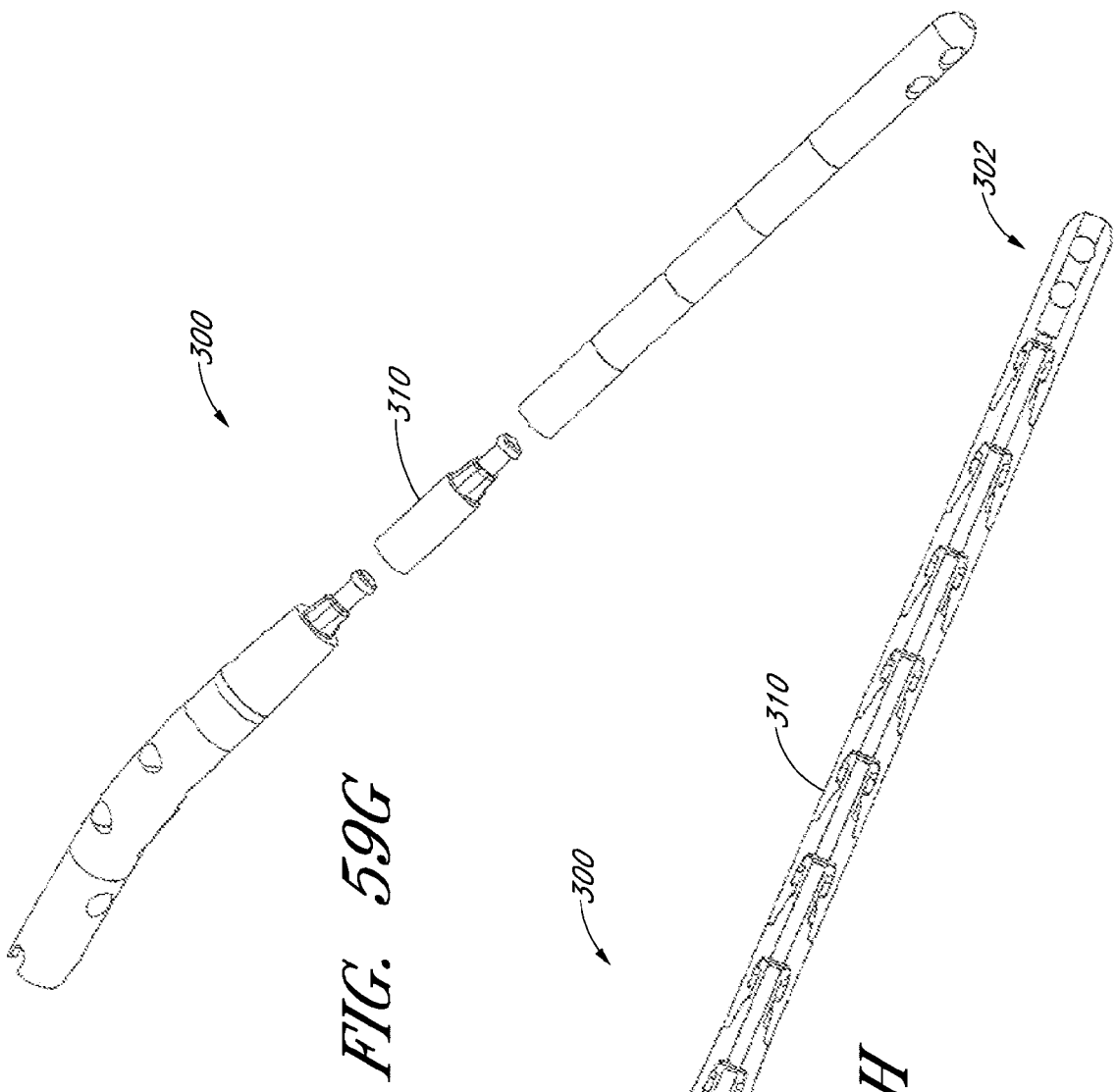
FIG. 59G is a schematic perspective partially exploded view of the segmented intramedullary structure of FIG. 59A.
Figure 59H:
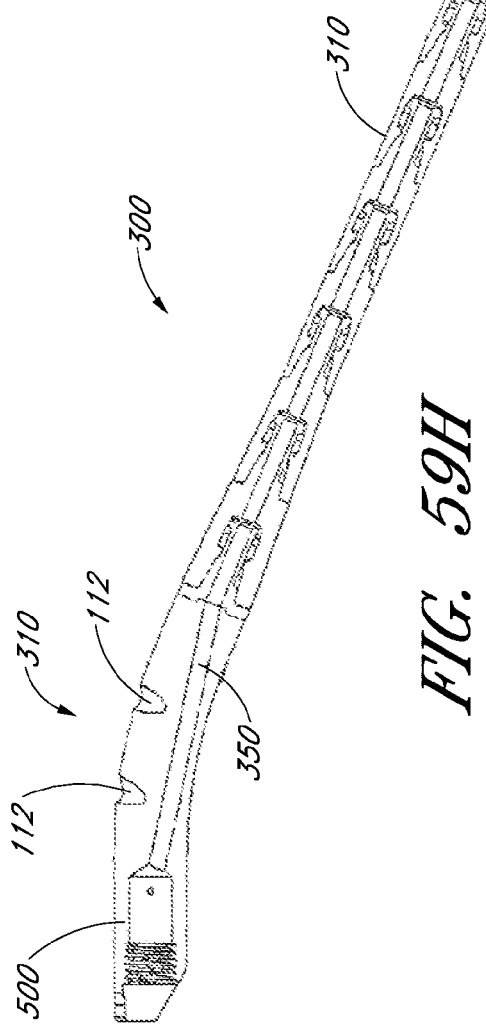
FIG. 59H is a schematic cross-sectional side view of the segmented intramedullary structure of FIG. 59A.

The segment construct 303 is configured to be changeable between a relatively flexible, bent configuration 307 for insertion or extraction through a hole in an intramedullary canal and a relatively rigid, or less flexible compressed configuration 306 to provide a relatively stable anchor or fixation feature for the treatment of bone. FIGS. 59A-H illustrate various views of an embodiment of a segmented intramedullary structure 300 in a compressed configuration 306. FIG. 59G is a schematic perspective partially exploded view of the segmented intramedullary structure 300 with a elongate member 350 extending between a proximal end 301 and distal end 302 of the intramedullary structure 300 through the channels 340 of the segments 310.

Figure 60:
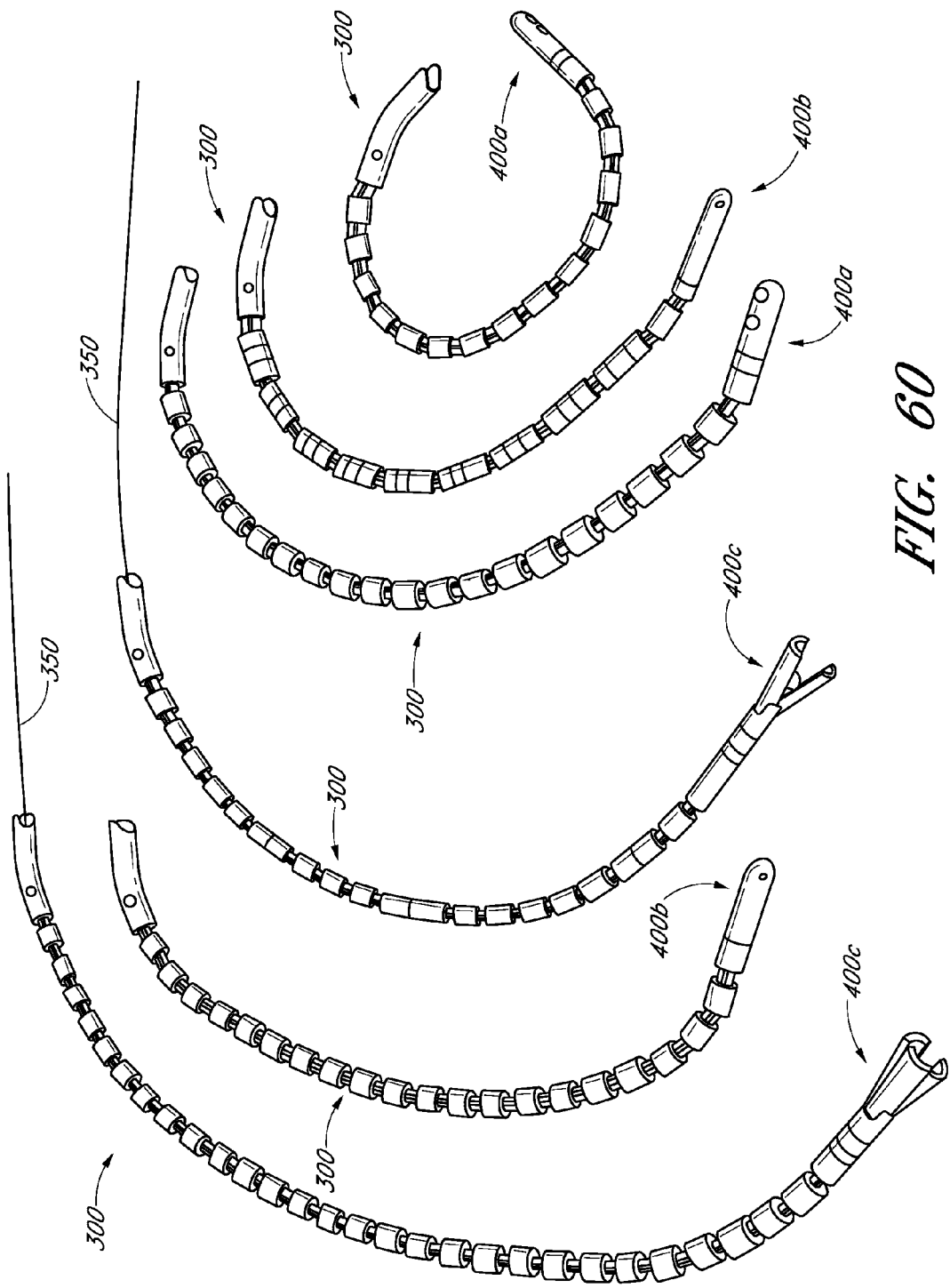
FIG. 60 is a schematic side view of various embodiments of segmented intramedullary structures in bent configurations.
Figure 61:
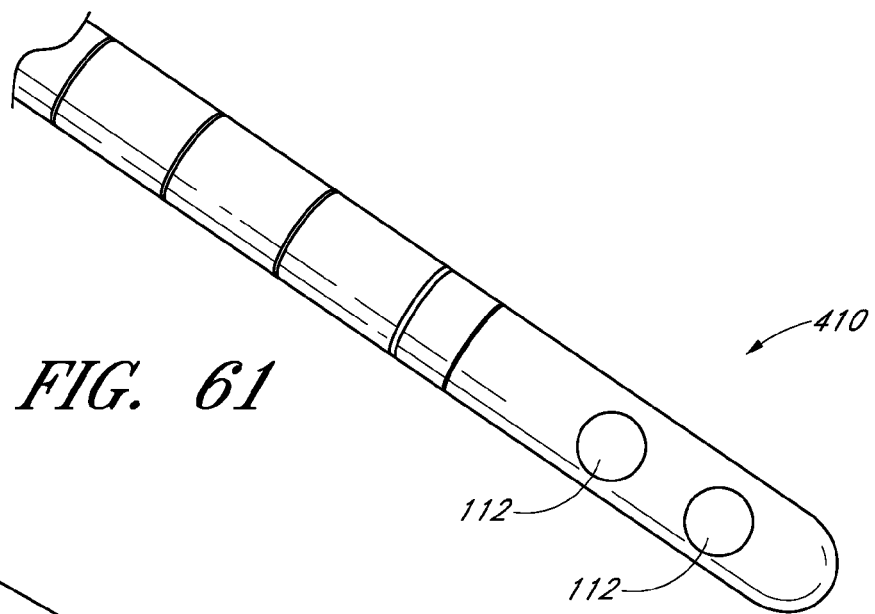
FIG. 61 is a schematic perspective view of an embodiment of a cross-screw distal fixation structure segment of an intramedullary structure.
Figure 62:
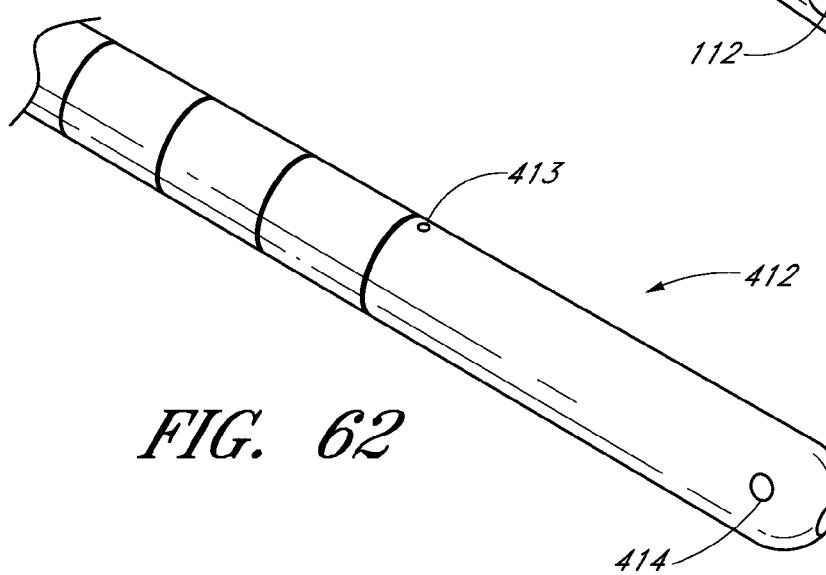
FIG. 62 is a schematic perspective view of an embodiment of a polymer distal fixation segment of an intramedullary structure.
Figure 63:
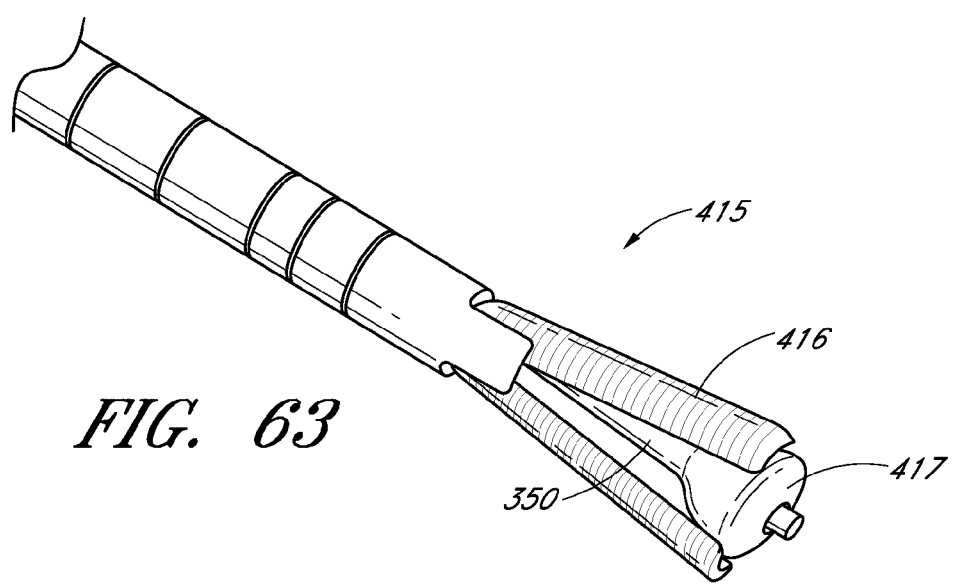
FIG. 63 is a schematic perspective view of an embodiment of a radially-expandable distal fixation segment of an intramedullary structure.

FIG. 60 illustrates various embodiments of segmented intramedullary structures 300 in various bent configurations 307 with various lengths, diameters, materials and distal end segments 400 with various embodiments of distal fixation structures. Although certain embodiments of proximal and distal fixation structures in proximal end segments 500 and distal end segments 400 may show one fixation embodiment, any of the disclosed fixation structures can be mixed or used in combination with other or the same type of fixation structures on the proximal, distal, and/or intermediate portion of any embodiment of segmented intramedullary structures 300. FIGS. 61-63 illustrate various embodiments of distal end segments 400 of segmented intramedullary structures 300 with various embodiments of distal fixation structures.

FIG. 61 illustrates one embodiment of a cross-screw distal fixation structure segment 410 of an intramedullary structure has one or more pre-formed or pre-drilled cross throughbores 112 for a surgeon to use in securing the distal end in the bone by using one or more bone screws 113 through the bone and into one or more cross-holes at various angles to anchor and secure the distal end of the implant in the bone. In various embodiments, bone screw 113 is the same or similar to locking bolt 54 and/or locking bolt 60. In one embodiment bone screw 113 is a locking screw. In one embodiment bone screw 113 is a self-tapping screw. In one embodiment bone screw 113 uses an internal hex interface for driving the screw. In various embodiments bone screw 113 can have a major diameters and lengths and screwing interfaces configured for a particular application. In various embodiments a bone screw 113 has a major diameter of 4 mm, 5 mm, 6 mm, or other diameters. In various embodiments a bone screw has a length in the range of approximately 16 to 120 mm. In one embodiment at least one bone screw 113 is used in at least one throughbore 112 at the distal end segment 400. In one embodiment at least one bone screw 113 is used in at least one throughbore 112 at the proximal end segment 500. In various embodiments, one, two, three, four or more through holes 112 are provided in any segment 310. In one embodiment a throughbore 112 is a tunnel in a segment 310. In one embodiment throughbore 112 may merge with another throughbore 112 to form a multi-conduit pathway. Different throughbores 112 may be used or optionally provided for options in fixing the device to bone.

FIG. 62 illustrates one embodiment of a polymer distal fixation segment 412 of an intramedullary structure 300 that includes a strong, solid polymer tip. In one embodiment the polymer is implantable-grade polyetheretherketone (PEEK), or other similar materials. One advantage of a polymer distal fixation structure segment 412 is that the surgeon can pierce the polymer distal fixation segment 412 in any angle or direction to provide cross-screw fixation between the bone and implant. In one embodiment one or more bone screws 113 are used to provide structure between one side of the cortical bone, through the polymer distal fixation segment 412, and into the other side of the cortical bone. For example, see FIGS. 39B and 40B. In one embodiment the polymer distal fixation segment 412 is fixed to the intramedullary structure 300 with a pin 413. In one embodiment the polymer distal fixation segment 412 has one or more markers placed in it for radiopaque monitoring of the fixation process. In one embodiment the marker 414 is near a distal end of the polymer distal fixation segment 412. In one embodiment the marker can be a ring or other structure or shape for visualization under monitoring devices such as fluoroscopy.

With respect to FIG. 63, one embodiment of a radially-expandable distal fixation segment 415 of an intramedullary structure can be called "hinged fingers." In one embodiment, radially-expandable distal fixation segment 415 is the same or has similar features to an embodiment of the radially-expandable distal end segment 114 described above. In one embodiment, a radially-expandable distal fixation segment 415 comprises two or more rigid members 416 (also called hinged fingers) that can open up like a flower when the ball (or actuator 417) at the end of the elongate member 350 is pulled up proximally through the intramedullary structure. One embodiment includes three or more rigid members 416. In one embodiment the rigid members 416 do not bend. One embodiment has metal rigid members 416. In one embodiment one or more hinged finger members 416 have a surface texture configured to improve fixation to bone. In one embodiment the surface texture is grooves. In one embodiment, the ball 417 is attached to the distal end of the elongate member 350. When the elongate member 350 is pulled proximally toward the proximal end 301 of the segmented intramedullary structure 300 the ball moves proximally until the hinged fingers 416 seat on sufficiently stable bone in or around the intramedullary canal. In one embodiment the ball 417 can move off the central longitudinal axis of the intramedullary device since the elongate member 350 is flexible, allowing the ball 417 to apply pressure to actuate the various hinged fingers 416 until a sufficient number of hinged fingers 416 is properly anchored, irrespective of irregular bony geometry in the intramedullary canal. This self-centering aspect of the ball 417 and elongate member 350 is another advantage of the present embodiment.

In one embodiment distal end segment 400 has a proximal end 401 and a distal end 402. In one embodiment distal end segment 400 has a male or female end portion configured for attachment with an adjacent, proximal segment 310. In one embodiment the proximal end 401 of the distal end segment 400 has a female mating section 430 similar to any embodiment of a female mating section 330 in a segment 310. In one embodiment distal end segment 400 has a channel 440 extending longitudinally therethrough. In one embodiment channel 440 is similar to channel 340 in a segment 310. In one embodiment channel 440 is configured to align with and work in conjunction with channel 340 in one or more segments 310 and an elongate member 350. In one embodiment a distal end segment 400 is configured to distally anchor an elongate mechanism, such as a tensioning rod 14, threaded rod, or elongate member 350.

In one embodiment elongate member 350 is flexible. In one embodiment elongate member 350 comprises a braided cable 352. In one embodiment elongate member 350 comprises a metal cable. In one embodiment elongate member 350 comprises a braided Titanium cable. In one embodiment elongate member 350 serves as a post-reaming guide for placing the segmented intramedullary structure 300 into an intramedullary canal 40 of a bone 42. In one embodiment the elongate member 350 is inserted through an entry point in the cortical bone in to the intramedullary canal 40 and distally past a fracture site 44 in a bone 42.

In one embodiment elongate member 350 comprises a ferrule 356 at the distal end of the elongate member 350. In one embodiment ferrule 356 is attached to the distal end of the braided cable 352. In one embodiment ferrule 356 is crimped to the distal end of the braided cable 352. In one embodiment ferrule 356 is welded to the distal end of the braided cable 352. In one embodiment ferrule 356 is crimped and welded to the distal end of the braided cable 352. In one embodiment ferrule 356 serves as a stop at the end of the elongate member 350. In one embodiment ferrule 356 is a Titanium alloy.

In one embodiment elongate member 350 comprises a braided cable 352 at least partially disposed within a lumen of a tube 354. See FIGS. 65 and 65A. In one embodiment the tube 354 is flexible. In one embodiment the tube 354 is a Nitinol tube. In one embodiment the tube 354 has an outer diameter of 0.085", an inner diameter of 0.065", and a wall thickness of 0.010". In one embodiment the tube 354 stiffens the elongate member 350 to facilitate the insertion of the segmented intramedullary structure 300 over the elongate member 350, across the fracture site 44. In one embodiment the super elastic properties of Nitinol can prevent or minimize the permanent deformation of the elongate member 350 if bending of the elongate member 350 at the fracture site 44 occurs. In one embodiment the tube 354 runs from the distal end of the elongate member 350 to just below the proximal end segment 500 when the segmented intramedullary structure 300 is fully compressed.

In one embodiment the elongate member 350 is tensioned to compress the implant segments 310 together to form a relatively rigid construct. In one embodiment the proper placement of the segmented intramedullary structure 300 can be confirmed with fluoroscopy prior to the tensioning of the elongate member 350. In one embodiment the elongate member 350 is manually tensioned. In one embodiment the elongate member 350 is manually tensioned by pulling proximally on the elongate member 350 with respect to the segmented intramedullary structure 300. In one embodiment the elongate member 350 is tensioned or further tensioned with a cable tensioner assembly 200. In one embodiment, when fully tensioned, the elongate member 350 is locked in place with a collet screw 280 in the proximal end segment 500. In one embodiment an end cap 290 is placed and then the elongate member 350 is cut flush with the top of the end cap 290. In one embodiment, when the elongate member 350 is fully tensioned and the segmented intramedullary structure 300 becomes rigid, the tube 354 is enclosed by the segmented intramedullary structure 300 and is no longer is loaded. In various embodiments, distal end segment 400 can be any of the embodiments of a distal end segment. In one embodiment illustrated at FIG. 64, the distal end segment 400 can be a cross-screw distal fixation structure segment 410.

In one embodiment the proximal end segment 500 has a proximal end 501 and a distal end 502 with a channel 540 extending between the proximal end 501 and distal end 502. FIGS. 66-68 illustrate one embodiment of a proximal end segment 500. In one embodiment the proximal end segment 500 has a proximal section 510 near the proximal end 501. In one embodiment the proximal end segment 500 has a distal section 520 near the distal end 502. In one embodiment the proximal end segment 500 has a throughbore section 530 between the proximal end 501 and distal end 502. In one embodiment distal section 520 has a male or female end portion configured for attachment with an adjacent, distal segment 310. In one embodiment the distal end 502 of proximal end segment 500 has a distal section 520 similar to any embodiment of a male mating section 320 in a segment 310. In various embodiments proximal end segment 500 is has similar features as proximal end segment 110 described above.

In one embodiment the proximal end segment 500 is slightly curved such that its proximal end 501 reaches cortical bone proximal to the fracture site 44 while its distal end is in the intramedullary canal 40. In one embodiment throughbore section 530 has four through-holes, or throughbores 112, to allow for placement of one, two, three or four bone screws 113 at the proximal end 301 of the segmented intramedullary structure 300. In one embodiment, two of the throughbores 112 are oriented for bone screws 113 placed from the right, and two of the throughbores 112 are oriented for bone screws 113 placed from the left.

In one embodiment a cable collet anchor 272 is permanently fixed within the proximal section 510. In embodiment cable collet anchor 272 is permanently fixed within the proximal section 510 with a pin (not illustrated) in a pin hole 511, which can be welded in place after insertion. In embodiment cable collet anchor 272 is permanently fixed within the proximal section 510 by welding. In embodiment cable collet anchor 272 is permanently fixed within the proximal section 510 with an interference fit between the two components. In embodiment cable collet anchor 272 is integral, or unitary, with the proximal section 510.

In one embodiment the cable collet anchor 272 is configured to interface with a cable tensioner assembly 200. In one embodiment interface 512 provides a notch or other feature to facilitate the interfacing or connection between the cable collet anchor 272 and the cable tensioner assembly 200. In one embodiment a cable tensioner assembly 200 is used to tighten, or increase tension in a elongate member 350 in order to make the segmented intramedullary structure 300 less flexible, such as during device implantation. In one embodiment a cable tensioner assembly 200 is used to loosen, or decrease tension in a elongate member 350 in order to make the segmented intramedullary structure 300 more flexible, such as during device extraction.

In one embodiment the cable collet anchor 272 is threaded to mate with the collet screw 280 with a channel 281 configured to grip elongate member 350 with a plurality of flexible fingers 284. In one embodiment the cable collet anchor 272 has one or more tapered walls 276 to force the plurality of flexible fingers 284 to close around the elongate member 350 as the collet screw 280 is tightened by rotating it distally. In one embodiment the outer surface of the flexible fingers 284 are tapered distally. In one embodiment the outer surface of the flexible fingers 284 are substantially cylindrical. In various embodiments the collet screw 280 can have three, four, five or more flexible fingers 284. The illustrated collet screw 280 at FIG. 69 has three flexible fingers 284. In one embodiment a driver shaft 252 of a collet driver 250 can used to tighten or loosen the cable collet screw 280 by interfacing with a cable collet screw interface 283. In one embodiment cable collet screw interface 283 has a shaped inner wall 286. In various embodiments shaped inner wall 286 is a hex shape, or other keyed type shape. In one embodiment cable collet screw interface 283 has a shaped outer wall. In one embodiment the shaped outer wall is a hexagonal shape, such as with a nut.

In one embodiment an end cap 290 serves to prevent bone formation over the device entry point. In various embodiments the end cap 290 can be configured to attach at the distal end 501 of the proximal end segment 500. In various embodiments, the end cap 290 can be offered in various lengths to allow the surgeon to position the end of the end cap 290 so that it is just below the cortical margin. In various embodiments, the end cap 290 can have an additional length of +0 mm, +5 mm, +10 mm, +15 mm, or +20 mm. In one embodiment end cap 290 has external threads that mate with internal threads on the proximal end segment 500. In one embodiment end cap 290 has internal threads that mate with external threads on the proximal end segment 500. In one embodiment end cap 290 has a reversible snap fit connection with the proximal end segment 500. In one embodiment, once the end cap 290 is in place, the elongate member 350 is cut flush with the proximal surface of the end cap 290.

Procedures for Manufacturing, Assembling or Installing a Segmented Intramedullary Structure In various embodiments, steps for installing a segmented intramedullary structure may include optional steps, and steps that can be taken in or out of sequence. Different combinations of steps may be used depending on the segmented intramedullary structure used, patient anatomy, the treatment being provided, and/or medical practitioner preference. As noted above, FIGS. 14-22 schematically illustrate various embodiments of procedures for installing an embodiment of a segmented intramedullary nail into the intramedullary canal of a long bone. The following embodiments of procedures can be used alone, in conjunction with, or in combination with the embodiments of the procedure described with respect to FIGS. 14-22 and described elsewhere herein. FIGS. 70-78 schematically illustrate various embodiments of procedures for installing an embodiment of a segmented intramedullary nail into the intramedullary canal of a long bone.

In one embodiment a technique for implanting a segmented intramedullary structure 300 can include any of the following general steps, such as reaming a canal in tissue to a diameter larger than the diameter of the selected segmented intramedullary structure 300, inserting a elongate member 350 into the prepared canal, placing the selected segmented intramedullary structure 300 over the elongate member 350, pulling on the elongate member 350 to compress the segments 310 together, placing proximal and distal end locking screws 113, tensioning the elongate member 350 with a cable tensioner assembly 200, locking the elongate member 350 by tightening a cable collet screw 280 within the proximal end segment 500, threading an end cap 290 onto the proximal end of the segmented intramedullary structure 300, or cutting the elongate member 350 flush with the end cap 290 with a cable cutter instrument. In one embodiment the technique for implanting a segmented intramedullary structure involves reaming a canal in tissue to a diameter at least 1.0 mm larger than the diameter of the selected segmented intramedullary structure 300. In various embodiments of techniques for implanting a segmented intramedullary structure 300, various instruments can be used. Some non-limiting examples of optional instruments that can be used include a guide wire, a ball-tip guide wire, a Kelly clamp, an exchange tube, a drill bit, a cable tensioner, a reamer, a flexible reamer set, a tissue protector, a guidewire T-handle, an obturator, an implant length gauge, a proximal screw guide, a drill sleeve, a broach trial, a curved broach trial, a screw driver, a cannulated screw driver, a slap hammer, a back slapper, and a cable cutter.

In one embodiment, pre-operative planning includes measuring intramedullary canal 40 diameter and/or length in a bone 42. In one embodiment a radiographic canal ruler can be used to measure intramedullary canal 40 diameter and/or length in a bone 42.

FIG. 70 illustrates one embodiment of an approach to an access site for the implantation or removal of a segmented intramedullary structure 300. In the illustrated embodiment, the bone 42 is a humerus, but the approach can be with any long bone and can occur at a distal or proximal end of the bone 42. In one embodiment, a patient is placed in a supine and in a semi-recumbent position (e.g., traditional "beach chair" position or tilted with the thorax "bumped" 30-40 degrees). A surgeon can split the deltoid fibers longitudinally, taking care to avoid the axillary nerve. In one embodiment, an access hole 46 is created at the access site. The surgeon can create an entry hole or access hole 46 just distal to the insertion of the supraspinatus, below the greater tuberosity.

In one embodiment illustrated at FIG. 71, the surgeon can insert the tip of a broach 604 into the bone 42 at an approximately 45 degree angle to the bone surface, at least 1 cm distal to the rotator cuff insertion. In one embodiment the geometry of the cutting surfaces of the broach 604 matches the proximal geometry of the segmented intramedullary structure 300 to ensure properly sized proximal opening in the bone. In one embodiment, an 11 mm diameter access hole 46 is used. Optionally, a guide wire and/or cone reamer can be used to open the access hole 46 prior to insertion of the broach 604. The surgeon advances the broach 604 into the medullary canal 40.

In one embodiment illustrated at FIG. 72, the surgeon can advance a guide wire 606 into the intramedullary canal 40, manually reduce the fracture 44, then advance the guide wire tip past the fracture site 44. In one embodiment the guide wire 606 has a 2 mm outer diameter. In one embodiment the guide wire 606 includes a ball tip at its distal end. In one embodiment the surgeon can confirm the position of the guide wire 606 using fluoroscopy as needed. In one embodiment the surgeon centers the ball-tip of the guide wire 606 at the distal end of the intramedullary canal 40.

Figure 73:
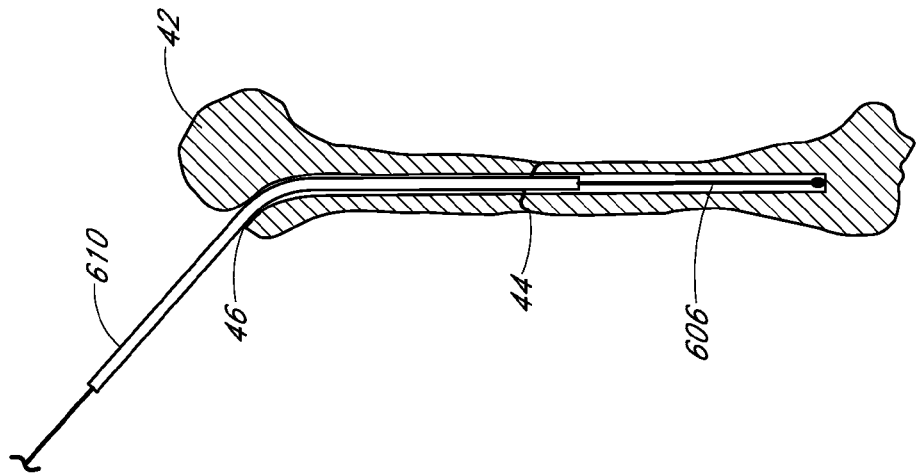
FIG. 73 is a schematic side view of a surgical procedure in a bone with a measurement of implant length according to an embodiment of the present invention.

In one embodiment illustrated at FIG. 73, the surgeon can measure the proper implant length. While maintaining fracture reduction with the distal ball tip of the guide wire 606 in proper position, the surgeon can place a Kelly clamp at a point as close as possible to the cortical entry point near access hole 46. The surgeon can proximally withdraw the guide wire 606 approximately 1 cm from the bone 42, and estimate the segmented intramedullary structure 300 length by measuring the exposed guide wire 606 (indicated by the arrow with reference number 608) using the a device length gauge. The surgeon can record the length or select an appropriate segmented intramedullary structure 300 and insert the guide wire 606 back into the intramedullary canal 40 and remove the Kelly clamp.

Figure 74:
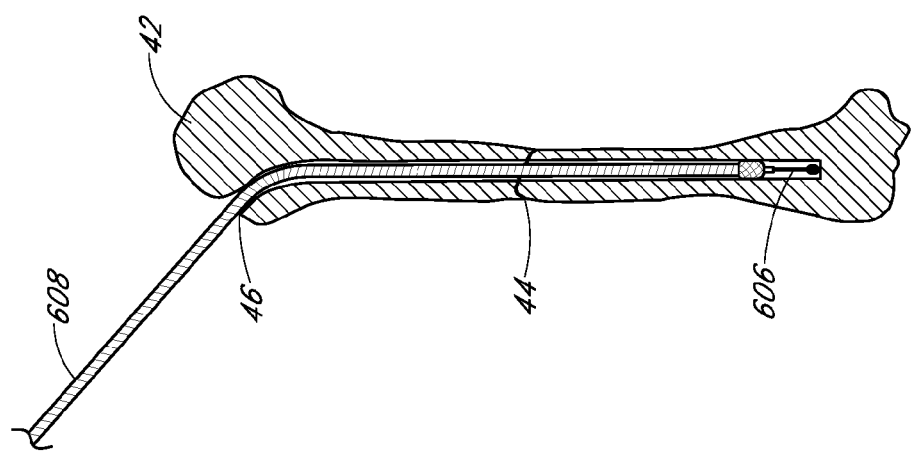
FIG. 74 is a schematic side view of a surgical procedure in a bone with a bone reamer according to an embodiment of the present invention.

In one embodiment illustrated at FIG. 74, the surgeon can ream the intramedullary canal 40. In various embodiments, one or more reamers 608 can be used. In one embodiment, beginning with a small diameter flexible reamer 608, such as in one example, a 6 mm flexible reamer 608, the surgeon can ream the medullary canal by placing the reamer 608 over the guide wire 606 and advancing it into the canal while maintaining fracture reduction. In one embodiment no guide wire 606 is required. In one embodiment the surgeon can use a tissue protector to prevent soft tissue damage while reaming. In one embodiment the surgeon can gradually increase reamers 608 diameters (for example, the reamers 608 can increase in diameter by 0.5 mm increments) until "chatter" is heard for the reamer 608, indicating the proper implant diameter. In one embodiment this diameter should correspond to preoperative estimates using radiographs or a radiographic canal ruler. Based on pre-op planning, the final reamer 608 diameter should be at least 1.0 mm larger than the nominal or central diameter of the chosen segmented intramedullary structure 300 to minimize the potential for fracture site distraction. In one embodiment the surgeon can place an obturator over the end of the guide wire 606 to hold it in position. The surgeon can remove the last reamer 608 by sliding it along the guide wire 606. Once the reamer 608 is out of the bone 42, the surgeon can remove the obturator and reamer 608.

Figure 75:
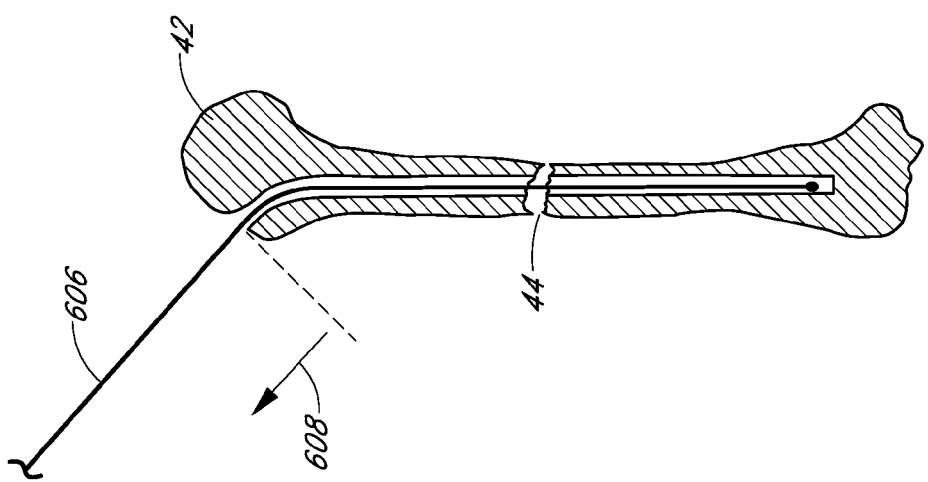
FIG. 75 is a schematic side view of a surgical procedure in a bone with an exchange tube according to an embodiment of the present invention.

In one embodiment illustrated at FIG. 75, the surgeon can select the diameter and length of the segmented intramedullary structure 300 based on the last reamer 608 diameter combined with the previously measured canal length. The surgeon can insert an exchange tube 610 over the guide wire 606, remove the guide wire 606 and insert the elongate member 350. The surgeon can confirm the elongate member 350 position under fluoroscopy. The surgeon can remove the exchange tube 610, being careful to maintain the position of the elongate member 350.

Figures 76, 77, 78:
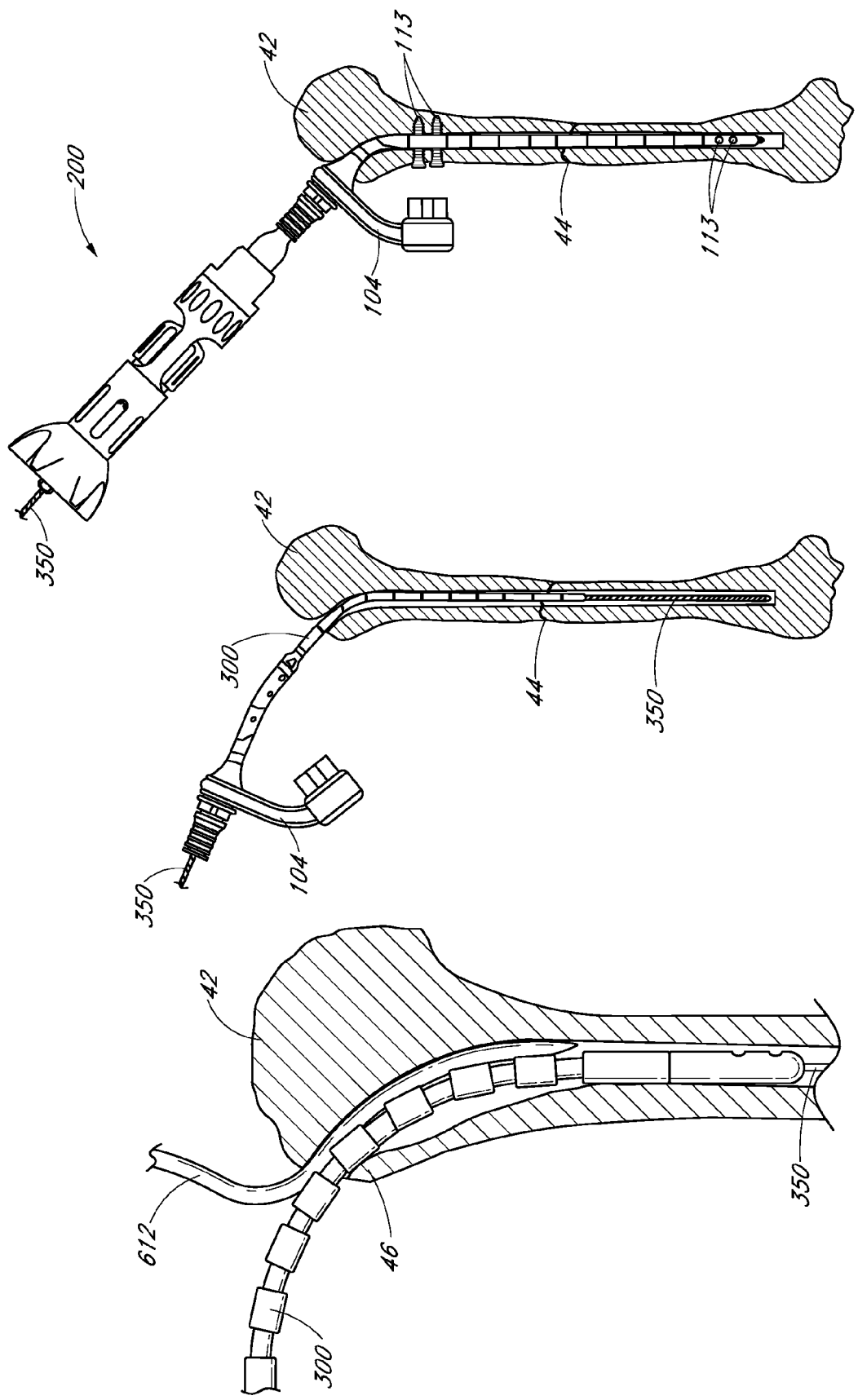

In one embodiment illustrated at FIG. 76, one embodiment of a segmented intramedullary structure 300 being inserted in a bent configuration in to a sectional view of a bone 42 according to an embodiment of the present invention. FIG. 76 illustrates one embodiment of an additional optional step in the method of inserting a segmented intramedullary structure 300 in a bent configuration in to an intramedullary canal 40 of a long bone 42 with an inserter guide 612. In one embodiment, an inserter guide 612 is a flexible, low friction strip with a width approximately equal to the width or diameter of the segmented intramedullary structure 300. The inserter guide 612 is inserted into the access hole 46 in the long bone 42 leading into the intramedullary canal 40.

In one embodiment illustrated at FIG. 77, the surgeon can insert a segmented intramedullary structure 300 into the bone 42. In one embodiment the surgeon can attach a proximal fixation screw guide-interface 104, or proximal drill guide, onto the proximal end 301 of the segmented intramedullary structure 300. In one embodiment the surgeon can use a locking bolt with a quick connect mechanism. The surgeon can advance the segmented intramedullary structure 300 over the proximal end of the elongate member 350. With the segmented intramedullary structure 300 in a flexed or bent configuration, the surgeon can advance the segmented intramedullary structure 300 over the elongate member 350 into the medullary canal 40. The surgeon can cake care to maintain the elongate member 350 position across the fracture 44 while advancing the segmented intramedullary structure 300 over the elongate member 350. In one embodiment the surgeon can optionally slightly rotate the proximal end 301 of the segmented intramedullary structure 300 to assist with insertion. The surgeon can sink the most proximal portion of the segmented intramedullary structure 300 at least 5 mm below the bone cortex and confirm position with fluoroscopy. In one embodiment the surgeon can apply preliminary tension to the elongate member 350 by manually pulling on the proximal end of the exposed elongate member 350 to compress the segments 310 of the segmented intramedullary structure 300 together. The surgeon can take caution not to bend or kink the elongate member 350 near the segmented intramedullary structure 300.

In one embodiment illustrated at FIG. 78, the surgeon can fixate the segmented intramedullary structure 300 with respect to the bone 42. In one embodiment the surgeon can fixate the segmented intramedullary structure 300 with respect to the bone 42 with proximal and distal bone screws 113. In other embodiments, other fixation techniques can be used. The surgeon can confirm that the proximal portion of the IFS is flush or slightly below the cortex of the bone 42. The surgeon can create an incision in line with the most proximal screw throughbore 112. In one embodiment two proximal throughbores 112 are configured for left-sided or right-sided access, and are close enough in proximity to have both bone screws 113 inserted through a single incision, approximately 5 mm long. The surgeon can bluntly dissect the incision to the cortex, taking care to avoid the axillary nerve and any of its arborized branches. The surgeon can spread the tissues and insert a proximal fixation screw guide-interface 104 until it contacts the bone 42. In one embodiment self-tapping bone screws 113 can be inserted with the proximal fixation screw guide-interface 104 through the bone 42 and into the throughbores 112 of the segmented intramedullary structure 300. In one embodiment the proximal fixation screw guide-interface 104 includes a 3.2 mm proximal drill sleeve. The surgeon can maintain the position of the proximal fixation screw guide-interface 104 against the bone 42 and use a drill bit to drill through the near and far cortices of the bone 42. In one embodiment the drill bit is a 3.2 mm calibrated drill bit. In surgeon can optionally stop drilling immediately after penetrating the far cortex of the bone 42. The surgeon can measure the necessary length for the bone screw 113 using the drill bit, a calibrated drill bit, or a calibrated measuring device. In various embodiments, the bone screw 113 can include diameters and length appropriate for the application. In some embodiments, the bone screw 113 has a diameter of 4.0 mm, 5.0 mm, or 6.0 mm, and a length in a range from about 16 mm to about 120 mm. The surgeon can select a bone screw 113 and insert it through the selected throughbore 112 of the segmented intramedullary structure 300 with a screw driver. In one embodiment the screw driver is a hex driver. The surgeon can repeat the procedure for the more distally-positioned proximal bone screw 113. In one embodiment, the more distally-positioned proximal bone screw 113 can be inserted before the more proximally-positioned proximal bone screw 113. The surgeon can reconfirm fracture 44 reduction with a visualization technique, such as fluoroscopy. The surgeon can ensure the segmented intramedullary structure 300 segments 310 are mostly compressed by manually tensioning the elongate member 350 as necessary by pulling on the proximal end of the elongate member 350. In one embodiment the surgeon avoids locking the segmented intramedullary structure 300 with distraction between the bone segments at the fracture 44. In one embodiment, the surgeon can place the patient's elbow on a mayo stand to support it to reduce distraction between bone segments at the fracture 44. The surgeon can utilize an AP view of the distal humerus and make a longitudinal incision over the segmented intramedullary structure 300 distal throughbores 112. The surgeon can identify the biceps fascia, split the fascia and deliver the drill tip to the bone 42. The surgeon can take caution to ensure drill tip placement so as to avoid inadvertent medialization of the drill tip. In one embodiment the surgeon can drill the holes in the bone for the distal bone screws 113. In one embodiment the surgeon can use self-tapping distal bone screws 113. In one embodiment the surgeon can insert the bone screws 113 using a freehand technique.

In one embodiment illustrated at FIG. 78, the surgeon can tension the elongate member 350 in the segmented intramedullary structure 300, which compresses the segments 310 with a cable tensioner assembly 200. In one embodiment the surgeon can ensure that the cable tensioner assembly 200 is ready to accept the elongate member 350 by loosening the tensioning threaded knob 240 until it stops. In one embodiment the loosening of the tensioning knob is counter-clockwise. In another embodiment the loosening of the tensioning knob is clockwise. The surgeon can insert the cable collet screw 280 into the distal end of the cable tensioner assembly 200 and press the cable collet screw 280 to firmly seat it on the cable tensioner assembly 200. The surgeon can slide the cable tensioner assembly 200 over the exposed elongate member 350 and attach cable tensioner assembly 200 to the proximal fixation screw guide-interface 104. In one embodiment the proximal fixation screw guide-interface 104 is already in place. In one embodiment the proximal fixation screw guide-interface 104 and cable tensioner assembly 200 can attach using a quick connect mechanism.

In one embodiment segmented intramedullary structure 300 elongate member 350 tensioning occurs in two steps: 1) tensioning of the elongate member 350, and 2) locking of the elongate member 350 with the cable collet screw 280. In one embodiment, when the cable tensioner assembly 200 is securely connected to the proximal fixation screw guide-interface 104—segmented intramedullary structure 300 construct. The surgeon can tighten the collet driver 250 knob by turning it 1-2 turns clockwise to partially advance the locking collet threads 282 of the cable collet screw 280 into the proximal end 301 of the segmented intramedullary structure 300. This step ensures proper threading of the cable collet screw 280 into the cable collet anchor 272 of the segmented intramedullary structure 300. The cable collet screw 280 should not be fully tightened yet. The surgeon can confirm the segmented intramedullary structure 300 position and fracture 44 reduction using fluoroscopy. The surgeon can apply tension to the elongate member 350 by rotating the tensioning threaded knob 240 clockwise until the tension indicator markings 247 reaches the 100 pound mark. In one embodiment the surgeon does not exceed 125 pounds of tension. Tensioning elongate member 350 should apply compression across the fracture site 44, such that the gap is reduced or eliminated between the fracture 44 fragments. Tensioning elongate member 350 should also reduce or eliminate gaps between the segments 310. The surgeon can confirm the position of the segmented intramedullary structure 300 and confirm fracture 44 reduction using a C-arm or fluoroscopy. The surgeon can locks the tensioned elongate member 350 within the segmented intramedullary structure 300 by tightening the cable collet screw 280 by rotating the collet driver 250, which rotates the driver shaft 252, clockwise to fully "seat" the cable collet screw 280.

In one embodiment, after the cable collet screw 280 has been secured, the surgeon can release the cable tensioner assembly 200 by loosening the tensioning threaded knob 240 until it stops. This will release the cable tensioner assembly 200 from the elongate member 350. The surgeon can release the quick connect outer ring to remove the cable tensioner assembly 200 and proximal fixation screw guide-interface 104 from the segmented intramedullary structure 300.

In one embodiment the surgeon can select an appropriate end cap 290 and slide it distally over the exposed elongate member 350. The surgeon can thread the end cap 290 into place using an end cap driver. The surgeon can confirm the position of the segmented intramedullary structure 300 using fluoroscopy. The surgeon can use cable cutters to cut the elongate member 350 as close to the proximal end 301 of the segmented intramedullary structure 300 as possible. In one embodiment the surgeon can cut the elongate member 350 as close to the proximal end of the end cap 290 as possible. The surgeon can close the wound in layers.

Figure 79:
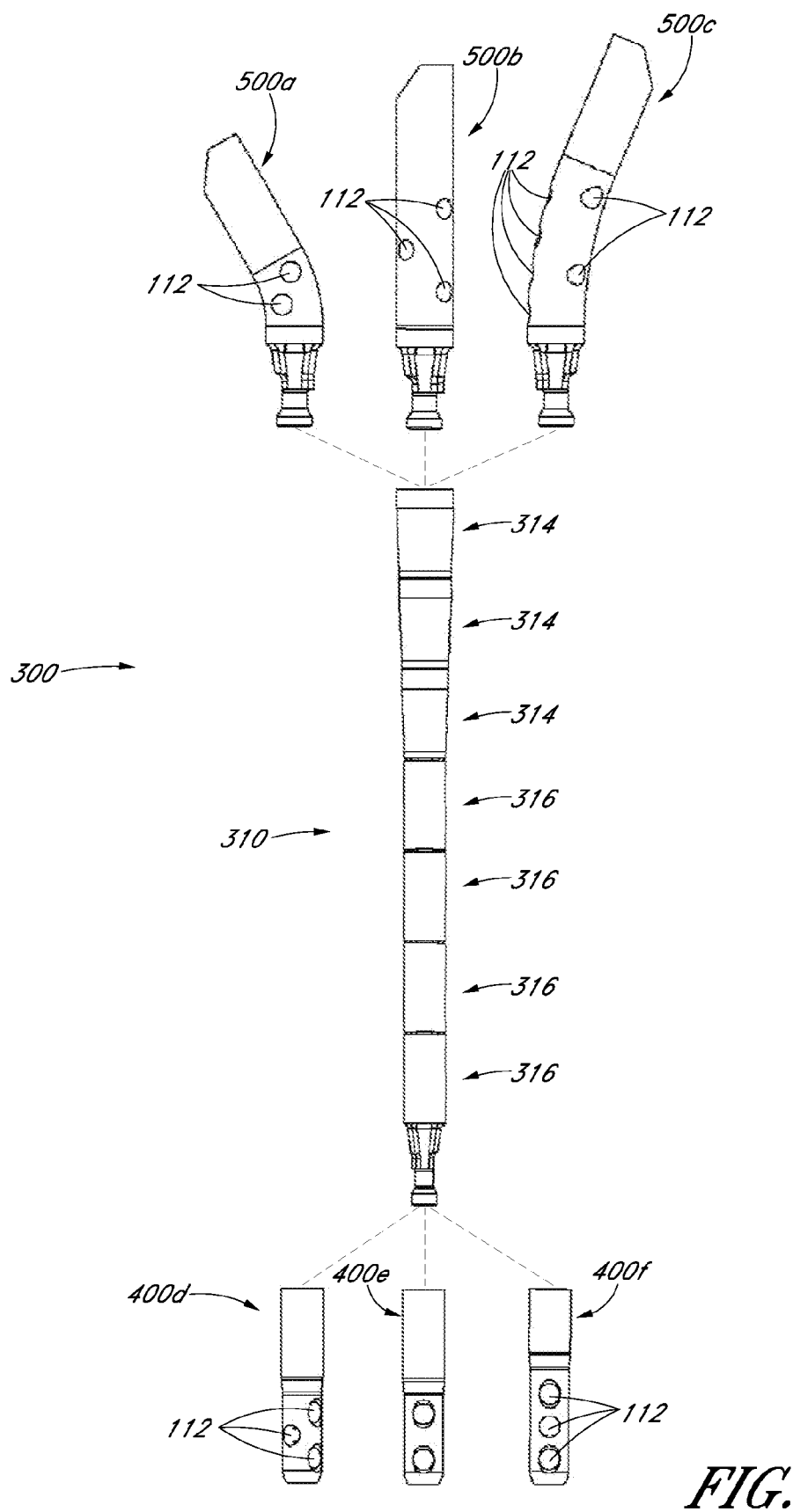

In various embodiments, different combinations of segments 310 can be assembled or manufactured into a custom segmented intramedullary structure 300 based on specific parameters of the bone in which the segmented intramedullary structure 300 will be implanted. In various embodiments, different combinations of segments 310 can be used or combined in a modular fashion to assemble custom made segmented intramedullary structures 300 based on the bone and application for the structure. In various embodiments the overall configuration or shape of the segmented intramedullary structure 300 may be straight, substantially straight, or curved along any one segment 310 or any sets of segments 310 depending on the selection of parts from an array of parts with various shapes, sizes and features. Each segment 310 can be substantially straight or curved, and any set of segments 310 can have interfaces providing for angles between adjacent segments 310. In various embodiments, segments 310 can also comprise one or more transition segments 314 and/or uniform segments 316 disposed between the distal end segment 400 and the proximal end segment 500. Segments 310 can be selected based on features the segments 310 have for use based on an evaluation of parameters of the bone for implantation. Parameters, as discussed herein, can include bone or intramedullary canal diameter, length, width, height, curvature (if any), deviation from linear, fracture geometry, bone geometry, tissue geometry, anatomical features such as abnormalities or other features, to name a few. In various embodiments, different combinations of embodiments of segments 314 and/or uniform segments 316 can be disposed between different embodiments of a distal end segment 400 and different embodiments of a proximal end segment 500. Referring to one embodiment illustrated in FIG. 79, different non-limiting embodiments of a proximal end segment 500*a*, 500*b*, and 500*c*, with different features, such as various curvatures (if any), lengths, orientations, features of throughbores 112, locking mechanisms, and more can be selected depending on parameters of the bone or patient in which the structure is to be implanted. Similarly, different non-limiting embodiments of a distal end segment 400*d*, 400*e*, 400*f* can be selected. Likewise, any combination of uniform segments 316 can be used, with different sizes arranged with complementary interfaces. In one optional embodiment various uniform segments 316 may be used with complementary interfaces but have different outer body parameters, such as diameter, texture or other alignment or bone engagement or bone ingrowth enhancing structure. Likewise, any combination of transition segments 314 can be used, with different sizes arranged with complementary interfaces. Various combinations of transition segments 314 may be used for a continuous transition along a number of transition segments 314, or can vary in taper with increases in diameter or width as desired depending on the sequence of segment 310 assembly.

In one method of assembly, manufacture, or construction of the segmented intramedullary structure 300, a surgeon could assemble a modular or custom segmented intramedullary structure 300 while in the operating room. In one embodiment an evaluation of bone parameters using any imaging or assessment technique can be used, then a series of segments 310 could be assembled using a selected or suitable series and number of segments 310 based on the bone evaluation. In one embodiment a segment 310 may be selected based on the best fitting curvature, orientation, and/or throughbores 112 for a surgical approach to the bone. Different segments 310 can be selected for accommodating for a fracture, increased stability, screw placement, and other aspects relating to features and parameters of the device with the bone.

Typically, at least a proximal segment, a distal segment and an intermediate segment will be assembled to form a final construct. Depending upon the desired length of the assembled implant, at least two, or three or five or more intermediate segments may be used. Each of the intermediate segments is provided with a proximal interface, for engaging a proximally adjacent segment, and a distal interface for engaging a distally adjacent segment. The proximal and or distal interfaces may be provided with a retention lock such as a snap ring as has been described elsewhere herein or other complementary retention structure. The retention lock permits the physician to connect two adjacent segments together while assembling the implant, and also to preserve the implant removal feature discussed below.

In the modular, customizable device, the distal end segment may be provided with a proximally extending tightening element such as a pull or push element, rotatable shaft or other structure for locking the finished implant in its implanted configuration. Each of the intermediate segments is provided with an axially extending lumen, for receiving the tightening element therethrough. During assembly, the physician feeds the axially extending tightening element from the distal most segment through each successive intermediate segment until the desired length is reached. The proximal segment is provided with a lock, for locking the tightening element. The tightening element may be provided with an initial length which exceeds the length of the assembled implant. The proximal excess of the tightening element can be cut off or otherwise detached and discarded to conform to the length of the implant. Alternatively, it may be left subcutaneously so that it can be retrieved and used as a guide to the implant for future revision surgery. Alternatively, the tightening element may be provided in a modular configuration, with a portion of the tightening element carried by each segment, so that it is effectively assembled as each successive segment is connected to the implant.

Procedures for Extracting or Removing a Segmented Intramedullary Structure

In one embodiment an implanted segmented intramedullary structure 300 can be removed from the patient. In one embodiment an implanted segmented intramedullary structure 300 can be removed from the patient by reversing some of the steps used in implantation. In one embodiment the surgeon can access the access hole 46 in the bone with an incision and moving tissue out of the way. Visualization techniques, such as fluoroscopy, or manual palpation of the tissue can be used to locate bone screw 113 extraction sites. Use of minimally invasive, percutaneous, or open surgical techniques can be used to access the access site and screw sites in the patient. In one embodiment the end cap 290 is removed. In one embodiment the bone screws 113 are removed. In one embodiment the cable collet screw 280 is loosened. In one embodiment the cable collet screw 280 is loosened with a collet screw removal tool. In one embodiment the cable collet screw 280 is loosened with a cable tensioner assembly 200 operated in a manner to reduce tension in the elongate member 350. In one embodiment, the proximal end of the elongate member 350 is grasped with a tool for extracting the elongate member 350. In one embodiment extraction of elongate member 350 pulls the distal end segment 400 of the segmented intramedullary structure 300 in a proximal direction toward the access hole 46. In one embodiment the cable collet screw 280 is loosened, moved proximally along elongate member 350, and tightened back on the elongate member 350 to grasp the elongate member 350 at a more proximal location. In one embodiment a loosened elongate member 350 releases segments 310 in the segmented intramedullary structure 300 from the compressed configuration, allowing the segments 310 to distract or move with respect to each other. In one embodiment the tension in elongate member 350 is reduced enough to allow adjacent segments 310 in the segmented intramedullary structure 300 to move into a bent configuration 307 sufficient for extraction of at least one segment 310 though the access hole 46. In one embodiment segments 310 are removed from bone 42 sequentially. In one embodiment, it is possible that the segmented intramedullary structure 300 is attached to patient tissue or bone, or that some bone cement or adhesives were used around the implanted device, or other additional anchoring mechanisms. In one embodiment the proximal end 301 of the segmented intramedullary structure 300 may be tapped or vibrated with a hammer or device configured to shake or vibrate the segmented intramedullary structure 300 at a frequency, such as a resonant frequency, to assist in the removal of the segmented intramedullary structure 300 from the bone 42. In one embodiment extraction of a segmented intramedullary structure 300 includes providing sufficient force to break one segment 310 free from the surrounding bone at a time. For example, the force required to shear the bone ingrowth into one segment, such as the most proximal segment 310, is less than the force required to shear the bony ingrowth throughout the length of the entire segmented intramedullary structure 300 at once. For example, resistance to removal may correlate to surface area of the implant being removed. If one segment is broken free at a time, the resistance to overcome removal would be proportionate to the surface area of that one segment instead of the entire implant. In one embodiment the shear force to free one segment 310 is less than the shear force to free multiple segments 310 at the same time. In one embodiment extraction of a segmented intramedullary structure 300 includes attaching a removal device to the most proximal segment 310 and pulling the most proximal segment 310 proximally. In one embodiment the removal device is a slap hammer, and the slap hammer is attached to the most proximal segment 310 and actuated with sufficient force to free the most proximal segment 310 from the bone 42. In various embodiments the snap ring or other locking structure permits distraction between adjacent segments of at least about 0.5 mm, generally at least about 1 mm or 2 mm but often no more than about 5 mm or 10 mm. As a result, a loosened segment 310 may be proximally retracted to the limit of its travel. Further proximal force applied to the segment 310 will be transferred by the locking structure to the next adjacent distal segment so that it may be broken free from surrounding bone 42. The process can be repeated to remove all segments 310 from the bone 42.

Thus, an improved intramedullary structure has been provided as described above. While the structure has been described in terms of certain specific embodiments, there is no intention to limit the invention to the same. It will be understood that the foregoing is only illustrative of the principles of the invention, and that various modifications, alterations, and combinations can be made by those skilled in the art without departing from the scope and spirit of the invention. Accordingly, it is not intended that the invention be limited, except as by the appended claims.

What is claimed is:

1. An implantable intramedullary fixation structure having a proximal end, a distal end and an elongate body adapted to be received in the intramedullary canal of a long bone comprising:
    a plurality of segments, each segment comprising:
        a first interface;
        a complementarily-shaped second interface such that the first interface of a segment cooperatively engages the second interface of an adjacent segment; and
        a channel aligned along a longitudinal axis of the segment,
        wherein the first interface comprises a first interface flat feature and a first interface taper feature,
        wherein the second interface comprises a second interface flat feature and a second interface taper feature,
        wherein the first interface flat feature and second interface flat feature are configured to limit relative bending between adjacent segments in a first plane along the longitudinal axis of the segment,
        wherein the first interface taper feature and second interface taper feature are configured to allow relative bending between adjacent segments in a second plane along the longitudinal axis of the segment, the second plane substantially perpendicular to the first plane;
    an elongate element extending through the channels to apply a compressive force along the longitudinal axis of the fixation structure; and
    a lock in at least one of the proximal end and the distal end, for securing the elongate element tension member;
    wherein activation of the elongate element tensioning member causes the fixation structure to convert from a substantially flexible state to a substantially rigid state.

2. The intramedullary structure of claim 1, wherein the lock comprises a collet.

3. The intramedullary structure of claim 1, wherein the rigid state is non-linear.

4. The intramedullary structure of claim 1, wherein the rigid state conforms to the intramedullary canal.

5. The intramedullary structure of claim 1 wherein the complementarily-shaped ends of the segments permit relative movement between adjacent segments substantially in a single plane.

6. The intramedullary structure of claim 1 wherein adjacent segments are secured to each other.

7. The intramedullary structure of claim 1, further comprising a guide for positioning each segment in the intramedullary canal.

8. The intramedullary structure of claim 1, wherein an axial length of the intramedullary structure is reduced up to about 5 mm in compression for reduction of a bone fracture.

9. The intramedullary structure of claim 1, wherein an axial length of the intramedullary structure is reduced in a range of about 1 mm to 5 mm in secondary compression for reduction of a bone fracture.

10. An implantable intramedullary fixation device adapted to be received in the intramedullary canal of a long bone comprising:
an elongate body, transformable between a flexible state for implantation within a bone, and a rigid state for fixing a fracture in a bone; and
a plurality of segments for defining the body, each segment having:
a first interface having an axial extension comprising a first interface flat feature and a first interface taper feature; and
a complementarily-shaped second interface having a concavity comprising a second interface flat feature and a second interface taper feature,
wherein the first interface flat feature and second interface flat feature are configured to limit relative bending between adjacent segments in a first plane along the longitudinal axis of the segment,
wherein the first interface taper feature and second interface taper feature are configured to allow relative bending between adjacent segments in a second plane along the longitudinal axis of the segment, the second plane substantially perpendicular to the first plane,
such that the first interface of a segment cooperatively engages the second interface of an adjacent segment,
the segments comprising a channel so as to be receivable over a guide for positioning in the intramedullary canal,
wherein the body is bendable in a single plane within the flexible state.

11. The intramedullary device of claim 10 further comprising a tensioning member extending the length thereof to apply a compressive force along the longitudinal axis of the structure.

12. The intramedullary device of claim 11 wherein the axial length of the body is reduced up to about 5 mm in secondary compression for reduction of a bone fracture.

13. The intramedullary device of claim 10 wherein the axial length of the body is reduced as the body is transformed from the flexible state to the rigid state.

14. The intramedullary device of claim 10 wherein the complementarily-shaped interfaces of the segments comprise friction enhancing surface structures.

15. The intramedullary device of claim 10 wherein adjacent segments are secured to each other.

16. The intramedullary device of claim 10 further comprising at least one fastener received in at least one of the segments for securing the device in place in the long bone.

17. An implantable intramedullary fixation structure having a proximal end, a distal end and an elongate body adapted to be received in the intramedullary canal of a long bone comprising:
a plurality of segments, each segment having a first interface having an axial extension and a complementarily-shaped second interface having a concavity such that the first interface of a segment cooperatively engages the second interface of an adjacent segment, each segment including a channel;
a snap ring carried by the axial extension for engaging the concavity to join adjacent segments end to end under distraction;
an elongate element extending through the channels to apply a compressive force along the longitudinal axis of the fixation structure; and
a lock in at least one of the proximal end and the distal end, for securing the elongate element;
wherein activation of the elongate element causes the fixation structure to convert from a substantially flexible state to a substantially rigid state.

18. The intramedullary structure of claim 17 wherein the complementarily-shaped ends of the segments permit relative movement between adjacent segments substantially in a single plane.

19. The intramedullary structure of claim 17, further comprising a guide for positioning each segment in the intramedullary canal.

20. The intramedullary structure of claim 17, wherein an axial length of the intramedullary structure is reduced in a range of about 1 mm to 5 mm in secondary compression for alignment of a bone fracture.

* * * * *